United States Patent
Licha et al.

(12) 
(10) Patent No.: US 6,630,570 B1
(45) Date of Patent: Oct. 7, 2003

(54) SHORT-CHAIN PEPTIDE-DYE CONJUGATES AS CONTRAST MEDIA FOR OPTICAL DIAGNOSIS

(75) Inventors: Kai Licha, Falkensee (DE); Andreas Becker, Hennigsdorf (DE); Wolfhard Semmler, Berlin (DE); Bertram Wiedenmann, Berlin (DE); Carsten Hessenius, Berlin (DE); Rudolf Volkmer-Engert, Berlin (DE); Jens Schneider-Mergner, Berlin (DE)

(73) Assignee: Insitut für Diagnostikforschung GmbH, Berlin (DE)

( * ) Notice: Subject to any disclaimer, the term of this patent is extended or adjusted under 35 U.S.C. 154(b) by 0 days.

(21) Appl. No.: 09/528,200

(22) Filed: Mar. 17, 2000

Related U.S. Application Data
(60) Provisional application No. 60/128,785, filed on Apr. 12, 1999.

(30) Foreign Application Priority Data

Sep. 4, 1999 (DE) .......................................... 199 17 713

(51) Int. Cl.⁷ ............................................... A61K 38/16
(52) U.S. Cl. ........................ 530/324; 530/325; 530/326; 530/327; 530/328; 530/329; 530/330; 514/12; 514/13; 514/14; 514/15; 514/16; 422/9.6; 422/82.08; 436/546
(58) Field of Search ................................ 530/324–330; 514/12–16; 424/9.6; 422/82.08; 436/546

(56) References Cited

U.S. PATENT DOCUMENTS

| | | | |
|---|---|---|---|
| 5,382,654 A | 1/1995 | Lyle et al. ................... 530/311 |
| 5,627,027 A | 5/1997 | Waggoner ...................... 435/6 |
| 5,753,205 A | 5/1998 | Lyle et al. ................. 424/1.69 |
| 5,824,772 A | * 10/1998 | Vincent ....................... 530/311 |
| 5,849,261 A | 12/1998 | Dean et al. ................. 424/1.69 |
| 6,217,848 B1 | * 4/2001 | Achilefu ..................... 424/9.1 |
| 6,225,050 B1 | * 5/2001 | Waggoner ...................... 435/6 |
| 6,329,531 B1 | 12/2001 | Turner ........................ 548/455 |

FOREIGN PATENT DOCUMENTS

| | | | |
|---|---|---|---|
| EP | 0588754 | * | 3/1994 |
| EP | 0591820 | | 4/1994 |
| WO | 9006949 | | 6/1990 |
| WO | 96/23527 | * | 8/1996 |
| WO | 9630055 | | 10/1996 |
| WO | 96/30055 | * | 10/1996 |
| WO | 9740104 | | 10/1997 |
| WO | 9857667 | | 12/1998 |

OTHER PUBLICATIONS

Patent Abstracts of Japan JP4297498 (Oct. 21, 1992).
Patent Abstracts of Japan JP6202260 (Jul. 22, 1994).
Patent Abstracts of Japan JP01088537 (Apr. 3, 1989).
Patent Abstracts of Japan JP01091134 (Apr. 10, 1989).
English Abstract DE 19817517.
English Abstract DE 19649971.
Reubi J–C: "The role of peptides and their receptors as tumor markers" *Endocrinology and Metabolism clinics of North America*, vol 22, No. 4 (1993) pp. 917–939.
Licha K. et al: "Highly parallel nano–synthesis of cleavable peptide–dye conjugates on cellulose membranes" *Tetrahedron Letters*, vol. 41, No. 11 (Mar. 2000). pp 1711–1715.
Reifke et al.: "In vivo characterization of cyanine dyes as contrast agents for near–infrared imaging" *Proceedings of the SPIE*, vol 2927 (Sep. 1996) pp. 199–208 Abstract Only.
Licha et al: "Synthesis and characterization of cyanine dyes as contrast agents for near–infrared imaging" *Proceedings of the SPIE*, vol 2927 (Sep. 1996) pp. 192–198 Abstract Only.
Licha et al: "Synthesis and characterization of cyanine dye–polyethylene conjugates as contrast agents for in–vivo flourescence imaging" *Proceedings of the SPIE*, vol 2927 (Sep. 1996) pp. 98–102 Abstract Only.
Mank A J G et al.: " Visible Diode Laser–induced fluorescence detection in liquid chromatography after precolumn derivatization of amines" *Analytical Chemistry* vol 67 (1995) pp. 1742–1748.
Deligeorgiev T G et al.: "Preparation of monomethine Cyanine dyes for Nucleic Acid Detection" *Dyes and Pigments* vol 37, no,3, (May 1998) pp. 205–211.
Jaehde Ulrich et al.: "Quantification and visualization of the transprot of octreotide, a somatostatin analoque across monolayers of cerebrovascular endothelial cells" *Pharmaceutical Research*, vol. 11, No 3 pp. 442–448.
Song Z M et al.: "Characterization of myenteric interneurons with somatostatin immunoreactivity in the guinea–pig small intestine" *Neuroscience* vol 80,No. 3 (1997)pp. 907–923.

\* cited by examiner

*Primary Examiner*—Christopher S. F. Low
*Assistant Examiner*—David Lukton
(74) *Attorney, Agent, or Firm*—Millen, White, Zelano & Branigan, P.C.

(57) ABSTRACT

The invention relates to compounds for tumor diagnosis that consist of conjugates of dyes with short-chain peptides, which are derived from vaso-active intestinal peptide, somatostatin or neurotensin, the use of these compounds as optical dignostic agents, and diagnostic agents that contain these compounds.

31 Claims, 7 Drawing Sheets

Photophysical Properties of Dye-Peptide Conjugates 14-38

Solvent: PBS (phosphate buffered saline, pH 7.4)

| Compound # | Absorption Maximum $\lambda_{abs, max}$ (nm) | Fluorescence Maximum $\lambda_{em, max}$ (nm) | Extinction Coefficient $\varepsilon$ ($\ell$ mol$^{-1}$ cm$^{-1}$) |
|---|---|---|---|
| 14 | 556 | 582 | 98 000 |
| 15 | 649 | 675 | 105 000 |
| 16 | 746 | 781 | 125 000 |
| 17 | 749 | 783 | 115 000 |
| 18 | 556 | 580 | 108 000 |
| 19 | 649 | 677 | 110 000 |
| 20 | 746 | 781 | 135 000 |
| 21 | 552 | 580 | not determined |
| 22 | 648 | 676 | 111 000 |
| 23 | 746 | 781 | not determined |
| 24 | 746 | 783 | not determined |
| 25 | 747 | 784 | 121 000 |
| 26 | 748 | 784 | 156 000 |
| 27 | 748 | 784 | 159 000 |
| 28 | 552 | 579 | 102 000 |
| 29 | 648 | 676 | 111 000 |
| 30 | 746 | 781 | 128 000 |
| 31 | 746 | 781 | not determined |
| 32 | 748 | 782 | 169 000 |
| 33 | 552 | 579 | 101 000 |
| 34 | 648 | 677 | 121 000 |
| 35 | 746 | 780 | 130 000 |
| 36 | 747 | 781 | 109 000 |
| 37 | 554 | 578 | 99 000 |
| 38 | 648 | 676 | 121 000 |

FIG. 4

|   | 1A | 2C | 3D | 4E | 5F | 6G | 7H | 8I | 9K | 10L | 11M | 12N | 13P | 14Q | 15R | 16S | 17T | 18V | 19W | 20Y |
|---|---|---|---|---|---|---|---|---|---|---|---|---|---|---|---|---|---|---|---|---|
| 1H | 46 | 143 | 43 | 33 | 103 | 72 | 100 | 126 | 52 | 156 | 77 | 60 | 45 | 58 | 85 | 68 | 76 | 33 | 25 | 6 |
| 2S | 91 | 93 | 32 | 58 | 167 | 77 | 96 | 184 | 50 | 95 | 131 | 50 | 66 | 235 | 68 | 100 | 152 | 121 | 235 | 121 |
| 3D | 111 | 132 | 100 | 110 | 110 | 75 | 103 | 105 | 66 | 101 | 96 | 69 | 66 | 57 | 54 | 59 | 67 | 89 | 149 | 86 |
| 4A | 100 | 97 | 31 | 33 | 135 | 120 | 62 | 95 | 59 | 77 | 111 | 66 | 56 | 110 | 76 | 130 | 63 | 79 | 172 | 140 |
| 5V | 66 | 81 | 33 | 43 | 100 | 84 | 70 | 107 | 66 | 113 | 105 | 52 | 41 | 72 | 82 | 59 | 114 | 100 | 144 | 95 |
| 6F | 21 | 7 | 18 | 16 | 100 | 22 | 26 | 78 | 105 | 78 | 51 | 4 | 4 | 20 | 28 | 20 | 12 | 9 | 75 | 61 |
| 7T | 53 | 86 | 28 | 29 | 58 | 41 | 63 | 62 | 41 | 69 | 12 | 89 | 36 | 60 | 57 | 68 | 100 | 111 | 94 | 21 |
| 8D | 134 | 178 | 100 | 104 | 231 | 153 | 199 | 223 | 240 | 225 | 208 | 190 | 71 | 250 | 407 | 177 | 219 | 220 | 251 | 184 |
| 9N | 84 | 174 | 45 | 21 | 151 | 125 | 104 | 114 | 102 | 115 | 145 | 100 | 57 | 117 | 153 | 114 | 102 | 89 | 135 | 117 |
| 10Y | 39 | 81 | 15 | 17 | 88 | 18 | 26 | 40 | 45 | 90 | 63 | 28 | 20 | 27 | 39 | 35 | 26 | 49 | 132 | 100 |
| 11T | 116 | 240 | 33 | 46 | 178 | 106 | 87 | 211 | 216 | 169 | 111 | 146 | 41 | 128 | 246 | 108 | 100 | 112 | 122 | 137 |
| 12R | 49 | 91 | 19 | 25 | 61 | 25 | 42 | 50 | 85 | 60 | 57 | 38 | 15 | 43 | 100 | 38 | 42 | 48 | 80 | 57 |
| 13L | 80 | 113 | 13 | 17 | 86 | 21 | 60 | 84 | 79 | 105 | 80 | 35 | 14 | 49 | 92 | 55 | 45 | 66 | 123 | 87 |
| 14R | 40 | 113 | 9 | 25 | 63 | 26 | 28 | 73 | 87 | 89 | 63 | 23 | 15 | 43 | 100 | 24 | 26 | 49 | 71 | 39 |
| 15K | 72 | 192 | 17 | 33 | 108 | 37 | 57 | 87 | 100 | 104 | 92 | 52 | 15 | 74 | 138 | 49 | 55 | 76 | 81 | 90 |
| 16Q | 100 | 154 | 19 | 41 | 94 | 39 | 48 | 108 | 106 | 115 | 108 | 69 | 21 | 100 | 150 | 73 | 84 | 120 | 174 | 107 |
| 17M | 78 | 129 | 31 | 54 | 106 | 45 | 74 | 118 | 91 | 111 | 100 | 90 | 18 | 141 | 118 | 70 | 56 | 72 | 126 | 87 |
| 18A | 100 | 137 | 21 | 42 | 133 | 42 | 73 | 92 | 159 | 115 | 122 | 82 | 25 | 104 | 172 | 78 | 60 | 99 | 137 | 95 |
| 19V | 110 | 149 | 12 | 15 | 80 | 26 | 22 | 105 | 28 | 104 | 65 | 19 | 18 | 26 | 49 | 23 | 29 | 100 | 91 | 66 |
| 20K | 69 | 132 | 12 | 29 | 83 | 31 | 42 | 69 | 100 | 78 | 68 | 27 | 12 | 44 | 121 | 35 | 27 | 50 | 88 | 72 |
| 21K | 61 | 104 | 29 | 46 | 75 | 22 | 46 | 51 | 100 | 69 | 66 | 59 | 11 | 65 | 94 | 49 | 46 | 66 | 117 | 67 |
| 22Y | 19 | 83 | 8 | 10 | 97 | 15 | 21 | 49 | 24 | 53 | 35 | 14 | 14 | 18 | 42 | 17 | 18 | 62 | 115 | 100 |
| 23L | 17 | 43 | 10 | 13 | 42 | 14 | 17 | 70 | 22 | 100 | 29 | 15 | 18 | 20 | 26 | 13 | 14 | 31 | 57 | 28 |
| 24N | 111 | 160 | 35 | 54 | 95 | 26 | 59 | 125 | 76 | 79 | 136 | 100 | 28 | 85 | 80 | 95 | 73 | 141 | 191 | 65 |
| 25S | 75 | 134 | 40 | 37 | 85 | 54 | 61 | 80 | 89 | 63 | 83 | 92 | 24 | 67 | 116 | 100 | 68 | 39 | 145 | 108 |
| 26I | 25 | 46 | 9 | 12 | 76 | 13 | 21 | 100 | 47 | 119 | 58 | 15 | 9 | 24 | 65 | 112 | 40 | 85 | 115 | 122 |
| 27L | 65 | 68 | 23 | 18 | 124 | 76 | 34 | 109 | 36 | 100 | 60 | 34 | 19 | 31 | 51 | 56 | 47 | 71 | 93 | 80 |
| 28N | 69 | 104 | 45 | 59 | 88 | 81 | 55 | 53 | 70 | 72 | 82 | 100 | 17 | 69 | 62 | 60 | 60 | 61 | 108 | 32 |
|   | 1A | 2C | 3D | 4E | 5F | 6G | 7H | 8I | 9K | 10L | 11M | 12N | 13P | 14Q | 15R | 16S | 17T | 18V | 19W | 20Y |

FIG. 7

SEQUENCE LISTING

<160> NUMBER OF SEQ ID NOS: 196

<210> SEQ ID NO 1
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

His Trp Asp Ala Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 2
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

His Ser Asp Ala Val Phe Thr Phe Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Ser Asp Ala Val Phe Thr Lys Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

His Ser Asp Ala Val Phe Thr Gln Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 5
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

His Ser Asp Ala Val Phe Thr Arg Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

His Ser Asp Ala Val Phe Thr Trp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

His Ser Asp Ala Val Phe Thr Asp Asn Tyr Arg Arg Leu Arg Lys Gln
 1               5                  10                  15

Met Ala Val Lys Lys Tyr Leu Asn Ser Ile Leu Asn
            20                  25

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His Ser Asp Ala Val Phe Thr Asp Asn Tyr Thr Arg Leu Arg Lys Gln
 1               5                  10                  15

Met Arg Val Lys Lys Tyr Leu Asn Ser Ile Leu Asn
            20                  25

<210> SEQ ID NO 9
<211> LENGTH: 14
<212> TYPE: PRT
<213> ORGANISM: Homo sapiens

<400> SEQUENCE: 9

Ala Gly Cys Lys Asn Phe Phe Trp Lys Thr Phe Thr Ser Cys
 1               5                  10

<210> SEQ ID NO 10
<211> LENGTH: 13
<212> TYPE: PRT
<213> ORGANISM: Homo sapiens
<220> FEATURE:
<221> NAME/KEY: MOD_RES

```
<222> LOCATION: (1)
<223> OTHER INFORMATION: pGlu

<400> SEQUENCE: 10

Glu Leu Tyr Glu Asn Lys Pro Arg Arg Pro Tyr Ile Leu
 1               5                  10

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Leu Arg Lys Gln Met Ala Val Lys Lys Tyr Leu Asn Ser Ile Leu
 1               5                  10                  15

Asn

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Arg Lys Gln Met Ala Val Lys Lys Tyr Leu Asn Ser Ile Leu Asn
 1               5                  10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Lys Gln Met Ala Val Lys Lys Tyr Leu Asn Ser Ile Leu Asn
 1               5                  10                  15

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Gln Met Ala Val Lys Lys Tyr Leu Asn Ser Ile Leu Asn
 1               5                  10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Met Ala Val Lys Lys Tyr Leu Asn Ser Ile Leu Asn
 1               5                  10
```

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met Ala Val Lys Lys Tyr Leu Asn Ser Ile Leu Asn
 1               5                  10

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Val Lys Lys Tyr Leu Asn Ser Ile Leu Asn
 1               5                  10

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Leu Arg Lys Gln Met Ala Val Lys Lys Tyr Leu Asn Ser Ile Leu
 1               5                  10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Arg Lys Gln Met Ala Val Lys Lys Tyr Leu Asn Ser Ile Leu
 1               5                  10                  15

<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Lys Gln Met Ala Val Lys Lys Tyr Leu Asn Ser Ile Leu
 1               5                  10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Gln Met Ala Val Lys Lys Tyr Leu Asn Ser Ile Leu
  1               5                  10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Met Ala Val Lys Lys Tyr Leu Asn Ser Ile Leu
  1               5                  10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Met Ala Val Lys Lys Tyr Leu Asn Ser Ile Leu
  1               5                  10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Val Lys Lys Tyr Leu Asn Ser Ile Leu
  1               5                  10

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Leu Arg Lys Gln Met Ala Val Lys Lys Tyr Leu Asn Ser Ile
  1               5                  10                  15

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Arg Lys Gln Met Ala Val Lys Lys Tyr Leu Asn Ser Ile
  1               5                  10

<210> SEQ ID NO 27
<211> LENGTH: 13

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Lys Gln Met Ala Val Lys Lys Tyr Leu Asn Ser Ile
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Gln Met Ala Val Lys Lys Tyr Leu Asn Ser Ile
 1               5                  10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Met Ala Val Lys Lys Tyr Leu Asn Ser Ile
 1               5                  10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Met Ala Val Lys Lys Tyr Leu Asn Ser Ile
 1               5                  10

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Val Lys Lys Tyr Leu Asn Ser Ile
 1               5

<210> SEQ ID NO 32
<211> LENGTH: 14
<212> TYPE: PRT
<213> ORGANISM: Homo sapiens

<400> SEQUENCE: 32

Arg Leu Arg Lys Gln Met Ala Val Lys Lys Tyr Leu Asn Ser
 1               5                  10
```

```
<210> SEQ ID NO 33
<211> LENGTH: 13
<212> TYPE: PRT
<213> ORGANISM: Homo sapiens

<400> SEQUENCE: 33

Leu Arg Lys Gln Met Ala Val Lys Lys Tyr Leu Asn Ser
 1               5                  10

<210> SEQ ID NO 34
<211> LENGTH: 12
<212> TYPE: PRT
<213> ORGANISM: Homo sapiens

<400> SEQUENCE: 34

Arg Lys Gln Met Ala Val Lys Lys Tyr Leu Asn Ser
 1               5                  10

<210> SEQ ID NO 35
<211> LENGTH: 11
<212> TYPE: PRT
<213> ORGANISM: Homo sapiens

<400> SEQUENCE: 35

Lys Gln Met Ala Val Lys Lys Tyr Leu Asn Ser
 1               5                  10

<210> SEQ ID NO 36
<211> LENGTH: 10
<212> TYPE: PRT
<213> ORGANISM: Homo sapiens

<400> SEQUENCE: 36

Gln Met Ala Val Lys Lys Tyr Leu Asn Ser
 1               5                  10

<210> SEQ ID NO 37
<211> LENGTH: 9
<212> TYPE: PRT
<213> ORGANISM: Homo sapiens

<400> SEQUENCE: 37

Met Ala Val Lys Lys Tyr Leu Asn Ser
 1               5

<210> SEQ ID NO 38
<211> LENGTH: 8
<212> TYPE: PRT
<213> ORGANISM: Homo sapiens

<400> SEQUENCE: 38

Ala Val Lys Lys Tyr Leu Asn Ser
 1               5

<210> SEQ ID NO 39
<211> LENGTH: 13
<212> TYPE: PRT
<213> ORGANISM: Homo sapiens

<400> SEQUENCE: 39

Arg Leu Arg Lys Gln Met Ala Val Lys Lys Tyr Leu Asn
 1               5                  10

<210> SEQ ID NO 40
<211> LENGTH: 12
```

```
<212> TYPE: PRT
<213> ORGANISM: Homo sapiens

<400> SEQUENCE: 40

Leu Arg Lys Gln Met Ala Val Lys Lys Tyr Leu Asn
 1               5                  10

<210> SEQ ID NO 41
<211> LENGTH: 11
<212> TYPE: PRT
<213> ORGANISM: Homo sapiens

<400> SEQUENCE: 41

Arg Lys Gln Met Ala Val Lys Lys Tyr Leu Asn
 1               5                  10

<210> SEQ ID NO 42
<211> LENGTH: 10
<212> TYPE: PRT
<213> ORGANISM: Homo sapiens

<400> SEQUENCE: 42

Lys Gln Met Ala Val Lys Lys Tyr Leu Asn
 1               5                  10

<210> SEQ ID NO 43
<211> LENGTH: 9
<212> TYPE: PRT
<213> ORGANISM: Homo sapiens

<400> SEQUENCE: 43

Gln Met Ala Val Lys Lys Tyr Leu Asn
 1               5

<210> SEQ ID NO 44
<211> LENGTH: 8
<212> TYPE: PRT
<213> ORGANISM: Homo sapiens

<400> SEQUENCE: 44

Met Ala Val Lys Lys Tyr Leu Asn
 1               5

<210> SEQ ID NO 45
<211> LENGTH: 7
<212> TYPE: PRT
<213> ORGANISM: Homo sapiens

<400> SEQUENCE: 45

Ala Val Lys Lys Tyr Leu Asn
 1               5

<210> SEQ ID NO 46
<211> LENGTH: 12
<212> TYPE: PRT
<213> ORGANISM: Homo sapiens

<400> SEQUENCE: 46

Arg Leu Arg Lys Gln Met Ala Val Lys Lys Tyr Leu
 1               5                  10

<210> SEQ ID NO 47
<211> LENGTH: 11
<212> TYPE: PRT
<213> ORGANISM: Homo sapiens
```

<400> SEQUENCE: 47

Leu Arg Lys Gln Met Ala Val Lys Lys Tyr Leu
 1               5                  10

<210> SEQ ID NO 48
<211> LENGTH: 10
<212> TYPE: PRT
<213> ORGANISM: Homo sapiens

<400> SEQUENCE: 48

Arg Lys Gln Met Ala Val Lys Lys Tyr Leu
 1               5                  10

<210> SEQ ID NO 49
<211> LENGTH: 9
<212> TYPE: PRT
<213> ORGANISM: Homo sapiens

<400> SEQUENCE: 49

Lys Gln Met Ala Val Lys Lys Tyr Leu
 1               5

<210> SEQ ID NO 50
<211> LENGTH: 8
<212> TYPE: PRT
<213> ORGANISM: Homo sapiens

<400> SEQUENCE: 50

Gln Met Ala Val Lys Lys Tyr Leu
 1               5

<210> SEQ ID NO 51
<211> LENGTH: 7
<212> TYPE: PRT
<213> ORGANISM: Homo sapiens

<400> SEQUENCE: 51

Met Ala Val Lys Lys Tyr Leu
 1               5

<210> SEQ ID NO 52
<211> LENGTH: 6
<212> TYPE: PRT
<213> ORGANISM: Homo sapiens

<400> SEQUENCE: 52

Ala Val Lys Lys Tyr Leu
 1               5

<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Phe Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

```
<210> SEQ ID NO 54
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ile Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 55
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 56
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

His Phe Asp Ala Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 57
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

His His Asp Ala Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 58
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

His Ile Asp Ala Val Phe Thr Asp Asn Tyr Thr Arg Leu Arg Lys Gln
```

```
                1               5              10              15
Met Ala Val Lys Lys Tyr Leu Asn Ser Ile Leu Asn
            20                  25
```

<210> SEQ ID NO 59
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

```
His Leu Asp Ala Val Phe Thr Asp Asn Tyr Thr Arg Leu Arg Lys Gln
  1               5                  10                  15
Met Ala Val Lys Lys Tyr Leu Asn Ser Ile Leu Asn
             20                  25
```

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
His Met Asp Ala Val Phe Thr Asp Asn Tyr Thr Arg Leu Arg Lys Gln
  1               5                  10                  15
Met Ala Val Lys Lys Tyr Leu Asn Ser Ile Leu Asn
             20                  25
```

<210> SEQ ID NO 61
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

```
His Gln Asp Ala Val Phe Thr Asp Asn Tyr Thr Arg Leu Arg Lys Gln
  1               5                  10                  15
Met Ala Val Lys Lys Tyr Leu Asn Ser Ile Leu Asn
             20                  25
```

<210> SEQ ID NO 62
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
His Thr Asp Ala Val Phe Thr Asp Asn Tyr Thr Arg Leu Arg Lys Gln
  1               5                  10                  15
Met Ala Val Lys Lys Tyr Leu Asn Ser Ile Leu Asn
             20                  25
```

<210> SEQ ID NO 63
<211> LENGTH: 28
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 63

His Val Asp Ala Val Phe Thr Asp Asn Tyr Thr Arg Leu Arg Lys Gln
  1               5                  10                  15

Met Ala Val Lys Lys Tyr Leu Asn Ser Ile Leu Asn
             20                  25

<210> SEQ ID NO 64
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

His Trp Asp Ala Val Phe Thr Asp Asn Tyr Thr Arg Leu Arg Lys Gln
  1               5                  10                  15

Met Ala Val Lys Lys Tyr Leu Asn Ser Ile Leu Asn
             20                  25

<210> SEQ ID NO 65
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

His Tyr Asp Ala Val Phe Thr Asp Asn Tyr Thr Arg Leu Arg Lys Gln
  1               5                  10                  15

Met Ala Val Lys Lys Tyr Leu Asn Ser Ile Leu Asn
             20                  25

<210> SEQ ID NO 66
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

His Ser Ala Ala Val Phe Thr Asp Asn Tyr Thr Arg Leu Arg Lys Gln
  1               5                  10                  15

Met Ala Val Lys Lys Tyr Leu Asn Ser Ile Leu Asn
             20                  25

<210> SEQ ID NO 67
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

His Ser Glu Ala Val Phe Thr Asp Asn Tyr Thr Arg Leu Arg Lys Gln
  1               5                  10                  15

Met Ala Val Lys Lys Tyr Leu Asn Ser Ile Leu Asn
             20                  25
```

<210> SEQ ID NO 68
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

His Ser Phe Ala Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 69
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

His Ser His Ala Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 70
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

His Ser Ile Ala Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 71
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

His Ser Leu Ala Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 72
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

His Ser Met Ala Val Phe Thr Asp Asn Tyr Thr Arg Leu Arg Lys Gln
 1               5                  10                  15

Met Ala Val Lys Lys Tyr Leu Asn Ser Ile Leu Asn
             20                  25

<210> SEQ ID NO 73
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

His Ser Trp Ala Val Phe Thr Asp Asn Tyr Thr Arg Leu Arg Lys Gln
 1               5                  10                  15

Met Ala Val Lys Lys Tyr Leu Asn Ser Ile Leu Asn
             20                  25

<210> SEQ ID NO 74
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

His Ser Asp Phe Val Phe Thr Asp Asn Tyr Thr Arg Leu Arg Lys Gln
 1               5                  10                  15

Met Ala Val Lys Lys Tyr Leu Asn Ser Ile Leu Asn
             20                  25

<210> SEQ ID NO 75
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

His Ser Asp Gly Val Phe Thr Asp Asn Tyr Thr Arg Leu Arg Lys Gln
 1               5                  10                  15

Met Ala Val Lys Lys Tyr Leu Asn Ser Ile Leu Asn
             20                  25

<210> SEQ ID NO 76
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

His Ser Asp Met Val Phe Thr Asp Asn Tyr Thr Arg Leu Arg Lys Gln
 1               5                  10                  15

Met Ala Val Lys Lys Tyr Leu Asn Ser Ile Leu Asn
             20                  25

<210> SEQ ID NO 77
<211> LENGTH: 28
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 77

His Ser Asp Gln Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 78
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

His Ser Asp Ser Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 79
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

His Ser Asp Trp Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 80
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

His Ser Asp Tyr Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 81
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

His Ser Asp Ala Phe Phe Thr Asp Asn Tyr Thr Arg Leu Arg Lys Gln
 1               5                  10                  15

Met Ala Val Lys Lys Tyr Leu Asn Ser Ile Leu Asn
            20                  25
```

<210> SEQ ID NO 82
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

His Ser Asp Ala Ile Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 83
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

His Ser Asp Ala Leu Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 84
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

His Ser Asp Ala Met Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 85
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

His Ser Asp Ala Thr Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 86
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

His Ser Asp Ala Trp Phe Thr Asp Asn Tyr Thr Arg Leu Arg Lys Gln
 1               5                   10                  15

Met Ala Val Lys Lys Tyr Leu Asn Ser Ile Leu Asn
            20                  25

<210> SEQ ID NO 87
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

His Ser Asp Ala Tyr Phe Thr Asp Asn Tyr Thr Arg Leu Arg Lys Gln
 1               5                   10                  15

Met Ala Val Lys Lys Tyr Leu Asn Ser Ile Leu Asn
            20                  25

<210> SEQ ID NO 88
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

His Ser Asp Ala Val Lys Thr Asp Asn Tyr Thr Arg Leu Arg Lys Gln
 1               5                   10                  15

Met Ala Val Lys Lys Tyr Leu Asn Ser Ile Leu Asn
            20                  25

<210> SEQ ID NO 89
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

His Ser Asp Ala Val Phe Val Asp Asn Tyr Thr Arg Leu Arg Lys Gln
 1               5                   10                  15

Met Ala Val Lys Lys Tyr Leu Asn Ser Ile Leu Asn
            20                  25

<210> SEQ ID NO 90
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

His Ser Asp Ala Val Phe Trp Asp Asn Tyr Thr Arg Leu Arg Lys Gln
 1               5                   10                  15

Met Ala Val Lys Lys Tyr Leu Asn Ser Ile Leu Asn
            20                  25

<210> SEQ ID NO 91
<211> LENGTH: 28
<212> TYPE: PRT

-continued

<213> ORGANISM: Artificial Sequence
<220> FEATURE:
<223> OTHER INFORMATION: Description of Artificial Sequence: Synthetic
      peptide

<400> SEQUENCE: 91

His Ser Asp Ala Val Phe Thr Asp Asn Trp Thr Arg Leu Arg Lys Gln
 1               5                  10                  15

Met Ala Val Lys Lys Tyr Leu Asn Ser Ile Leu Asn
            20                  25

<210> SEQ ID NO 92
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

His Ser Asp Ala Val Phe Thr Asp Asn Tyr Thr Arg Arg Arg Lys Gln
 1               5                  10                  15

Met Ala Val Lys Lys Tyr Leu Asn Ser Ile Leu Asn
            20                  25

<210> SEQ ID NO 93
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

His Ser Asp Ala Val Phe Thr Asp Asn Tyr Thr Arg Trp Arg Lys Gln
 1               5                  10                  15

Met Ala Val Lys Lys Tyr Leu Asn Ser Ile Leu Asn
            20                  25

<210> SEQ ID NO 94
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

His Ser Asp Ala Val Phe Thr Asp Asn Tyr Thr Arg Leu Arg Phe Gln
 1               5                  10                  15

Met Ala Val Lys Lys Tyr Leu Asn Ser Ile Leu Asn
            20                  25

<210> SEQ ID NO 95
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

His Ser Asp Ala Val Phe Thr Asp Asn Tyr Thr Arg Leu Arg Leu Gln
 1               5                  10                  15

Met Ala Val Lys Lys Tyr Leu Asn Ser Ile Leu Asn

-continued

```
                20                  25

<210> SEQ ID NO 96
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

His Ser Asp Ala Val Phe Thr Asp Asn Tyr Thr Arg Leu Arg Met Gln
  1               5                  10                  15

Met Ala Val Lys Lys Tyr Leu Asn Ser Ile Leu Asn
                20                  25

<210> SEQ ID NO 97
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

His Ser Asp Ala Val Phe Thr Asp Asn Tyr Thr Arg Leu Arg Arg Gln
  1               5                  10                  15

Met Ala Val Lys Lys Tyr Leu Asn Ser Ile Leu Asn
                20                  25

<210> SEQ ID NO 98
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

His Ser Asp Ala Val Phe Thr Asp Asn Tyr Thr Arg Leu Arg Lys Ala
  1               5                  10                  15

Met Ala Val Lys Lys Tyr Leu Asn Ser Ile Leu Asn
                20                  25

<210> SEQ ID NO 99
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

His Ser Asp Ala Val Phe Thr Asp Asn Tyr Thr Arg Leu Arg Lys Phe
  1               5                  10                  15

Met Ala Val Lys Lys Tyr Leu Asn Ser Ile Leu Asn
                20                  25

<210> SEQ ID NO 100
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 100

His Ser Asp Ala Val Phe Thr Asp Asn Tyr Thr Arg Leu Arg Lys Ile
 1               5                  10                  15

Met Ala Val Lys Lys Tyr Leu Asn Ser Ile Leu Asn
            20                  25

<210> SEQ ID NO 101
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

His Ser Asp Ala Val Phe Thr Asp Asn Tyr Thr Arg Leu Arg Lys Lys
 1               5                  10                  15

Met Ala Val Lys Lys Tyr Leu Asn Ser Ile Leu Asn
            20                  25

<210> SEQ ID NO 102
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

His Ser Asp Ala Val Phe Thr Asp Asn Tyr Thr Arg Leu Arg Lys Leu
 1               5                  10                  15

Met Ala Val Lys Lys Tyr Leu Asn Ser Ile Leu Asn
            20                  25

<210> SEQ ID NO 103
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

His Ser Asp Ala Val Phe Thr Asp Asn Tyr Thr Arg Leu Arg Lys Met
 1               5                  10                  15

Met Ala Val Lys Lys Tyr Leu Asn Ser Ile Leu Asn
            20                  25

<210> SEQ ID NO 104
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

His Ser Asp Ala Val Phe Thr Asp Asn Tyr Thr Arg Leu Arg Lys Arg
 1               5                  10                  15

Met Ala Val Lys Lys Tyr Leu Asn Ser Ile Leu Asn
            20                  25

<210> SEQ ID NO 105
<211> LENGTH: 28
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

His Ser Asp Ala Val Phe Thr Asp Asn Tyr Thr Arg Leu Arg Lys Val
  1               5                  10                  15

Met Ala Val Lys Lys Tyr Leu Asn Ser Ile Leu Asn
             20                  25

<210> SEQ ID NO 106
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

His Ser Asp Ala Val Phe Thr Asp Asn Tyr Thr Arg Leu Arg Lys Trp
  1               5                  10                  15

Met Ala Val Lys Lys Tyr Leu Asn Ser Ile Leu Asn
             20                  25

<210> SEQ ID NO 107
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

His Ser Asp Ala Val Phe Thr Asp Asn Tyr Thr Arg Leu Arg Lys Tyr
  1               5                  10                  15

Met Ala Val Lys Lys Tyr Leu Asn Ser Ile Leu Asn
             20                  25

<210> SEQ ID NO 108
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

His Ser Asp Ala Val Phe Thr Asp Asn Tyr Thr Arg Leu Arg Lys Gln
  1               5                  10                  15

Phe Ala Val Lys Lys Tyr Leu Asn Ser Ile Leu Asn
             20                  25

<210> SEQ ID NO 109
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

His Ser Asp Ala Val Phe Thr Asp Asn Tyr Thr Arg Leu Arg Lys Gln
  1               5                  10                  15
```

```
Ile Ala Val Lys Lys Tyr Leu Asn Ser Ile Leu Asn
            20                  25
```

<210> SEQ ID NO 110
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

```
His Ser Asp Ala Val Phe Thr Asp Asn Tyr Thr Arg Leu Arg Lys Gln
 1               5                  10                  15
Lys Ala Val Lys Lys Tyr Leu Asn Ser Ile Leu Asn
            20                  25
```

<210> SEQ ID NO 111
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

```
His Ser Asp Ala Val Phe Thr Asp Asn Tyr Thr Arg Leu Arg Lys Gln
 1               5                  10                  15
Leu Ala Val Lys Lys Tyr Leu Asn Ser Ile Leu Asn
            20                  25
```

<210> SEQ ID NO 112
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

```
His Ser Asp Ala Val Phe Thr Asp Asn Tyr Thr Arg Leu Arg Lys Gln
 1               5                  10                  15
Gln Ala Val Lys Lys Tyr Leu Asn Ser Ile Leu Asn
            20                  25
```

<210> SEQ ID NO 113
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

```
His Ser Asp Ala Val Phe Thr Asp Asn Tyr Thr Arg Leu Arg Lys Gln
 1               5                  10                  15
Arg Ala Val Lys Lys Tyr Leu Asn Ser Ile Leu Asn
            20                  25
```

<210> SEQ ID NO 114
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 114

His Ser Asp Ala Val Phe Thr Asp Asn Tyr Thr Arg Leu Arg Lys Gln
  1               5                  10                  15

Trp Ala Val Lys Lys Tyr Leu Asn Ser Ile Leu Asn
             20                  25

<210> SEQ ID NO 115
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

His Ser Asp Ala Val Phe Thr Asp Asn Tyr Thr Arg Leu Arg Lys Gln
  1               5                  10                  15

Met Phe Val Lys Lys Tyr Leu Asn Ser Ile Leu Asn
             20                  25

<210> SEQ ID NO 116
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

His Ser Asp Ala Val Phe Thr Asp Asn Tyr Thr Arg Leu Arg Lys Gln
  1               5                  10                  15

Met Ile Val Lys Lys Tyr Leu Asn Ser Ile Leu Asn
             20                  25

<210> SEQ ID NO 117
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

His Ser Asp Ala Val Phe Thr Asp Asn Tyr Thr Arg Leu Arg Lys Gln
  1               5                  10                  15

Met Lys Val Lys Lys Tyr Leu Asn Ser Ile Leu Asn
             20                  25

<210> SEQ ID NO 118
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

His Ser Asp Ala Val Phe Thr Asp Asn Tyr Thr Arg Leu Arg Lys Gln
  1               5                  10                  15

Met Leu Val Lys Lys Tyr Leu Asn Ser Ile Leu Asn
             20                  25

<210> SEQ ID NO 119
```

```
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

His Ser Asp Ala Val Phe Thr Asp Asn Tyr Thr Arg Leu Arg Lys Gln
 1               5                  10                  15

Met Met Val Lys Lys Tyr Leu Asn Ser Ile Leu Asn
            20                  25

<210> SEQ ID NO 120
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

His Ser Asp Ala Val Phe Thr Asp Asn Tyr Thr Arg Leu Arg Lys Gln
 1               5                  10                  15

Met Gln Val Lys Lys Tyr Leu Asn Ser Ile Leu Asn
            20                  25

<210> SEQ ID NO 121
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

His Ser Asp Ala Val Phe Thr Asp Asn Tyr Thr Arg Leu Arg Lys Gln
 1               5                  10                  15

Met Arg Val Lys Lys Tyr Leu Asn Ser Ile Leu Asn
            20                  25

<210> SEQ ID NO 122
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

His Ser Asp Ala Val Phe Thr Asp Asn Tyr Thr Arg Leu Arg Lys Gln
 1               5                  10                  15

Met Val Lys Lys Tyr Leu Asn Ser Ile Leu Asn
            20                  25

<210> SEQ ID NO 123
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

His Ser Asp Ala Val Phe Thr Asp Asn Tyr Thr Arg Leu Arg Lys Gln
 1               5                  10                  15
```

```
Met Trp Val Lys Lys Tyr Leu Asn Ser Ile Leu Asn
            20                  25
```

<210> SEQ ID NO 124
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

```
His Ser Asp Ala Val Phe Thr Asp Asn Tyr Thr Arg Leu Arg Lys Gln
 1               5                  10                  15

Met Tyr Val Lys Lys Tyr Leu Asn Ser Ile Leu Asn
            20                  25
```

<210> SEQ ID NO 125
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

```
His Ser Asp Ala Val Phe Thr Asp Asn Tyr Thr Arg Leu Arg Lys Gln
 1               5                  10                  15

Met Ala Ala Lys Lys Tyr Leu Asn Ser Ile Leu Asn
            20                  25
```

<210> SEQ ID NO 126
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

```
His Ser Asp Ala Val Phe Thr Asp Asn Tyr Thr Arg Leu Arg Lys Gln
 1               5                  10                  15

Met Ala Ile Lys Lys Tyr Leu Asn Ser Ile Leu Asn
            20                  25
```

<210> SEQ ID NO 127
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

```
His Ser Asp Ala Val Phe Thr Asp Asn Tyr Thr Arg Leu Arg Lys Gln
 1               5                  10                  15

Met Ala Leu Lys Lys Tyr Leu Asn Ser Ile Leu Asn
            20                  25
```

<210> SEQ ID NO 128
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 128

His Ser Asp Ala Val Phe Thr Asp Asn Tyr Thr Arg Leu Arg Lys Gln
1               5                   10                  15

Met Ala Val Arg Lys Tyr Leu Asn Ser Ile Leu Asn
            20                  25

<210> SEQ ID NO 129
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

His Ser Asp Ala Val Phe Thr Asp Asn Tyr Thr Arg Leu Arg Lys Gln
1               5                   10                  15

Met Ala Val Lys Arg Tyr Leu Asn Ser Ile Leu Asn
            20                  25

<210> SEQ ID NO 130
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

His Ser Asp Ala Val Phe Thr Asp Asn Tyr Thr Arg Leu Arg Lys Gln
1               5                   10                  15

Met Ala Val Lys Trp Tyr Leu Asn Ser Ile Leu Asn
            20                  25

<210> SEQ ID NO 131
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

His Ser Asp Ala Val Phe Thr Asp Asn Tyr Thr Arg Leu Arg Lys Gln
1               5                   10                  15

Met Ala Val Lys Lys Phe Leu Asn Ser Ile Leu Asn
            20                  25

<210> SEQ ID NO 132
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

His Ser Asp Ala Val Phe Thr Asp Asn Tyr Thr Arg Leu Arg Lys Gln
1               5                   10                  15

Met Ala Val Lys Lys Trp Leu Asn Ser Ile Leu Asn
            20                  25

<210> SEQ ID NO 133
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 133

His Ser Asp Ala Val Phe Thr Asp Asn Tyr Thr Arg Leu Arg Lys Gln
 1               5                  10                  15

Met Ala Val Lys Lys Tyr Leu Ala Ser Ile Leu Asn
            20                  25

<210> SEQ ID NO 134
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 134

His Ser Asp Ala Val Phe Thr Asp Asn Tyr Thr Arg Leu Arg Lys Gln
 1               5                  10                  15

Met Ala Val Lys Lys Tyr Leu Phe Ser Ile Leu Asn
            20                  25

<210> SEQ ID NO 135
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 135

His Ser Asp Ala Val Phe Thr Asp Asn Tyr Thr Arg Leu Arg Lys Gln
 1               5                  10                  15

Met Ala Val Lys Lys Tyr Leu Ile Ser Ile Leu Asn
            20                  25

<210> SEQ ID NO 136
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 136

His Ser Asp Ala Val Phe Thr Asp Asn Tyr Thr Arg Leu Arg Lys Gln
 1               5                  10                  15

Met Ala Val Lys Lys Tyr Leu Met Ser Ile Leu Asn
            20                  25

<210> SEQ ID NO 137
<211> LENGTH: 28
<212> TYPE: PRT
<213> ORGANISM: Artificial Sequence
<220> FEATURE:
<223> OTHER INFORMATION: Description of Artificial Sequence: Synthetic peptide

<400> SEQUENCE: 137

His Ser Asp Ala Val Phe Thr Asp Asn Tyr Thr Arg Leu Arg Lys Gln

```
                1               5                  10                 15
Met Ala Val Lys Lys Tyr Leu Ser Ser Ile Leu Asn
                20                 25
```

<210> SEQ ID NO 138
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

```
His Ser Asp Ala Val Phe Thr Asp Asn Tyr Thr Arg Leu Arg Lys Gln
 1               5                  10                 15
Met Ala Val Lys Lys Tyr Leu Val Ser Ile Leu Asn
                20                 25
```

<210> SEQ ID NO 139
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

```
His Ser Asp Ala Val Phe Thr Asp Asn Tyr Thr Arg Leu Arg Lys Gln
 1               5                  10                 15
Met Ala Val Lys Lys Tyr Leu Trp Ser Ile Leu Asn
                20                 25
```

<210> SEQ ID NO 140
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

```
His Ser Asp Ala Val Phe Thr Asp Asn Tyr Thr Arg Leu Arg Lys Gln
 1               5                  10                 15
Met Ala Val Lys Lys Tyr Leu Asn Asn Ile Leu Asn
                20                 25
```

<210> SEQ ID NO 141
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

```
His Ser Asp Ala Val Phe Thr Asp Asn Tyr Thr Arg Leu Arg Lys Gln
 1               5                  10                 15
Met Ala Val Lys Lys Tyr Leu Asn Arg Ile Leu Asn
                20                 25
```

<210> SEQ ID NO 142
<211> LENGTH: 28
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 142

His Ser Asp Ala Val Phe Thr Asp Asn Tyr Thr Arg Leu Arg Lys Gln
  1               5                  10                  15

Met Ala Val Lys Lys Tyr Leu Asn Trp Ile Leu Asn
             20                  25

<210> SEQ ID NO 143
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

His Ser Asp Ala Val Phe Thr Asp Asn Tyr Thr Arg Leu Arg Lys Gln
  1               5                  10                  15

Met Ala Val Lys Lys Tyr Leu Asn Tyr Ile Leu Asn
             20                  25

<210> SEQ ID NO 144
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

His Ser Asp Ala Val Phe Thr Asp Asn Tyr Thr Arg Leu Arg Lys Gln
  1               5                  10                  15

Met Ala Val Lys Lys Tyr Leu Asn Ser Leu Leu Asn
             20                  25

<210> SEQ ID NO 145
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

His Ser Asp Ala Val Phe Thr Asp Asn Tyr Thr Arg Leu Arg Lys Gln
  1               5                  10                  15

Met Ala Val Lys Lys Tyr Leu Asn Ser Ser Leu Asn
             20                  25

<210> SEQ ID NO 146
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

His Ser Asp Ala Val Phe Thr Asp Asn Tyr Thr Arg Leu Arg Lys Gln
  1               5                  10                  15

Met Ala Val Lys Lys Tyr Leu Asn Ser Trp Leu Asn
             20                  25

<210> SEQ ID NO 147
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

His Ser Asp Ala Val Phe Thr Asp Asn Tyr Thr Arg Leu Arg Lys Gln
 1               5                  10                  15

Met Ala Val Lys Lys Tyr Leu Asn Ser Tyr Leu Asn
            20                  25

<210> SEQ ID NO 148
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

His Ser Asp Ala Val Phe Thr Asp Asn Tyr Thr Arg Leu Arg Lys Gln
 1               5                  10                  15

Met Ala Val Lys Lys Tyr Leu Asn Ser Ile Phe Asn
            20                  25

<210> SEQ ID NO 149
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

His Ser Asp Ala Val Phe Thr Asp Asn Tyr Thr Arg Leu Arg Lys Gln
 1               5                  10                  15

Met Ala Val Lys Lys Tyr Leu Asn Ser Ile Ile Asn
            20                  25

<210> SEQ ID NO 150
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

His Ser Asp Ala Val Phe Thr Asp Asn Tyr Thr Arg Leu Arg Lys Gln
 1               5                  10                  15

Met Ala Val Lys Lys Tyr Leu Asn Ser Ile Trp Asn
            20                  25

<210> SEQ ID NO 151
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

```
His Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Trp
                20                  25
```

<210> SEQ ID NO 152
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (8)..(9)
<223> OTHER INFORMATION: any amino acid
<221> NAME/KEY: MOD_RES
<222> LOCATION: (11)
<223> OTHER INFORMATION: any amino acid

<400> SEQUENCE: 152

```
His Ser Asp Ala Val Phe Thr Xaa Xaa Tyr Xaa Arg Leu Arg Lys Gln
 1               5                  10                  15

Met Ala Val Lys Lys Tyr Leu Asn Ser Ile Leu Asn
                20                  25
```

<210> SEQ ID NO 153
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: can represent an amino acid or amino acid
      derivative that are not natural
<221> NAME/KEY: MOD_RES
<222> LOCATION: (6)
<223> OTHER INFORMATION: can represent an amino acid or amino acid
      derivatives that are not natural
<221> NAME/KEY: MOD_RES
<222> LOCATION: (10)
<223> OTHER INFORMATION: can represent an amino acid or amino acid
      derivatives that are not natural
<221> NAME/KEY: MOD_RES
<222> LOCATION: (22)
<223> OTHER INFORMATION: can represent an amino acid or amino acid
      derivatives that are not natural

<400> SEQUENCE: 153

```
Xaa Ser Asp Ala Val Xaa Thr Asp Asn Xaa Thr Arg Leu Arg Lys Gln
 1               5                  10                  15

Met Ala Val Lys Lys Xaa Leu Asn Ser Ile Leu Asn
                20                  25
```

<210> SEQ ID NO 154
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

```
Cys Lys Asn Phe Phe Trp Lys Thr Phe Thr Ser Cys
 1               5                  10
```

<210> SEQ ID NO 155
<211> LENGTH: 8

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Phe Phe Tyr Trp Lys Val Phe Thr
 1               5

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Phe Cys Phe Trp Lys Val Cys Thr
 1               5

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Phe Cys Tyr Trp Lys Val Cys Thr
 1               5

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Phe Cys Phe Trp Lys Thr Cys Thr
 1               5

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Phe Cys Tyr Trp Lys Thr Cys Thr
 1               5

<210> SEQ ID NO 160
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (6)
<223> OTHER INFORMATION: Abu
```

```
<400> SEQUENCE: 160

Phe Cys Tyr Trp Lys Xaa Cys
 1               5

<210> SEQ ID NO 161
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: pGlu

<400> SEQUENCE: 161

Glu Leu Tyr Gln Asn Lys Pro Arg Arg Pro Tyr Ile Leu
 1               5                  10

<210> SEQ ID NO 162
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Glu Leu Tyr Gln Asn Lys Pro Arg Arg Pro Tyr Ile Leu
 1               5                  10

<210> SEQ ID NO 163
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Glu Leu Tyr Glu Asn Lys Pro Arg Arg Pro Phe Ile Leu
 1               5                  10

<210> SEQ ID NO 164
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Glu Leu Tyr Glu Asn Lys Pro Arg Arg Pro Phe Ile Leu
 1               5                  10

<210> SEQ ID NO 165
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Glu Leu Tyr Gln Asn Lys Pro Arg Arg Pro Phe Ile Leu
 1               5                  10
```

```
<210> SEQ ID NO 166
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Glu Leu Tyr Gln Asn Lys Pro Arg Arg Pro Phe Ile Leu
 1               5                  10

<210> SEQ ID NO 167
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Glu Leu Tyr Glu Asn Lys Pro Arg Arg Pro Trp Ile Leu
 1               5                  10

<210> SEQ ID NO 168
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Glu Leu Tyr Glu Asn Lys Pro Arg Arg Pro Trp Ile Leu
 1               5                  10

<210> SEQ ID NO 169
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Glu Leu Tyr Gln Asn Lys Pro Arg Arg Pro Trp Ile Leu
 1               5                  10

<210> SEQ ID NO 170
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Glu Leu Tyr Gln Asn Lys Pro Arg Arg Pro Trp Ile Leu
 1               5                  10

<210> SEQ ID NO 171
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171
```

```
Glu Leu Tyr Glu Asn Lys Pro Arg Arg Pro Tyr Ile
 1               5                  10

<210> SEQ ID NO 172
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Glu Leu Tyr Glu Asn Lys Pro Arg Arg Pro Tyr
 1               5                  10

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Glu Leu Tyr Glu Asn Lys Pro Arg Arg Pro
 1               5                  10

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Glu Leu Tyr Glu Asn Lys Pro Arg Arg
 1               5

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Glu Leu Tyr Glu Asn Lys Pro Arg
 1               5

<210> SEQ ID NO 176
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Glu Leu Tyr Glu Asn Lys Pro
 1               5

<210> SEQ ID NO 177
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 177

Asn Lys Pro Arg Arg Pro Tyr Ile Leu
  1               5

<210> SEQ ID NO 178
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Lys Pro Arg Arg Pro Tyr Ile Leu
  1               5

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Pro Arg Arg Pro Tyr Ile Leu
  1               5

<210> SEQ ID NO 180
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Arg Arg Pro Tyr Ile Leu
  1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Asn Lys Pro Arg Arg Pro Phe Ile Leu
  1               5

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Lys Pro Arg Arg Pro Phe Ile Leu
  1               5
```

```
<210> SEQ ID NO 183
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Pro Arg Arg Pro Phe Ile Leu
  1               5

<210> SEQ ID NO 184
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Arg Arg Pro Phe Ile Leu
  1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Asn Lys Pro Arg Arg Pro Trp Ile Leu
  1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Lys Pro Arg Arg Pro Trp Ile Leu
  1               5

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Pro Arg Arg Pro Trp Ile Leu
  1               5

<210> SEQ ID NO 188
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 188

Arg Arg Pro Trp Ile Leu
  1               5

<210> SEQ ID NO 189
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (17)
<223> OTHER INFORMATION: Indotricarbocyanine Cys

<400> SEQUENCE: 189

His Ser Asp Ala Val Phe Thr Asp Asn Tyr Thr Arg Leu Arg Lys Gln
  1               5                  10                  15

Cys Ala Val Lys Lys Tyr Leu Asn Ser Ile Leu Asn
             20                  25

<210> SEQ ID NO 190
<211> LENGTH: 11
<212> TYPE: PRT
<213> ORGANISM: Homo sapiens

<400> SEQUENCE: 190

Arg Lys Gln Met Ala Val Lys Lys Tyr Leu Asn
  1               5                  10

<210> SEQ ID NO 191
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Arg Lys Gln Met Ala Val Lys Lys Tyr Leu Asn Lys
  1               5                  10

<210> SEQ ID NO 192
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Arg Lys Gln Met Ala Val Lys Lys Tyr Leu Asn
  1               5                  10

<210> SEQ ID NO 193
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Asn Leu Tyr Lys Lys Val Ala Met Gln Lys Arg
  1               5                  10
```

```
<210> SEQ ID NO 194
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Asn Lys Pro Arg Arg Pro Tyr Ile Leu Cys
 1               5                  10

<210> SEQ ID NO 195
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Cys Tyr Trp Lys Val Cys
 1               5

<210> SEQ ID NO 196
<211> LENGTH: 28
<212> TYPE: PRT
<213> ORGANISM: Homo sapiens

<400> SEQUENCE: 196

His Ser Asp Ala Val Phe Thr Asp Asn Tyr Thr Arg Leu Arg Lys Gln
 1               5                  10                  15

Met Ala Val Lys Lys Tyr Leu Asn Ser Ile Leu Asn
            20                  25
```

SHORT-CHAIN PEPTIDE-DYE CONJUGATES AS CONTRAST MEDIA FOR OPTICAL DIAGNOSIS

This application claims the benefit of the filing date of U.S. Provisional Application Ser. No. 60/128,785 filed Apr. 12, 1999.

The invention relates to compounds for tumor diagnosis that consist of conjugates of dyes with short-chain peptides, which are derived from vasco-active intestinal peptide, somatostatin or neurotensin, the use of these compounds as optical diagnostic agents, and diagnostic agents that contain these compounds.

On a cellular level, disease-induced alterations are often manifested as a receptor distribution or expression that is altered relative to the normal state. These differences can be both of quantitative type (e.g., the amount of transferrin receptors in proliferating cells) or else also of qualitative type (e.g., expression of vascular endothelial growth factors, VEGF). Previous attempts to image a pathological receptor expression or distribution have been noted mainly in radiodiagnosis because of the necessary sensitivity of the detection process.

Heptahelical receptors are target molecules of many pharmacological active ingredients (e.g., β-blockers, H2-acid blockers, antihistamines). In addition to therapeutic batches, mainly radiolabled, agonistic ligands of these receptors are used diagnostically for the so-called receptor scintigraphy for in-vivo detection and location of tumors. In this case, the mechanism of the receptor-mediated endocytosis is used, e.g., by the somatostatin receptor, which is more strongly expressed in neuroendocrine tumors. The somatostatin analog $^{111}$In-DTPA-pentetreotide (octreoscan$^{(R)}$) is clinically approved for routine scintigraphic diagnosis; literature: J. Steroid Biochem. Mol. Biol. 37, 1079–82, 1990, J. Nucl. Med. 32, 1184–9, 1991,; J. Nucl. Med. 33, 652–8, 1992; Digestion 3, 54–9, 1994, J. Clin. Invest. 93, 1321–5, 1994, Metabolism 45, 21–3, 1996.

Another batch consists in the use of radiolabeled VIP and VIP-analogs, which bind to the VIP-receptors. The VIP-receptor is more strongly expressed by a broad spectrum of tumors (i.a., adenocarcinomas).

WO 96/30055 describes radiodiagnostic and radiotherapeutic reagents, special VIP-receptor-binding peptides, which are radiolabeled and can be used for radiodiagnosis and radiotherapy. VIP-receptor-binding peptides that can be labeled with Tc-99m for scintigraphy are described especially advantageously. Additional literature: Cancer Research 54, 690–700, 1994; Endocrinology 136, 2662–80, 1994, J. Nucl. Med. 40, 353–361, 1999.

All described diagnosis batches that are based on the somatostatin receptor and VIP-receptor are radiodiagnostic batches (scintigraphy with $^{123}$I, $^{125}$I, $^{111}$In or $^{99m}$Tc-labeled peptides).

Literature: EP 588754, U.S. Pat. Nos. 5,650,134; 5,620, 675, 5,225,180; WO 96/23527; J. Steroid Biochem. Mol. Biol. 37, 1083–87, 1990; Lancet 242–4, 1989, J. Nucl. Med. 39, 1913–17, 1998.

No fluorescence-labeled peptides that are conjugated with dyes that make possible an in-vivo-fluorescence detection of tumors are known to date, however (Photochem. Photobiol. 68, 603–632, 1998).

DETAILED DESCRIPTION OF THE INVENTION

The object of the invention is to make available new compounds that make possible a sensitive diagnosis of tumors by detection of fluorescence radiation with use of a receptor-specific binding of the compounds to the target tissue. In this case, special dye molecules that are coupled to biomolecules are to yield a highly sensitive, detectable fluorescence signal.

The object is achieved by the provision of compounds that contain fluorescence dyes, which are coupled covalently to short-chain peptides. These conjugates have a high binding affinity to heptahelical receptors, especially the somatostatlin receptor, the VIP-receptor (vaso-active intestinal peptide), and the neurotensin receptor, and they are optionally taken up intracellularly by receptor-mediated endocytosis. The compounds according to the invention are therefore suitable for the technically simple, harmless optical diagnosis of tumor cells and tumor tissues, which increasingly express somatostatin receptors, VIP-receptors or neurotensin receptors in comparison to healthy cells. Especially suitable are the compounds for fluorescence diagnosis and especially advantageously for the fluorescence-endoscopic diagnosis in hollow organs, such as the esophagus, the cervix, the colon, and the bronchial tubes of various tumor types, such as, e.g. adenocarcinomas, neuroendocrine tumors or ductal pancreatic tumors.

Especially preferred dyes are distinguished in that they satisfy certain photophysical and chemical requirements. From the photophysical standpoint, the dyes must have high absorption coefficients and high fluorescence quantum yields to provide an effective signal even in the case of the smallest tissue concentrations. The absorption maxima must overlap a wide spectral range in a freely selectable manner. Thus, for detection in lower tissue layers (several centimeters below the surface), the spectral range of between 600 and 900 nm is essential, while for surface detection, absorption wavelengths of 400 to 600 nm are sufficient. From the chemical standpoint, the dyes must have a high photostability and must exhibit no signs of decomposition (photobleaching) during excitation. The dyes must be usable as synthesis components in the solid-phase-synthetic production of peptides and thus be stable under common synthesis conditions so that a simple, advantageous production of structurally defined dye-peptide-conjugates with solid stoichiometric ratios is ensured between dye and peptide. The requirements are best satisfied by polymethine dyes, especially cyanine, merocyanine, oxonol and squarilium dyes.

Subjects of the invention are therefore peptide-polymethine dye-conjugates of general formula (I)

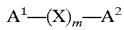

in which

X stands for an α-, β- or γ-amino acid with D- or L-configuration, and m stands for a number from 5 to 30, whereby the resulting amino acid sequence $(X)_m$ can be cyclized in a straight-chain nature or via a disulfide bridge between two cysteines or homocysteines or amidically between the N- and C-terminus and stands for the amino acid sequence of the vaso-active intestinal peptide (VIP), the somatostatin or the neurotensin, or for fragments, partial sequences, derivatives or analogs of the VIP, somatostatin or neurotensin, $A^1$ stands for a hydrogen atom, an acetyl radical or an alkyl radical with up to 10 C atoms, which optionally can be substituted with 1 to 3 carboxy groups and/or 1 to 6 hydroxy groups, or a poly(oxyethylene) radical with 2 to 30 —$CH_2CH_2O$ units, or a dye molecule from the class of the polymethine dyes, which has at least one absorption maximum in the range of 380 to 1200 nm, A² stands for a hydroxy group, an amino group or a dye molecule from the class of polymethine dyes, which has at least one absorption maximum in the range of 380 to 1200 nm, under the condition that at least one of radicals A¹ or A² represents a dye molecule from the class of polymethine dyes, which has at least one absorption maximum in the range of 380 to 1200 nm, whereby for the case that A¹ and/or A² represents a dye molecule from the class of polymethine dyes, which has at least one absorption maximum in the range of 380 to 1200 nm, A¹ is linked to the N-terminal amino group, and A² is linked to an amino group of the amino acid lysine or to a hydroxy group of the amino acid serine in any position within the amino acid sequence $(X)_m$, and their physiologically compatible salts.

Fragments, partial sequences, derivatives or analogs of the above-mentioned peptides stand, i.a., for shortened amino acid sequences, exchanges of individual or all amino acids for the corresponding D-amino acids, exchanges of individual amino acids for other amino acids, inverted sequences and combinations of the above-mentioned features.

The fragments, partial sequences, derivatives or analogs of the above-mentioned peptides can also contain amino acids that are not natural, such as, e.g., naphthalanine, cyclohexylalanine, norleucine, norvaline, α-aminoadipic acid, α-aminobutyric acid, β-alanine, β-cyclohexylalanine, ornithine, sarcosine or δ-hydroxylysine.

BRIEF DESCRIPTION OF THE DRAWINGS

FIG. 4 shows the photophysical properties of dye-peptide conjugates 14–38.

FIG. 7 shows the relative fluorescence intensities of RIN38VPAC1 cells after incubation in the presence of 150 nM of the dye-labeled peptides for 1 hour at 37° C. The data is expressed in percentage relative to the native peptide of the respective series.

Figure 1:
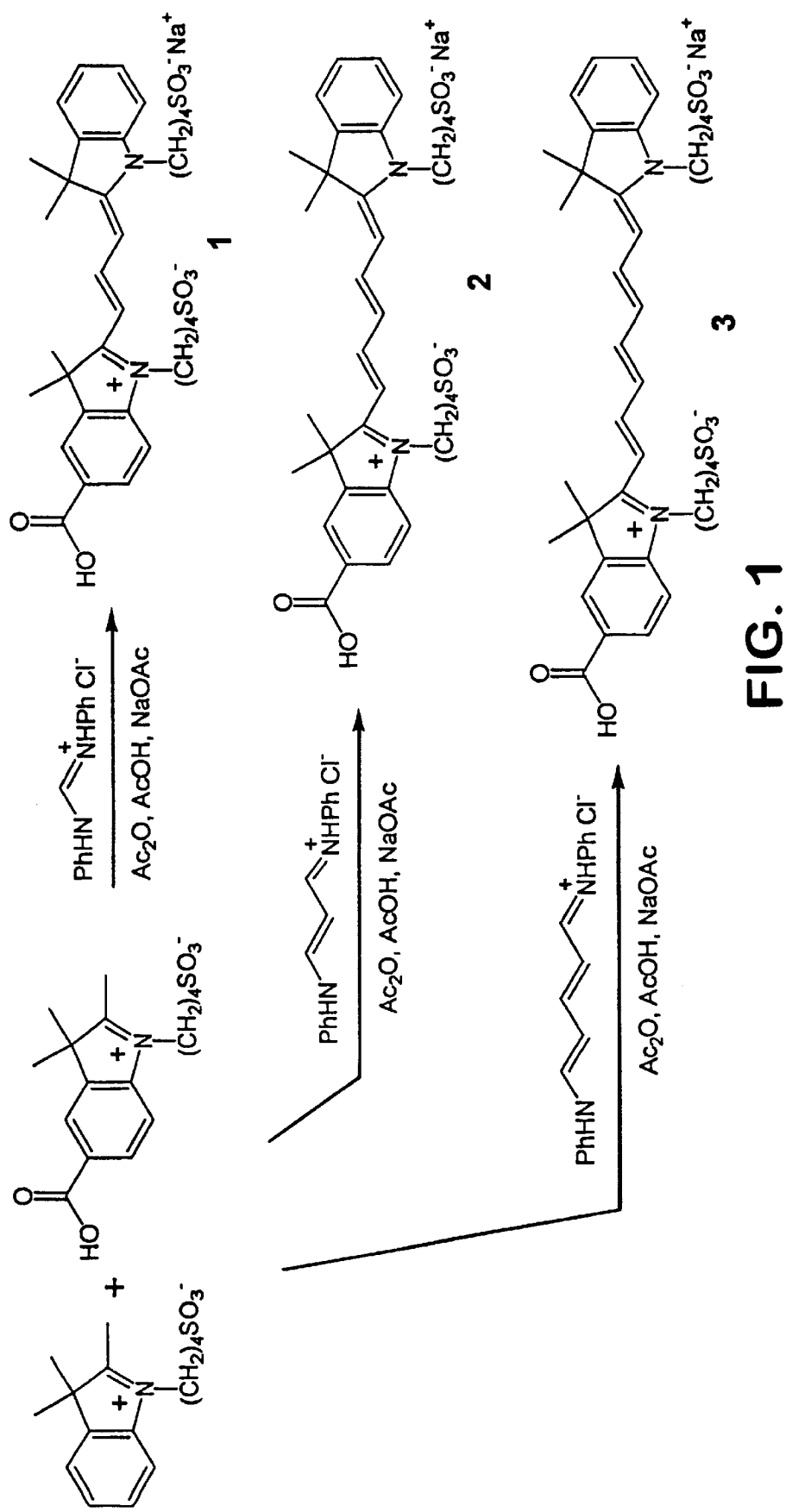
FIG. 1 shows the synthesis of: 1,1'-bis(4-sulfobutyl)indocarbocyanine-5-barboxylic acid, sodium salt (1); 1,1'-bis(4-sulfobutyl)indodicarbocyanine-5-barboxylic acid, sodium salt (2); and 1,1'-bis(4-sulfobutyl)indotricarbocyanine-5-barboxylic acid, sodium salt (3).
Figure 2:
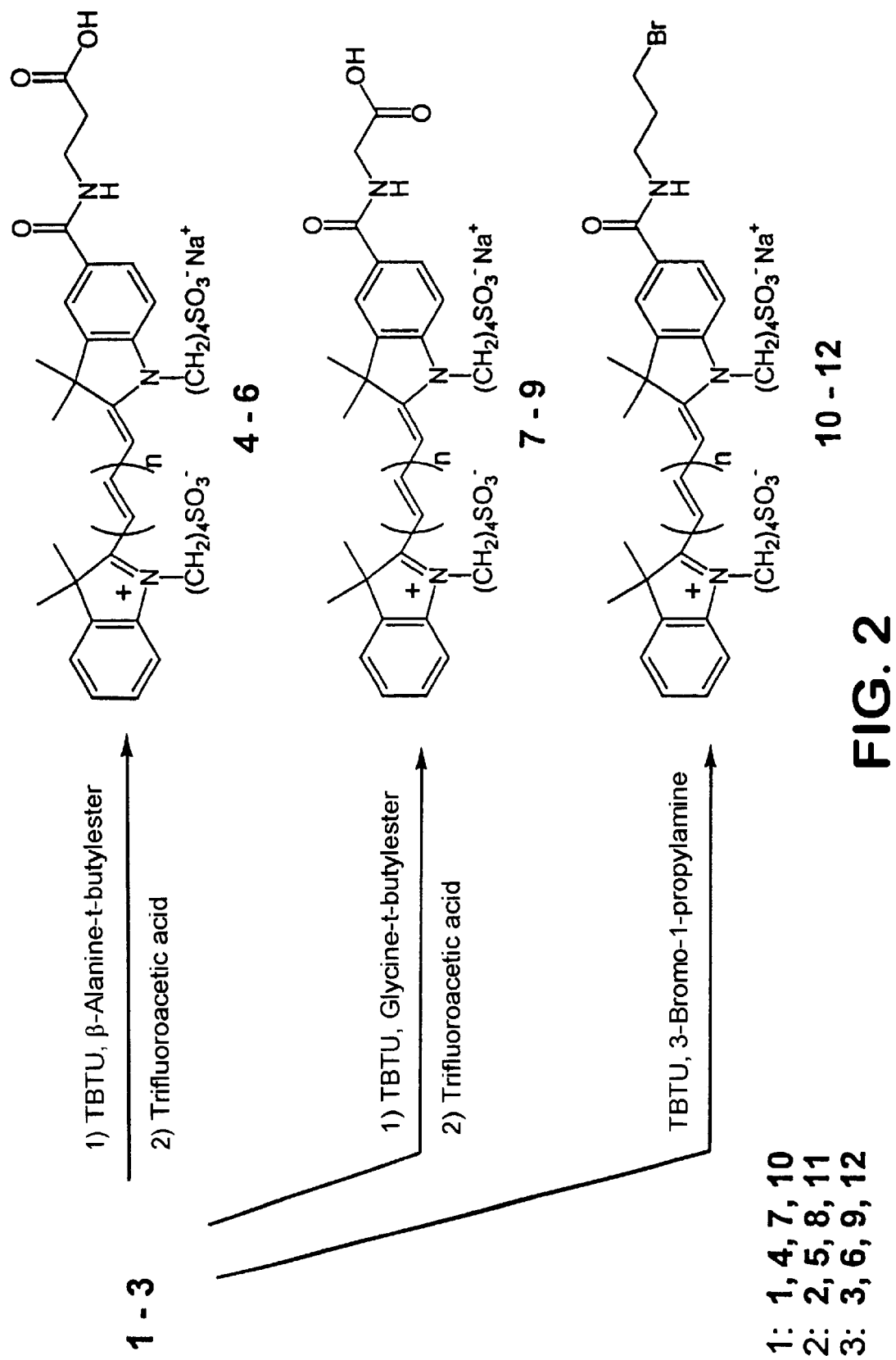
FIG. 2 shows the synthesis of indocyanine dyes 4–6, 7–9, and 10–12 from 1–3 solid-phase-synthetic coupling to amino groups (N-terminal or ε-lysine) of the peptides.
Figure 3:
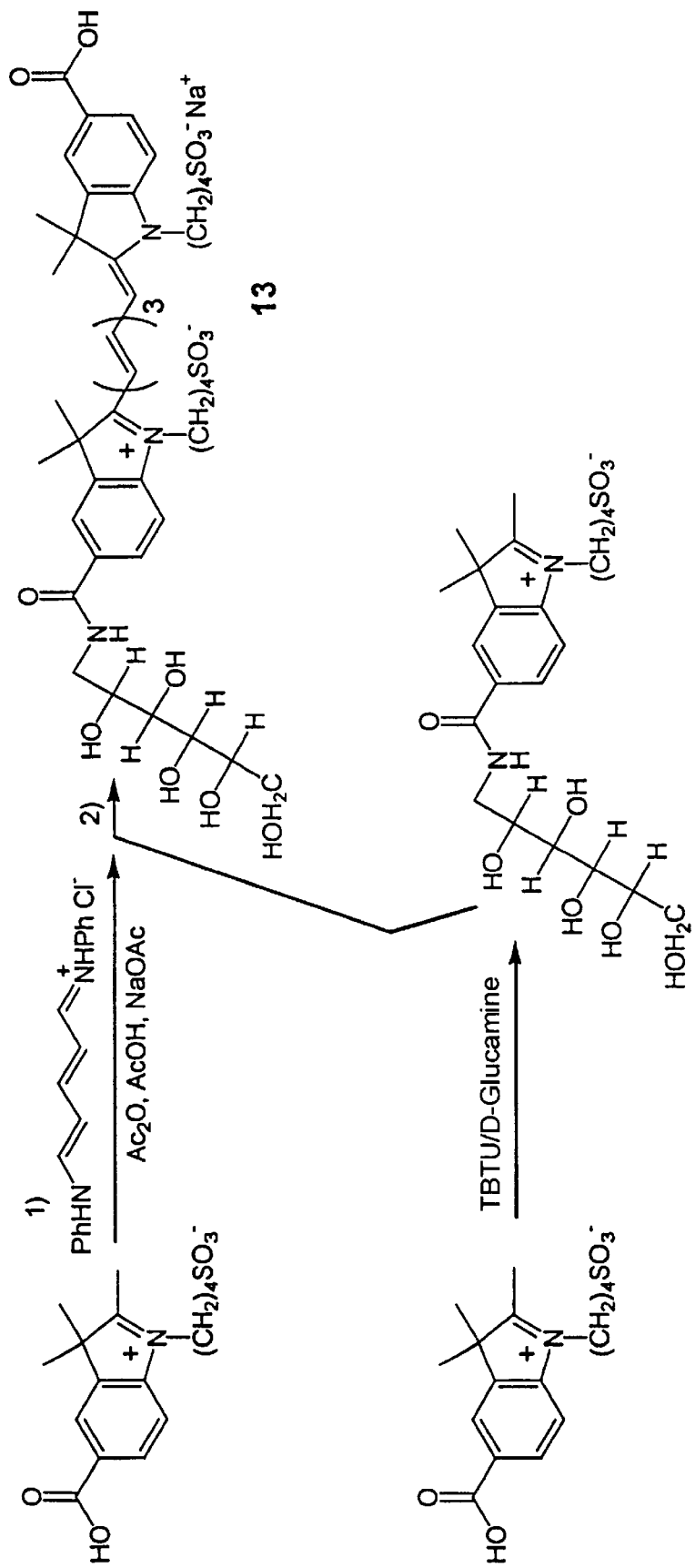
FIG. 3 shows the resin synthesis of peptide conjugates of VIP-receptor-binding peptides and dye 13.

Especially preferred embodiments of the invention are compounds of general formula I, which are distinguished in that dye molecule A¹ and/or A² stands for a cyanine, squarilium, croconium, merocyanine or oxonol dye. These dyes belong to the class of polymethine dyes and have the advantages that are described above.

Other preferred compounds of general formula I according to the invention are distinguished in that dye molecule A¹ and/or A² stands for a cyanine dye or squarilium dye of general formula II

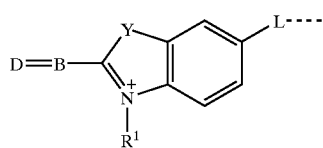

in which

D stands for a fragment corresponding to general formulas III to VI, whereby the position that is identified with a star means the linkage with B

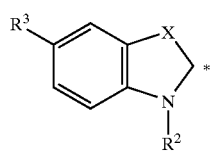

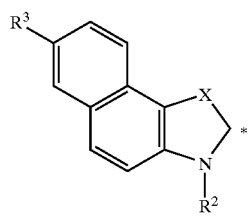

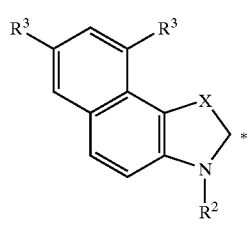

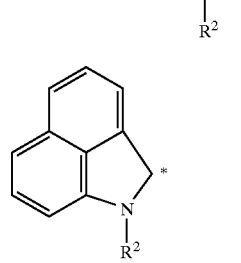

B stands for a fragment that corresponds to general formulas VII to XII

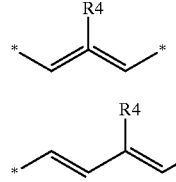

-continued

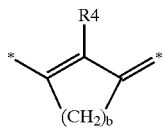

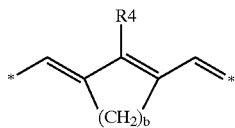

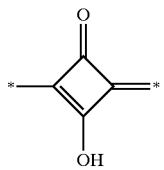

R¹ and R² stand for E¹, R³ stands for a fluorine, chlorine, bromine, iodine atom or a nitro group or for a radical —COOE¹, —CONE¹E², —NHCOE¹, —NICONHE¹, —NE¹E², —OE¹, —OSO₃E¹, —SO₃E¹, —SO₂NHE¹, —E¹, whereby E¹ and E², independently of one another, stand for a hydrogen atom, a $C_1$–$C_4$ sulfoalkyl chain, a saturated or unsaturated, branched or straight-chain $C_1$–$C_{50}$ alkyl chain, whereby the chain or parts of this chain optionally can form one or more aromatic or saturated cyclic $C_5$–$C_6$ units or bicyclic $C_{10}$ units, and whereby the $C_1$–$C_{50}$ alkyl chain is interrupted by 0 to 15 oxygen atoms and/or by 0 to 3 carbonyl groups and/or is substituted with 0 to 5 hydroxy groups, R⁴ stands for a hydrogen atom, for a fluorine, chlorine, bromine, iodine atom or a branched or straight-chain $C_1$–$C_{10}$ alkyl chain, b means a number 2 or 3, X and Y, independently of one another, mean O, S, Se, —CH=CH— or C(CH₃)₂, L stands for a group that corresponds to the formulas below

 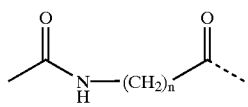

X

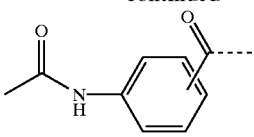

XI

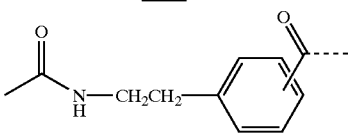

XII

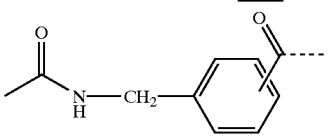

in which n means a number from 1 to 10.

(In the above-mentioned formulas, the solid line that is drawn to the left in the molecule portion represents the linkage to the dye skeleton, and the dashed line to the right in the molecule portion represents the linkage to the peptide.)

From the class of polymethine dyes, the cyanine dyes, e.g., the indocarbo-, indodicarbo- and indotricarbocyanines that are based on the indole structure, are especially advantageous. These structures are distinguished by a high chemical and photochemical stability. By advantageous synthesis, derivatives can be obtained that absorb and fluoresce between 400 and 1000 nm in any way desired, can be coupled to peptides by substitution with suitable linkers and functional groups, preferably carboxyl groups, and have a high water solubility, preferably by sulfonate groups. In contrast to cyanine dyes that are known in the literature, the compounds that are used according to the invention have only one reactive group, which makes possible a stoichiometrically defined coupling to the peptide as part of the resin synthesis of the conjugate.

Especially preferred embodiments of the compounds of general formula I according to the invention are therefore distinguished in that dye molecule A¹ and/or A² stands for an indocarbocyanine dye, an indodicarbocyanine dye or an indotricarbocyanine dye, dye molecule A¹ and/or A² stands for an indocarbocyanine dye, an indodicarbocyanine dye or an indotricarbocyanine dye of general formula XIII or XIV

XIII

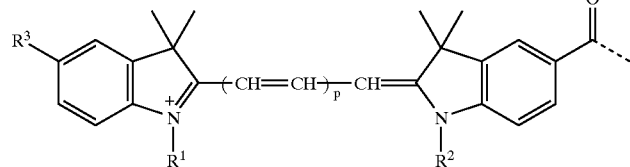

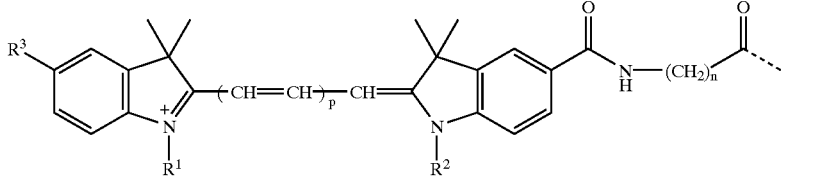

in which
p stands for 1, 2 or 3,
n stands for a number 1, 2, 3, 4 or 10,
$R^1$ and $R^2$, independently of one another, stand for a 4-sulfobutyl, 3-sulfopropyl, 2-sulfoethyl, 3-methyl-3-sulfopropyl, methyl, ethyl or propyl radical, and
$R^3$ stands for hydrogen, a chlorine, bromine, iodine atom or a nitro group or for a radical —$COOE^1$, —$CONE^1E^2$, —$NHCOE^1$, —$NHCONHE^1$, —$NE^1E^2$, —$OE^1$, —$OSO_3E^1$, —$SO_3E^1$, —$SO_2NHE^1$, whereby $E^1$ and $E_2$, independently of one another, stand for a hydrogen atom or for a methyl or ethyl radical or a $C_3$–$C_6$ alkyl radical, which is interrupted by 0 to 2 oxygen atoms and/or by 0 to 1 carbonyl groups, and/or is substituted with 0 to 5 hydroxy groups, or $E^1$ and $E^2$ stand for a poly (oxyethylene)glycol radical with 2 to 30 —$CH_2CH_2O$ units, dye molecule $A^1$ and/or $A^2$ stands for an indocarbocyanine dye, an indodicarbocyanine dye or an indotricarbocyanine dye of general formula XIII or XIV

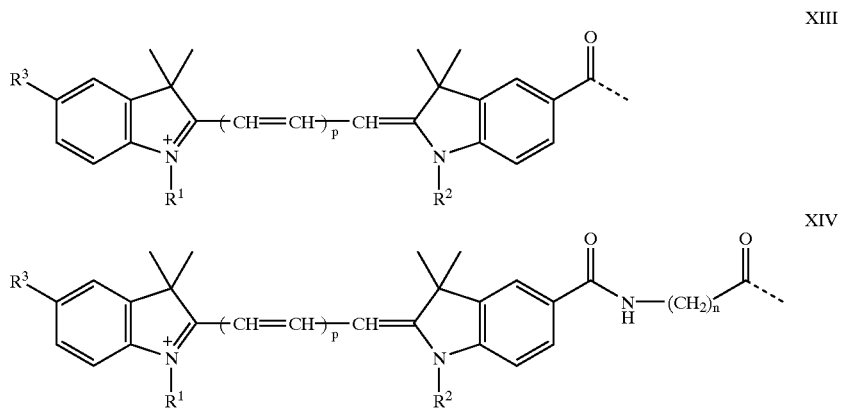

in which
p stands for 1, 2 or 3,
n stands for 1, 2 or 4,
$R^1$ and $R^2$, independently of one another, stand for a 4-sulfobutyl or 3-sulfopropyl radical,
$R^3$ stands for hydrogen or for a radical —$COOE^1$ or —$CONHE^1$,
whereby $E^1$ means a hydrogen atom or a methyl or ethyl radical or a $C_3$–$C_6$ alkyl radical, which is interrupted by 0 to 2 oxygen atoms and/or by 0 to 1 carbonyl groups and/or is substituted with 0 to 5 hydroxy groups,
dye molecule $A^1$ and/or $A^2$ stands for an indotricarbocyanine dye of general formula XV or XVI:

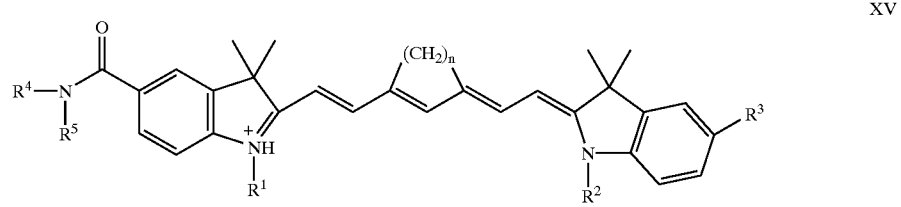

XVI

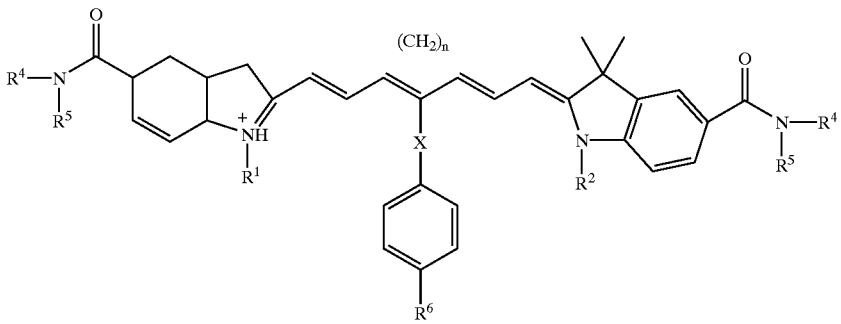

in which
n stands for 2 or 3,
$R^1$ and $R^2$, independently of one another, represent a 4-sulfobutyl, 3-sulfopropyl or 2-sulfoethyl radical,
$R^3$ stands for a radical —CONH-peptide, —CONH—$(CH_2)_m$—CONH peptide, —CONH—$(CH_2)_n$—NH—CS—NH-peptide or —CONH—$(CH_2)_n$—NHCO—$C_2$-peptide with m=1 to 10 and n=2 or 3, or $R^3$ represents a group below:

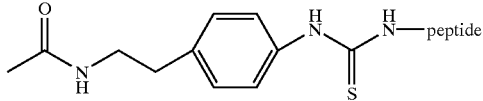

$R^4$ and $R^5$, independently of one another, stand for a hydrogen atom, a methyl radical or a hydroxylated alkyl radical, such as, e.g., 2-hydroxyethyl, 3-hydroxypropyl, 2,3-dihydroxypropyl, 1,3-dihydroxy-2-propyl, 2,3,4-trihydroxybutyl, 1,3,4-trihydroxy-2-butyl, 2,3,4,5,6-pentahydroxyhexyl,
$R^6$ stands for one of the following groups: —$(CH_2)_m$—CONH-peptide with m=0 to 2, —$(CH_2)_m$—NH—CS—NH-peptide with m=0 to 2,
and X stands for an oxygen atom or a sulfur atom;
dye molecule $A^1$ and/or $A^2$ stands for an indotricarbocyanine dye of general formula XVII:

NHCO—$C_2$-peptide with m=1 to 10 and n=2 or 3, or $R^3$ represents a group below:

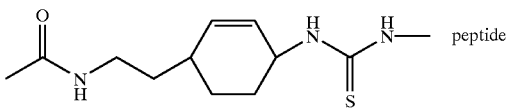

and $R^4$ and $R^5$, independently of one another, stand for a hydrogen atom, a methyl radical or a hydroxylated alkyl radical, such as, e.g., 2-hydroxyethyl, 3-hydroxypropyl, 2,3-dihydroxypropyl, 1,3-dihydroxy-2-propyl, 2,3,4-trihydroxybutyl, 1,3,4-trihydroxy-2-butyl, 2,3,4,5,6-pentahydroxyhexyl.

The use of dye-labeled antibodies for tumor detection is known in the literature (J. Cell. Pharmacol. 3, 141–145, 1992; Cancer Immunol. Immunother. 41, 257–63, 1995; Cancer Research 54, 2643–9, 1994, Biotechnol. Prog. 13, 649–658, 1997).

In contrast, the compounds according to the invention contain as biomolecules low-molecular peptides and peptide derivatives that exhibit the advantages of antibodies, such as a high binding to target structures, without the diagnostic potential being limited by an unfavorable pharmacokinetics (long blood half-lives, allergenic side-effects (immunogenicity)).

Biological and pharmacological requirements on peptide sequences are consequently an adequate plasma stability In the case of quick build-up in the target tissue and simulta-

XVII

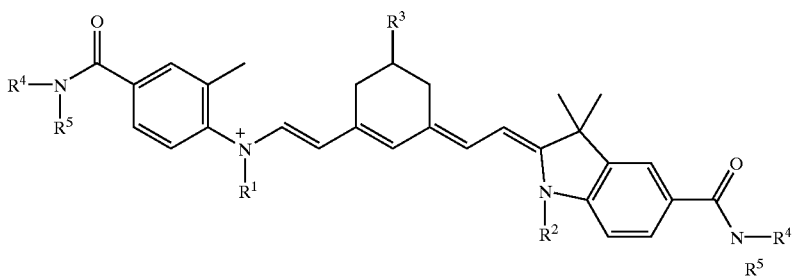

in which $R^1$ and $R^2$, independently of one another, stand for a 4-sulfobutyl radical or 3-sulfopropyl radical, $R^3$ stands for a radical —CONH-peptide, —CONH—$(CH_2)_m$—CONH-peptide, —CONH—$(CH_2)_n$—NH—CS—NH-peptide or —CONH—$(CH_2)_n$— neous quick elimination from the remainder of the body, preferably via the renal excretion route.

It has been found, surprisingly enough, that peptide sequences that contain at least 5 amino acids of the C-terminal side of the VIP-sequence and to which a dye is coupled for fluorescence diagnosis have an imaging in tumor cells that is comparable to the native VIP. Moreover, it has been found that by the incorporation of at least one D-amino acid, or the exchange by at least one D-amino acid, the plasma stability could be considerably increased. In the example of a complete exchange of all L-amino acids for D-amino acids in a VIP-binding dye-peptide conjugate, it was possible to show that the binding properties and the cell imaging are unchanged.

Other especially preferred compounds of general formula I according to the invention are distinguished in that (X)$_m$ stands for the amino acid sequence of the native, naturally occurring, human, vaso-active intestinal peptide corresponding to

HSDAVFTDNYTRLRKQMAVKKYLNSILN   (SEQ ID NO: 196)

or for fragments, partial sequences, derivatives or analogs of the vaso-active, intestinal peptide that consists of 5 to 30 amino acids, (X)$_m$ stands for the amino acid sequence of the somatostatin that corresponds to

AGCKNFFWKTFTSC   (SEQ ID NO: 9)

or for fragments, partial sequences, derivatives or analogs of the somatostatin that consists of 5 to 20 amino acids, (X)$_m$ stands for the amino acid sequence of the neurotensin that corresponds to pyroglutamic acid-LYENKPRRPYIL   (SEQ ID NO: 10)

or for fragments, partial sequences, derivatives or analogs of the neurotensin that consists of 5 to 20 amino acids, as fragments, partial sequences, derivatives or analogs of the vaso-active intestinal peptide (VIP), the following amino acid sequences are selected:

| | | |
|---|---|---|
| RLRKQMAVKKYLNSILN (SEQ ID NO: 11) | RLRKQMAVKKYLNSIL (SEQ ID NO: 18) | RLRKQMAVKKYLNSI (SEQ ID NO: 25) |
| LRKQMAVKKYLNSILN (SEQ ID NO: 12) | LRKQMAVKKYLNSIL (SEQ ID NO: 19) | LRKQMAVKKYLNSI (SEQ ID NO: 26) |
| RKQMAVKKYLNSILN (SEQ ID NO: 13) | RKQMAVKKYLNSIL (SEQ ID NO: 20) | RKQMAVKKYLNSI (SEQ ID NO: 27) |
| KQMAVKKYLNSILN (SEQ ID NO: 14) | KQMAVKKYLNSIL (SEQ ID NO: 21) | KQMAVKKYLNSI (SEQ ID NO: 28) |
| QMAVKKYLNSILN (SEQ ID NO: 15) | QMAVKKYLNSIL (SEQ ID NO: 22) | QMAVKKYLNSI (SEQ ID NO: 29) |
| MAVKKYLNSILN (SEQ ID NO: 16) | MAVKKYLNSIL (SEQ ID NO: 23) | MAVKKYLNSI (SEQ ID NO: 30) |
| AVKKYLNSILN (SEQ ID NO: 17) | AVKKYLNSIL (SEQ ID NO: 24) | AVKKYLNSI (SEQ ID NO: 31) |
| RLRKQMAVKKYLNS (SEQ ID NO: 32) | RLRKQMAVKKYLN (SEQ ID NO: 39) | RLRKQMAVKKYL (SEQ ID NO: 46) |
| LRKQMAVKKYLNS (SEQ ID NO: 33) | LRKQMAVKKYLN (SEQ ID NO: 40) | LRKQMIAVKKYL (SEQ ID NO: 47) |
| RKQMAVKKYLNS (SEQ ID NO: 34) | RKQMAVKKYLN (SEQ ID NO: 41) | RKQMAVKKYL (SEQ ID NO: 48) |
| KQMAVKKYLNS (SEQ ID NO: 35) | KQMAVKKYLN (SEQ ID NO: 42) | KQMAVKKYL (SEQ ID NO: 49) |
| QMAVKKYLNS (SEQ ID NO: 36) | QMAVKKYLN (SEQ ID NO: 43) | QMAVKKYL (SEQ ID NO: 50) |
| MAVKKYLNS (SEQ ID NO: 37) | MAVKKYLN (SEQ ID NO: 44) | MAVKKYL (SEQ ID NO: 51) |
| AVKKYLNS (SEQ ID NO: 38) | AVKKYLN (SEQ ID NO: 45) | AVKKYL (SEQ ID NO: 52) | as analogs of the sequence that follows the VIP, the following are selected:

| | |
|---|---|
| FSDAVFTDNYTRLRKQMAVKKYLNSILN | (SEQ ID NO: 53) |
| ISDAVFTDNYTRLRKQMAVKKYLNSILN | (SEQ ID NO: 54) |
| LSDAVFTDNYTRLRKQMAVKKYLNSILN | (SEQ ID NO: 55) |
| HFDAVFTDNYTRLRKQMAVKKYLNSILN | (SEQ ID NO: 56) |
| HHDAVFTDNYTRLRKQMAVKKYLNSILN | (SEQ ID NO: 57) |
| HIDAVFTDNYTRLRKQMAVKKYLNSILN | (SEQ ID NO: 58) |
| HLDAVFTDNYTRLRKQMAVKKYLNSILN | (SEQ ID NO: 59) |
| HMDAVFTDNYTRLRKQMAVKKYLNSILN | (SEQ ID NO: 60) |
| HQDAVFTDNYTRLRKQMAVKKYLNSILN | (SEQ ID NO: 61) |
| HTDAVFTDNYTRLRKQMAVKKYLNSILN | (SEQ ID NO: 62) |
| HVDAVFTDNYTRLRKQMAVKKYLNSILN | (SEQ ID NO: 63) |
| HWDAVFTDNYTRLRKQMAVKKYLNSILN | (SEQ ID NO: 64) |
| HYDAVFTDNYTRLRKQMAVKKYLNSILN | (SEQ ID NO: 65) |
| HSAAVFTDNYTRLRKQMAVKKYLNSILN | (SEQ ID NO: 66) |
| HSEAVFTDNYTRLRKQMAVKKYLNSILN | (SEQ ID NO: 67) |
| HSFAVFTDNYTRLRKQMAVKKYLNSILN | (SEQ ID NO: 68) |
| HSHAVFTDNYTRLRKQMAVKKYLNSILN | (SEQ ID NO: 69) |
| HSIAVFTDNYTRLRKQMAVKKYLNSILN | (SEQ ID NO: 70) |
| HSLAVFTDNYTRLRKQMAVKKYLNSILN | (SEQ ID NO: 71) |
| HSMAVFTDNYTRLRKQMAVKKYLNSILN | (SEQ ID NO: 72) |
| HSWAVFTDNYTRLRKQMAVKKYLNSILN | (SEQ ID NO: 73) |
| HSDFVFTDNYTRLRKQMAVKKYLNSILN | (SEQ ID NO: 74) |
| HSDGVFTDNYTRLRKQMAVKKYLNSILN | (SEQ ID NO: 75) |
| HSDMVFTDNYTRLRKQMAVKKYLNSILN | (SEQ ID NO: 76) |
| HSDQVFTDNYTRLRKQMAVKKYLNSILN | (SEQ ID NO: 77) |
| HSDSVFTDNYTRLRKQMAVKKYLNSILN | (SEQ ID NO: 78) |
| HSDWVFTDNYTRLRKQMAVKKYLNSILN | (SEQ ID NO: 79) |
| HSDYVFTDNYTRLRKQMAVKKYLNSILN | (SEQ ID NO: 80) |
| HSDAFFTDNYTRLRKQMAVKKYLNSILN | (SEQ ID NO: 81) |
| HSDAIFTDNYTRLRKQMAVKKYLNSILN | (SEQ ID NO: 82) |
| HSDALFTDNYTRLRKQMAVKKYLNSILN | (SEQ ID NO: 83) |
| HSDAMFTDNYTRLRKQMAVKKYLNSILN | (SEQ ID NO: 84) |
| HSDATFTDNYTRLRKQMAVKKYLNSILN | (SEQ ID NO: 85) |
| HSDAWFTDNYTRLRKQMAVKKYLNSILN | (SEQ ID NO: 86) |

-continued

```
HSDAYFTDNYTRLRKQMAVKKYLNSILN   (SEQ ID NO: 87)
HSDAVKTDNYTRLRKQMAVKKYLNSILN   (SEQ ID NO: 88)
HSDAVFVDNYTRLRKQMAVKKYLNSILN   (SEQ ID NO: 89)
HSDAVFWDNYTRLRKQMAVKKYLNSILN   (SEQ ID NO: 90)
HSDAVFTDNWTRLRKQMAVKKYLNSILN   (SEQ ID NO: 91)
HSDAVFTDNYTRRRKQMAVKKYLNSILN   (SEQ ID NO: 92)
HSDAVFTDNYTRWRKQMAVKKYLNSILN   (SEQ ID NO: 93)
HSDAVFTDNYTRLRFQMAVKKYLNSILN   (SEQ ID NO: 94)
HSDAVFTDNYTRLRLQMAVKKYLNSILN   (SEQ ID NO: 95)
HSDAVFTDNYTRLRMQMAVKKYLNSILN   (SEQ ID NO: 96)
HSDAVFTDNYTRLRRQMAVKKYLNSILN   (SEQ ID NO: 97)
HSDAVFTDNYTRLRKAMAVKKYLNSILN   (SEQ ID NO: 98)
HSDAVFTDNYTRLRKFMAVKKYLNSILN   (SEQ ID NO: 99)
HSDAVFTDNYTRLRKIMAVKKYLNSILN   (SEQ ID NO: 100)
HSDAVFTDNYTRLRKKMAVKKYLNSILN   (SEQ ID NO: 101)
HSDAVFTDNYTRLRKLMAVKKYLNSJLN   (SEQ ID NO: 102)
HSDAVFTDNYTRLRKMMAVKKYLNSJLN   (SEQ ID NO: 103)
HSDAVFTDNYTRLRKRMAVKKYLNSILN   (SEQ ID NO: 104)
HSDAVFTDNYTRLRKVMAVKKYLNSILN   (SEQ ID NO: 105)
HSDAVFTDNYTRLRKWMAVKKYLNSILN   (SEQ ID NO: 106)
HSDAVFTDNYTRLRKYMAVKKYLNSILN   (SEQ ID NO: 107)
HSDAVFTDNYTRLRKQFAVKKYLNSILN   (SEQ ID NO: 108)
HSDAVFTDNYTRLRKQIAVKKYLNSILN   (SEQ ID NO: 109)
HSDAVFTDNYTRLRKQKAVKKYLNSJLN   (SEQ ID NO: 110)
HSDAVFTDNYTRLRKQLAVKKYLNSILN   (SEQ ID NO: 111)
HSDAVFTDNYTRLRKQQAVKKYLNSILN   (SEQ ID NO: 112)
HSDAVFTDNYTRLRKQRAVKKYLNSILN   (SEQ ID NO: 113)
HSDAVFTDNYTRLRKQWAVKKYLNSILN   (SEQ ID NO: 114)
HSDAVFTDNYTRLRKQMFVKKYLNSILN   (SEQ ID NO: 115)
HSDAVFTDNYTRLRKQMIVKKYLNSILN   (SEQ ID NO: 116)
HSDAVFTDNYTRLRKQMKVKKYLNSILN   (SEQ ID NO: 117)
HSDAVFTDNYTRLRKQMLVKKYLNSILN   (SEQ ID NO: 118)
HSDAVFTDNYTRLRKQMMVKKYLNSILN   (SEQ ID NO: 119)
HSDAVFTDNYTRLRKQMQVKKYLNSILN   (SEQ ID NO: 120)
HSDAVFTDNYTRLRKQMRVKKYLNSILN   (SEQ ID NO: 121)
HSDAVFTDNYTRLRKQMVVKKYLNSILN   (SEQ ID NO: 122)
HSDAVFTDNYTRLRKQMWVKKYLNSILN   (SEQ ID NO: 123)
HSDAVFTDNYTRLRKQMYVKKYLNSILN   (SEQ ID NO: 124)
HSDAVFTDNYTRLRKQMAAKKYLNSILN   (SEQ ID NO: 125)
HSDAVFTDNYTRLRKQMAJKKYLNSILN   (SEQ ID NO: 126)
```

-continued

```
HSDAVFTDNYTRLRKQMALKKYLNSILN   (SEQ ID NO: 127)
HSDAVFTDNYTRLRKQMAVRKYLNSILN   (SEQ ID NO: 128)
HSDAVFTDNYTRLRKQMAVKRYLNSILN   (SEQ ID NO: 129)
HSDAVFTDNYTRLRKQMAVKWYLNSILN   (SEQ ID NO: 130)
HSDAVFTDNYTRLRKQMAVKKFLNSILN   (SEQ ID NO: 131)
HSDAVFTDNYTRLRKQMAVKKWLNSILN   (SEQ ID NO: 132)
HSDAVFTDNYTRLRKQMAVKKYLASILN   (SEQ ID NO: 133)
HSDAVFTDNYTRLRKQMAVKKYLFSILN   (SEQ ID NO: 134)
HSDAVFTDNYTRLRKQMAVKKYLJSILN   (SEQ ID NO: 135)
HSDAVFTDNYTRLRKQMAVKKYLMSILN   (SEQ ID NO: 136)
HSDAVFTDNYTRLRKQMAVKKYLSSILN   (SEQ ID NO: 137)
HSDAVFTDNYTRLRKQMAVKKYLVSILN   (SEQ ID NO: 138)
HSDAVFTDNYTRLRKQMAVKKYLWSILN   (SEQ ID NO: 139)
HSDAVFTDNYTRLRKQMAVKKYLNNILN   (SEQ ID NO: 140)
HSDAVFTDNYTRLRKQMAVKKYLNRILN   (SEQ ID NO: 141)
HSDAVFTDNYTRLRKQMAVKKYLNWILN   (SEQ ID NO: 142)
HSDAVFTDNYTRLRKQMAVKKYLNYILN   (SEQ ID NO: 143)
HSDAVFTDNYTRLRKQMAVKKYLNSLLN   (SEQ ID NO: 144)
HSDAVFTDNYTRLRKQMAVKKYLNSSLN   (SEQ ID NO: 145)
HSDAVFTDNYTRLRKQMAVKKYLNSWLN   (SEQ ID NO: 146)
HSDAVFTDNYTRLRKQMAVKKYLNSYLN   (SEQ ID NO: 147)
HSDAVFTDNYTRLRKQMAVKKYLNSIFN   (SEQ ID NO: 148)
HSDAVFTDNYTRLRKQMAVKKYLNSIIN   (SEQ ID NO: 149)
HSDAVFTDNYTRLRKQMAVKKYLNSIWN   (SEQ ID NO: 150)
HSDAVFTDNYTRLRKQMAVKKYLNSILW   (SEQ ID NO: 151)
``` as an analog of the VIP, a compound is selected according to the following formula:

HSDAVFTX$^1$X$^2$Y X$^3$RLRKQMAVK KYLNS ILN (SEQ ID NO: 152), in which X$^1$, X$^2$ and X$^3$ can represent any amino acid, 2 to m amino acids, independently of one another, can be exchanged for their respective D-amino acid or for other L- or D-amino acids, whereby m has the above indicated meaning, at least one of amino acids $(X)_m$, independently of one another, can be exchanged for other amino acids or amino acid derivatives that are not natural, at least one of amino acids $(X)_m$, independently of one another, can be exchanged for other amino acids or amino acid derivatives that are not natural, such as, e.g., naphthalanine, cyclohexylalanine, norleucine, norvaline, α-aminoadipic acid, α-aminobutyric acid, β-alanine, β-cyclohexylalanine, ornithine, sarcosine or δ-hydroxylysine, as an analog of the VIP, a compound is selected according to the following formula:

X¹SDAVX²TDNX³ TRLRKQMAVK KX⁴LNSI
LN (SEQ ID NO: 153), in which X¹, X², X³ and X⁴ can represent amino acids or amino acid derivatives that are not natural, such as, e.g., naphthalanine, cyclohexylalanine, norleucine, norvaline, α-aminoadipic acid, α-aminobutyric acid, β-alanine, β-cyclohexylalanine, ornithine, sarcosine or δ-hydroxylysine, all amino acids (X)$_m$ are exchanged for their respective D-amino acid, retrosynthetic amino acid sequences are selected as fragments, partial sequences, derivatives or analogs of the vaso-active intestinal peptide, retrosynthetic amino acid sequences, in which 2 to m amino acids are exchanged for the respective D-amino acid, are selected as fragments, partial sequences, derivatives or analogs of the vaso-active, intestinal peptide, whereby m has the above-indicated meaning, the following amino acid sequences are selected as fragments, partial sequences, derivatives or analogs of the vaso-active, intestinal peptide:

| | | |
|---|---|---|
| rlrkqmavkkylnsiln (SEQ ID NO: 11) | rlrkqmavkkylnsil (SEQ ID NO: 18) | rlrkqmavkkylnsi (SEQ ID NO: 25) |
| lrkqmavkkylnsiln (SEQ ID NO: 12) | lrkqmavkkylnsil (SEQ ID NO: 19) | lrkqmavkkylnsi (SEQ ID NO: 26) |
| rkqmavkkylnsiln (SEQ ID NO: 13) | rkqmavkkylnsil (SEQ ID NO: 20) | rkqmavkkylnsi (SEQ ID NO: 27) |
| kqmavkkylnsiln (SEQ ID NO: 14) | kqmavkkylnsil (SEQ ID NO: 21) | kqmavkkyinsi (SEQ ID NO: 28) |
| qmavkkylnsiln (SEQ ID NO: 15) | qmavkkylnsil (SEQ ID NO: 22) | qmavkkylnsi (SEQ ID NO: 29) |
| mavkkyinsiln (SEQ ID NO: 16) | mavkkylnsil (SEQ ID NO: 23) | mavkkylnsi (SEQ ID NO: 30) |
| avkkvlnsiln (SEQ ID NO: 17) | avkkyinsil (SEQ ID NO: 24) | avkkylnsi (SEQ ID NO: 31) |
| RLRKQMAvKKyLNSILN (SEQ ID NO: 11) | RLRKQMAvKKyLNSIL (SEQ ID NO: 18) | RLRKQMAvKKyLNSI (SEQ ID NO: 25) |
| LRKQMAvKKyLNSILN (SEQ ID NO: 12) | LRKQMAvKKyLNSIL (SEQ ID NO: 19) | LRKQMAvKKyLNSI (SEQ ID NO: 26) |
| RKQMAvKKyLNSILN (SEQ ID NO: 13) | RKQMAvKKyLNSIL (SEQ ID NO: 20) | RKQMAvKKyLNSI (SEQ ID NO: 27) |
| KQMAvKKyLNSILN (SEQ ID NO: 14) | KQMAvKKyLNSIL (SEQ ID NO: 21) | KQMAvKKyLNSI (SEQ ID NO: 28) |
| QMAvKKyLNSILN (SEQ ID NO: 15) | QMAvKKyLNSIL (SEQ ID NO: 22) | QMAvKKyLNSI (SEQ ID NO: 29) |
| MAvKKyLNSILN (SEQ ID NO: 16) | MAvKKyLNSIL (SEQ ID NO: 23) | MAvKKyLNSI (SEQ ID NO: 30) |
| AvKKyLNSILN (SEQ ID NO: 17) | AvKKyLNSIL (SEQ ID NO: 24) | AvKKyLNSI (SEQ ID NO: 31) | the following amino acid sequences are selected as fragments, partial sequences, derivatives or analogs of the somatostatin:

| | |
|---|---|
| AGCKNFFwKTFTSC (SEQ ID NO: 9) | AGcKNFFwKTFTSC (SEQ ID NO: 9) |
| AGCKNFFwKTFTSC (SEQ ID NO: 9) | AGCKNFFwKTFTSC (SEQ ID NO: 9) |
| CKNFFwKTFTSC (SEQ ID NO: 154) | cKNFFwKTFTSC (SEQ ID NO: 154) |
| FFYwKVFT (SEQ ID NO: 155) | |
| fCFwKVCT (SEQ ID NO:156) | fcFwKVCT (SEQ ID NO: 156) |
| fCYwKVCT (SEQ ID NO: 157) | fcYwKVCT (SEQ ID NO: 157) |
| fCFwKTCT (SEQ ID NO: 158) | fcFwKTCT (SEQ ID NO: 158) |
| fCYwKTCT (SEQ ID NO: 159) | fcYwKTCT (SEQ ID NO: 159) |
| D-NaI-CYwKVC (SEQ ID NO: 195) | D-NaI-cYwKVC (SEQ ID NO: 195) |
| fCywK-Abu-C-NaI (SEQ ID NO: 160) | fcywK-Abu-C-NaI (SEQ ID NO: 160) | the following amino acid sequences are selected as fragments, partial sequences, derivatives or analogs of the neurotensin:

| | | |
|---|---|---|
| | pGlu-LYQNKPRRPFIL (SEQ ID NO: 165) | pGlu-LYENKPRRPYI (SEQ ID NO: 171) |
| pGlu-LYENKPRRPyIL (SEQ ID NO: 10) | pGlu-LYQNKPRRPfIL (SEQ ID NO: 166) | pGlu-LYENKPRRPY (SEQ ID NO: 172) |
| pGlu-LYQNKPRRPYIL (SEQ ID NO: 161) | pGlu-LYENKPRRPWIL (SEQ ID NO: 167) | pGlu-LYENKPRRP (SEQ ID NO: 173) |
| pGlu-LYQNKPRRPyIL (SEQ ID NO: 162) | pGlu-LYENKPRRPWIL (SEQ ID NO: 168) | pGlu-LYENKPRR (SEQ ID NO: 174) |
| pGlu-LYENKPRRPFIL (SEQ ID NO: 163) | pGlu-LYQNKPRRPWIL (SEQ ID NO: 169) | pGlu-LYENKPR (SEQ ID NO: 175) |
| pGlu-LYENKPRRPfIL (SEQ ID NO: 164) | pGlu-LYQNKPRRPWIL (SEQ ID NO: 170) | pGlu-LYENKP (SEQ ID NO: 176) |
| NKPRRPYIL (SEQ ID NO: 177) | NKPRRPyIL (SEQ ID NO: 177) | NKPRRPfIL (SEQ ID NO: 181) NKPRRPwIL (SEQ ID NO: 185) |

```
KPRRPYIL        KPRRPyIL        KPRRPfIL        KPRRPwIL
(SEQ ID NO: 178) (SEQ ID NO: 178) (SEQ ID NO: 182) (SEQ ID NO: 188)

PRRPYIL         PRRPYIL         PRRPfIL         PRRPwIL
(SEQ ID NO: 179) (SEQ ID NO: 179) (SEQ ID NO: 183) (SEQ ID NO: 187)

RRPYIL          RRPyIL          RRPfIL          RRPwIL
(SEQ ID NO: 180) (SEQ ID NO: 180) (SEQ ID NO: 184) (SEQ ID NO: 188)
```

The terminology of general formula I contains the usual language of amino acid sequences. The N-terminus is always on the left and the C-terminus on the right (unsubstituted according to H—(X)$_m$—OH or, in the case of an amide, H—(X)$_m$—NH$_2$). The one-character abbreviations of the amino acids that are used can be looked up in M. Bodanszky, Peptide Chemistry—A Practical Textbook, 2nd Edition, Springer-Verlag Heidelberg 1993, p. 3. Capital letters mean amino acids with L-configuration (natural amino acids), small letters mean D-amino acids, disulfide bridges (cyclic peptides) are identified by connecting lines between the corresponding letters (C=cysteine or homocysteine). Retrosynthetically, sequences are designated in which in the synthesis, the sequence of the amino acids is inverted in comparison to a given native sequence, i.e., the synthesis begins with the original N-terminal amino acid and produces the sequence up to the original C-terminal amino acid.

The analogs of the VIP were determined using substitution analysis (see Example 43). Especially preferred analogs of the VIP are the following compounds:

His-Trp-Asp-Ala-Val-Phe-Thr-Asp-Asn-Tyr-
Thr-Arg-Leu-Arg-Lys-Gln-Met-Ala-Val-Lys-Lys-Tyr-Leu-Asn-
Ser-Ile-Leu-Asn (SEQ ID NO: 1)

His-Ser-Asp-Ala-Val-Phe-Thr-Phe-Asn-Tyr-
Thr-Arg-Leu-Arg-Lys-Gln-Met-Ala-Val-Lys-Lys-Tyr-Leu-Asn-
Ser-Ile-Leu-Asn (SEQ ID NO: 2)

His-Ser-Asp-Ala-Val-Phe-Thr-Lys-Asn-Tyr-
Thr-Arg-Leu-Arg-Lys-Gln-Met-Ala-Val-Lys-Lys-Tyr-Leu-Asn-
Ser-Ile-Leu-Asn (SEQ ID NO: 3)

His-Ser-Asp-Ala-Val-Phe-Thr-Gln-Asn-Tyr-
Thr-Arg-Leu-Arg-Lys-Gln-Met-Ala-Val-Lys-Lys-Tyr-Leu-Asn-
Ser-Ile-Leu-Asn (SEQ ID NO: 4)

His-Ser-Asp-Ala-Val-Phe-Thr-Arg-Asn-Tyr-
Thr-Arg-Leu-Arg-Lys-Gln-Met-Ala-Val-Lys-Lys-Tyr-Leu-Asn-
Ser-Ile-Leu-Asn (SEQ ID NO: 5)

His-Ser-Asp-Ala-Val-Phe-Thr-Trp-Asn-Tyr-
Thr-Arg-Leu-Arg-Lys-Gln-Met-Ala-Val-Lys-Lys-Tyr-Leu-Asn-
Ser-Ile-Leu-Asn (SEQ ID NO: 6)

His-Ser-Asp-Ala-Val-Phe-Thr-Asp-Asn-Tyr-
Arg-Arg-Leu-Arg-Lys-Gln-Met-Ala-Val-Lys-Lys-Tyr-Leu-Asn-
Ser-Ile-Leu-Asn (SEQ ID NO: 7)

His-Ser-Asp-Ala-Val-Phe-Thr-Asp-Asn-Tyr-
Thr-Arg-Leu-Arg-Lys-Gln-Met-Arg-Val-Lys-Lys-Tyr-Leu-Asn-
Ser-Ile-Leu-Asn (SEQ ID NO: 8).

The substances according to the invention have various advantages compared to radiolabeled substances. Fluorescence dyes can often be excited at will for fluorescence emission. No continuous signal is present, which uses as a basis a decomposition with corresponding half-life. Consequently, the time of diagnosis can be selected at will and can be repeated as often as desired and is not limited by the half-life of an isotope. The patient is not exposed to any ionizing radiation, and the light radiation that is used is harmless in the doses used. The optical detection technique allows the highly sensitive detection of a few photons and is therefore comparable to radiodiagnosis relative to the sensitivity.

A process for diagnosis using near-infrared radiation (NIR radiation) with use of dye biomolecule conjugates was described (WO 96/17628). It has proven especially advantageous in the case of this invention that the peptide conjugates in advantageous yield and high purity can be produced by the process of the automated solid-phase synthesis. It has been found, surprisingly enough, that various carboxyl group-carrying indocyanine compounds can be used as amino acid analogs, and both N-terminal groups and an amino group of the lysine can be coupled to the solid phase (resin). After resin is cleaved off and after chromatographic purification, the dye-peptide conjugates were obtained in purities>95%. A new coupling process allows the coupling of haloacetyl dyes to the amino acid cysteine or homocysteine, which can replace any amino acid of the native VIP sequence.

The basic problem when using light for fluorescence excitation is the limited penetration depth of the light, which is in the submillimeter range in the VIS, but can be in centimeters in the NIR. With respect to-the penetration depth, detection processes are without problems in surface tissue diseases, as well as soft tissues. Subjects of the invention are therefore mammographic processes, endoscopic processes and intraoperative processes, in which diseased tissue areas are diagnosed with use of the compounds according to the invention by detection of fluorescence or the non-absorbed radiation. A more special subject of the invention is the use of the compounds according to the invention in endoscopic processes, e.g., coloscopy, bronchoscopy, esophageal endoscopy, in which changes in tissue that are near the surface are diagnosed. The use of white light with direct visual evaluation is common in endoscopic diagnosis. The compounds according to the invention contribute to a decisive improvement of the process by the production of a tissue-specific signal, especially in the case of the diagnosis of premature, visually undetectable tissue changes (e.g., dysplasias of the colon).

It has been found that after the dye-coupled compounds according to the invention are atomized in the intestines of rats with chemically induced dysplasias and colon carcinomas, subsequent flushing and the implementation of an endoscopic fluorescence diagnosis (excitation 740 nm, detection above 760 nm) make it possible to detect tissue areas of increased fluorescence in the colon.

The subject of the invention is therefore also a process for endoscopic fluorescence diagnosis, especially of the gastrointestinal tract, with use of the compounds according to the invention. In this case, one or more of the substances are fed to the tissue preferably intravenously, or topically by atomization, and the light from the corresponding spectral range is irradiated for electronic excitation of the dye that is used. The reflected fluorescence radiation or the fluorescence radiation that is emitted by the dye is recorded. Preferred are the methods in which the tissue is irradiated over a large surface, and the fluorescence radiation is indicated with local resolution by imaging with a CCD camera, or the tissue areas that are to be imaged are rastered with a fiber optic light guide, and the signals that are obtained are reacted by computer into a synthetic image. In this case, the fluorescence can be detected and evaluated spectrally and/or phase-selectively as well as in a stationary and/or time-resolved manner. The fluorescence images that are obtained can be produced at the same time as the white light images and are produced over one another in a figure for data evaluation.

The synthesis of the compounds according to the invention is carried out in a way that is similar to the methods that are known in the literature. The peptides are produced in a solid-phase-synthetic manner in polymer resins. Details are known to one skilled in the art. Literature: Peptide Chemistry—A Practical Textbook (M. Bodanszky), 2nd Edition, Springer-Verlag Heidelberg 1993; Anti-Cancer Drug Design 12, 145–167, 1997; J. Am. Chem. Soc. 117, 11821–2, 1995.

The dyes are produced separately and then, as part of the solid-phase-synthetic production of the peptides, the dyes are coupled to the peptides, and the compounds according to the invention are obtained as highly pure compounds after cleavage from resin and purification. Preferred are those dyes that contain carboxyl groups, which after activation with common reagents are coupled to amino groups of the peptide, especially the ξ-amino group of the lysine or the N-terminal peptide-amino group. In addition, dyes with haloalkyl or haloacetyl radicals are preferred that are coupled to thiol groups of the peptide, especially the amino acid cysteine or homocysteine.

Literature on the synthesis of polymethine dyes: Bioconjugate Chem. 4, 105–111, 1993: Bioconjugate Chem. 7, 356–62, 1996; Bioconjugate Chem. 8, 751–56, 1997; Cytometry 10, 11–19, 1989 and 11, 418–30, 1990; J. Heterocycl. Chem. 33, 1871–6, 1996; J. Org. Chem. 60, 2391–5, 1995; Dyes and Pigments 17, 19–27, 1991, Dyes and Pigments 21, 227–34, 1993; J. Fluoresc. 3, 153–155, 1993; Anal. Biochem. 217, 197–204, 1994; U.S. Pat. Nos. 4,981, 977; 5,688,966; 5,808,044; WO 97/42976; WO 97/42978; WO 98/22146; WO 98/26077; EP 0800831.

Especially suitable for a coupling to peptides in the solid phase are dyes that contain precisely one carboxyl group, especially advantageously cyanine dyes of general formula XVIII

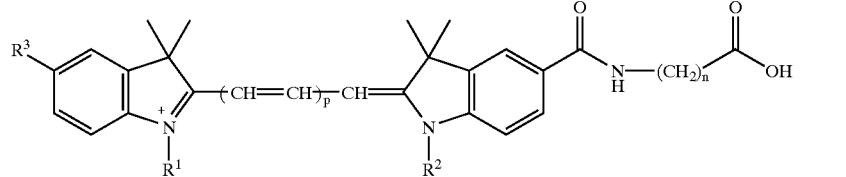

XVIII in which p stands for 1, 2 or 3, n stands for 1, 2, 3, 4 or 10, $R^1$ and $R^2$, independently of one another, stand for a 4-sulfobutyl, 3-sulfopropyl, 2-sulfoethyl, 3-methyl-3-sulfopropyl, methyl, ethyl or propyl radical, and $R^3$ stands for hydrogen or for a radical —COOE$^1$, —CONE$^1$E$^2$, —NHCOE$^1$, —NHCONHE$^1$, —NE$^1$E$^2$, —OE$^1$, —OSO$_3$E$^1$, —SO$_3$E$^1$, —SO$_2$NHE$^1$, whereby E$^1$ and E$^2$, independently of one another, stand for a hydrogen atom or for a methyl, ethyl or a C$_3$–C$_6$ alkyl radical, which is interrupted by 0 to 2 oxygen atoms and/or by 0 to 1 carbonyl groups and/or is substituted by 0 to 5 hydroxy groups, or cyanine dyes of general formula XIX or XX

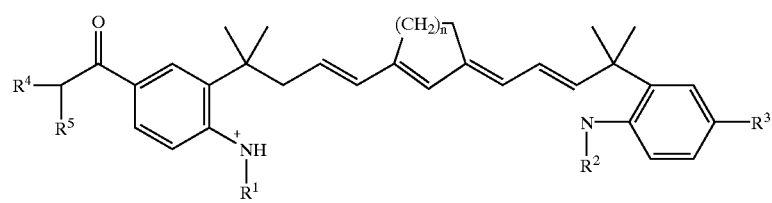

XIX

-continued

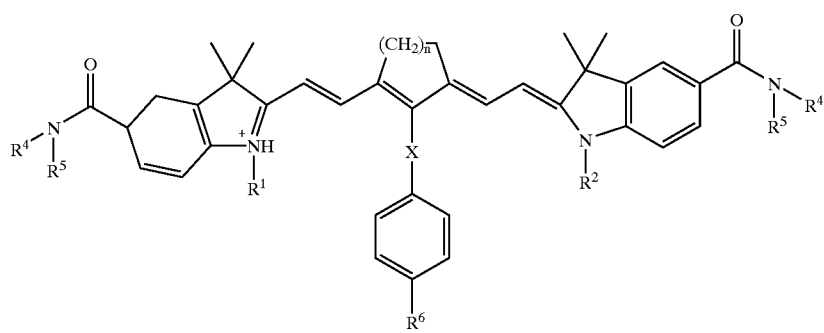

XX in which n stands for 2 or 3,

R¹ and R², independently of one another, represent a 4-sulfobutyl, 3-sulfopropyl or 2-sulfoethyl radical, R³ stands for a —COOH group or one of the following radicals:
—CONH—$(CH_2)_n$—COOH with n=2 or 3,
—CONH—$(CH_2)_n$—NCS with n=2 or 3,
—CONH—$(CH_2)_n$—NHCO—$C_2$—$X^1$ with n=2 or 3 and $X^1$=Cl, Br, I

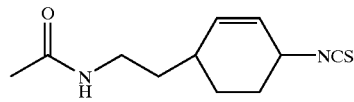

R⁴ and R⁵, independently of one another, stand for a hydrogen atom, a methyl radical or a hydroxylated alkyl radical, such as, e.g., 2-hydroxyethyl, 3-hydroxypropyl, 2,3-dihydroxypropyl, 1,3-dihydroxy-2-propyl, 2,3,4-trihydroxybutyl, 1,3,4-trihydroxy-2-butyl, 2,3,4,5,6-pentahydroxyhexyl, R⁶ stands for one of the following groups:
—$(CH_2)_m$—COOH with m=0 to 2,
—$(CH_2)_m$—NCS with m=0 to 2, and X stands for an oxygen atom or a sulfur atom; or cyanine dyes of general formula XXI —CONH—$(CH_2)_n$—NHCO—$C_2$—$X^1$ with n=2 or 3 and $X^1$=Cl, Br, I

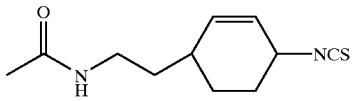

and R⁴ and R⁵, independently of one another, stand for a hydrogen atom, a methyl radical or a hydroxylated alkyl radical, such as, e.g., 2-hydroxyethyl, 3-hydroxypropyl, 2,3-dihydroxypropyl, 1,3-dihydroxy-2-propyl, 2,3,4-trihydroxybutyl, 1,3,4-trihydroxy-2-butyl, 2,3,4,5,6-pentahydroxyhexyl.

The advantage of only one activatable group, such as, e.g., a carboxyl group, or an already activated group, such as, e.g., an isothiocyanate, a haloalkyl group or a haloacetyl group, consists in the fact that a chemically uniform coupling can be carried out. The haloacetyl group has the special advantage that a chemically uniform coupling to the mercapto group of the cysteine or homocysteine is carried out. This coupling can be carried out in solution to the unbonded peptide from which protective groups are removed. By the activated groups, a coupling to peptides is possible without secondary reactions occurring. To increase the water solubility, the peptide-dye conjugates in the dye exhibit an increased number of hydroxy groups. By the position of the linker in the indole system of the dye, in addition an adequate hydrophilia by radicals that contain sulfonate

XXI

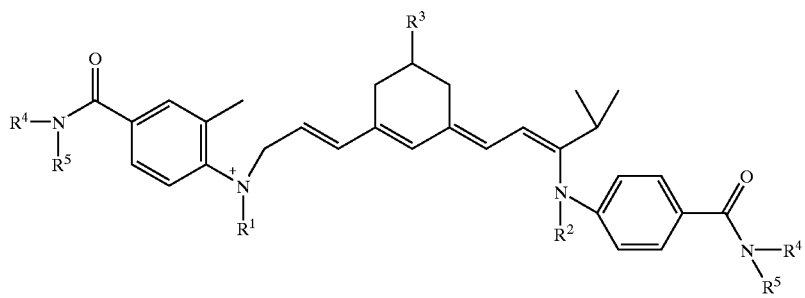

in which

R¹ and R², independently of one another, stand for a 4-sulfobutyl-, 3-sulfopropyl or 2-sulfoethyl radical, R³ stands for a —COOH group or one of the following radicals:
—CONH—$(CH_2)_n$—COOH with n=2 or 3,
—CONH—$(CH_2)_n$—NCS with n=2 or 3, groups can be produced in the nitrogen atoms of the indole system. As a result, a structurally uniform coupling reaction can be performed with the peptides (see Examples 4 to 38 and 44 to 49).

Another subject of the invention is an optical diagnostic agent for in-vivo diagnosis of diseased tissue areas, which is distinguished in that it contains at least one compound of general formula I together with common adjuvants and/or vehicles as well as diluents.

The following examples explain the invention:

EXAMPLES 1 TO 3

Synthesis of Indocyanine Dyes 1–3 for Solid-phase-synthetic Coupling to Amino Groups (N-terminal or ξ-lysine) of the Peptides The synthesis is generally carried out starting from 1-(4-sulfobutyl)-2,3,3-trimethyl-3H-indolenine and 1-(4-sulfobutyl)-2,3,3-trimethyl-5-carboxy-3H-indolenine (Cytometry 10, 11–19, 1989, Talanta 39, 505–510, 1992).

EXAMPLE 1

Synthesis of 1,1'-bis(4-sulfobutyl)indocarbocyanine-5-carboxylic acid, sodium salt (1)

0.8 g (4.0 mmol) of N,N-diphenylformamidine is introduced into 15 ml of acetic acid anhydride and mixed at room temperature in portions with 1.4 g (4.2 mmol) of 1-(4-sulfobutyl)-2,3,3-trimethyl-5-carboxy-3H-indolenine, stirred for 30 minutes at 120° C. and then cooled to room temperature with a water bath. Then, 1.2 g (4.1 mmol) of 1-(4-sulfobutyl)-2,3,3-trimethyl-3H-indolenine, 1.2 g (14.6 mmol) of anhydrous sodium acetate, 15 ml of acetic acid anhydride and 6 ml of acetic acid are added. The reaction mixture is heated for 1 hour to 120° C., and the dark red solution is cooled and mixed with 100 ml of ether. The precipitated solid is filtered off. A chromatographic purification on RP-silica gel EUROPREP 60–30 C18, 60A, 20–45 m is carried out (eluant: water/MeOH, step gradient of 0% to 70% MeOH). Methanol is removed from the product-containing fractions in a rotary evaporator, and the fractions are then freeze-dried, yield: 1.5 g (58%), red lyophilizate.

EXAMPLE 2

Synthesis of 1,1'-bis(4-sulfobutyl) indodicarbocyanine-5-carboxylic acid, sodium salt (2)

1.2 g (4.1 mmol) of 1-(4-sulfobutyl)-2,3,3-trimethyl-3H-indolenine and 1.0 g (3.9 mmol) of malonaldehyde-bis-phenylimine hydrochloride are stirred in 15 ml of acetic acid anhydride for 30 minutes at 120° C. and then cooled to room temperature with a water bath. Then, 1.4 g (4.2 mmol) of 1-(4-sulfobutyl)-2,3,3-trimethyl-5-carboxy-3H-indolenine, 1.2 g (14.6 mmol) of anhydrous sodium acetate, 15 ml of acetic acid anhydride and 6 ml of acetic acid are added in succession. The reaction mixture is heated for 1 hour to 120° C., the solution that is now blue is cooled and mixed with 100 ml of ether. The working-up and purification are carried out as described in Example 1. Yield: 1.8 g (66%), blue lyophilizate.

EXAMPLE 3

Synthesis of 1,1'-bis(4-sulfobutyl) indotricarbocyanine-5-carboxylic acid, sodium salt (3)

1.2 g (4.1 mmol) of 1-(4-sulfobutyl)-2,3,3-trimethyl-3H-indolenine and 1.1 g (3.9 mmol) of glutaconaldehyde-dianil hydrochloride are stirred in 15 ml of acetic acid anhydride for 30 minutes at 120° C. and then cooled to room temperature with a water bath. Then, 1.4 g (4.2 mmol) of 1-(4-sulfobutyl)-2,3,3-trimethyl-5-carboxy-3H-indolenine, 1.2 g (14.6 mmol) of anhydrous sodium acetate, 15 ml of acetic acid anhydride and 6 ml of acetic acid are added. The reaction mixture is heated for 1 hour to 120° C., the now blue solution is cooled and mixed with 100 ml of ether. The working-up and purification are carried out as described in Example 1, yield: 1.8 g (60%), blue lyophilizate.

The structures of the compounds of Examples 1–3 are depicted in FIG. 1.

EXAMPLES 4 TO 6

Synthesis of Indocyanine Dyes 4–6 from 1–3 for Solid-phase-synthetic Coupling to Amino Groups (N-terminal or ξ-lysine) of the Peptides The synthesis is carried out by amidation of dyes 1–3 with β-alanine-t-butylester and acidic cleavage of the t-butylester group.

A solution of 0.5 mmol of dyes 1–3 and 0.1 g (1.0 mmol) of triethylamine in 20 ml of dimethylformamide is mixed at 0° C. with 0.5 mmol of TBTU in 10 ml of dimethylformamide, and it is stirred for 15 minutes at 0° C. Then, a solution of 0.11 g (0.6 mmol) of β-alanine-t-butylester-hydrochloride and 0.6 mmol of triethylamine in 5 ml of dimethylformamide is added in drops, and the reaction mixture is stirred for 2 hours at room temperature. After 100 ml of diethyl ether is added, the precipitated solid is filtered off, dissolved in 20 ml of dichloromethane, mixed with 10 ml of trifluoroacetic acid and stirred for 24 hours at room temperature. The mixture is concentrated by evaporation in a vacuum, and the residue is purified by chromatography and freeze-dried as described in Example 1; yields: 0.21 g (58%) of 4, 0.29 g (76%) of 5, 0.28 g (72%) of 6.

EXAMPLES 7 TO 9

Synthesis of Indocyanine Dyes 7–9 from 1–3 for Solid-phase-synthetic Coupling to Amino Groups (N-terminal or ξ-lysine) of the Peptides The production is carried out analogously to Examples 4–6 with use of 0.1 g (0.6 mmol) of glycine-t-butylester-hydrochloride, yields: 0.25 g (68%) of 4, 0.30 g (80%) of 5, 0.32 g (83%) of 6.

EXAMPLES 10 TO 12

Synthesis of Indocyanine Dyes 10–12 from 1–3 for Solid-phase-synthetic Coupling to Peptides by Coupling to Thiol Groups of Cysteine The synthesis is carried out by amidation of dyes 1–3 with 3-aminopropanol and subsequent conversion of the alcohol group into a bromide.

A solution of 0.5 mmol of dyes 1–3 and 0.1 g (1.0 mmol) of triethylamine in 20 ml of dimethylformamide is mixed at 0° C. with 0.5 mmol of TBTU in 10 ml of dimethylformamide, and it is stirred for 15 minutes at 0° C. Then, a solution of 850 mg (1.2 mmol) of 3-aminopropanol and 1.2 mmol of triethylamine in 5 ml of dimethylformamide is added in drops, and the reaction mixture is stirred for 6 hours at room temperature. After 100 ml of diethyl ether is added, the precipitated solid is filtered off and purified by chromatography and freeze-dried as described in Example 1.

The reaction to bromides 10–12 is carried out by stirring 0.3 mmol of the intermediate products with 55 mg (0.5 mmol) of N-bromosuccinimide and 130 mg (0.5 mmol) of triphenylphosphine in a mixture of 4 ml of dichloromethane and 4 ml of dimethylformamide for 48 hours at 4° C. By adding 3 ml of ether, the products are precipitated, filtered off and used as crude products in the peptide coupling.

EXAMPLES 14–16 AND 18–27

Resin Synthesis of Peptide Conjugates of VIP-receptor-binding Peptides and Dyes 1–9 and 13.

a) Solid-phase Peptide Synthesis

According to the Fmoc strategy and analogously to the standard-Fmoc machine protocol (Pept. Res., 36 (1990) 225), the peptides are synthesized in 50 μmol of TentaGel-Sram resin (Rapp Polymers, Tubingen) with use of coupling reagent PyBOP (benzotriazol-1-yloxy-tris-pyrrolidinophosphonium hexafluorophosphate) and N-methylmorpholine. The following side-protective groups were used: trityl for Cys, His, Asn and Gln; t-butyl for Asp, Glu, Ser and Thr; t-butyloxycarbonyl for Lys and Trp, and pentamethylchromanosulfonyl for Arg.

The coupling to the ξ-amino group of a lysine (Example 24) is achieved by orthogonal protective group technology. As a lysine component, Fmoc-Lys(Dde-OH) is used, and the peptide is synthesized as described above. After acetylation of the N-terminus, the cleavage of the Dde-protective groups is carried out selectively by 3% hydrazine hydrate.

b) Dye Coupling

The dyes are bonded in the N-terminal position or to lysine in the peptides that are still solid-phase-bonded. In this connection, 75 μmol of the respective dyes 1·9 and 13 (1.5 eq) in 600 μl of dimethylformamide is dissolved and mixed with 83 μmol of TBTU (2-(1H-benzotriazol-1-yl)-1,1,3,3-tetramethyluronium-tetrafluoroborate) and 150 μmol of N,N-diisopropylethylamine. After 2 minutes, this reaction mixture is added to the respective peptide-carrying resin and allowed to react overnight. Then, the resin is washed 5 times with dimethylformamide and 3 times with dichloromethane and dried in air.

c) Protective Group Cleavage and Detachment of the Dye-peptide-conjugates 1.5 ml each of a mixture that consists of 750 mg of phenol, 250 μl of ethanedithiol, 500 μl of thioanisole and 500 μl of water in 10 ml of trifluoroacetic acid are added to the peptide-conjugate-carrying resin and allowed to act for four hours. The dye-peptide conjugates are precipitated with cold t-butylmethyl ether, washed six times with cold diethyl ether, dissolved in 5% acetic acid and freeze-dried. Purity analysis and purification of the conjugates are carried out with use of RP-HPLC in a Vydac-C18 column (gradient: water+0, 05% TFA/acetonitrile, 5% to 60% acetonitrile in 20 minutes, detection: 214 and 750 nm).

The structures of the synthesized dye-peptide conjugates are summarized in the following survey:

Dye Conjugates with VIP-Receptor-Binding Peptides I

EXAMPLES 14 TO 16

Conjugates of dyes 1–3 with VIP (1–28) (SEQ ID NO: 196)

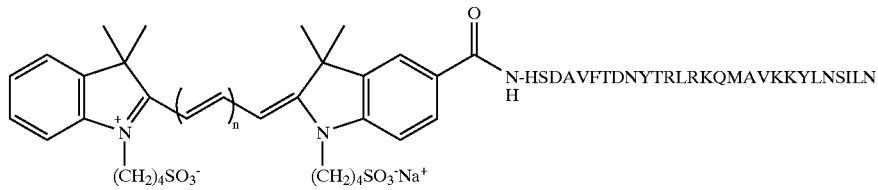

n=1: Indocarbocyanine-VIP (1–28)-conjugate 14
n=2: Indodicarbocyanine-VIP (1–28)-conjugate 15
n=3: Indotricarbocyanine-VIP (1–28)-conjugate 16

EXAMPLE 17

Conjugate of Dye 12 with $Cys^{17}$-VIP (1–28)

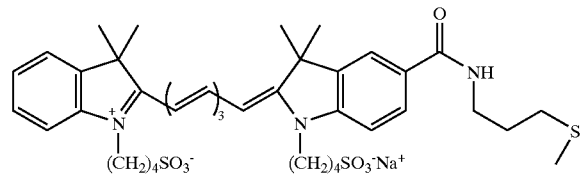

HSDAVFTDNYTRLRKQ-Cys-AVKKYLNSILN (SEQ ID NO: 189)

Indotricarbocyanine-$Cys^{17}$-VIP (1–28)-conjugate 17

EXAMPLES 18 TO 20

Conjugates of dyes 1–3 with VIP (14–28) (SEQ ID NO: 13)

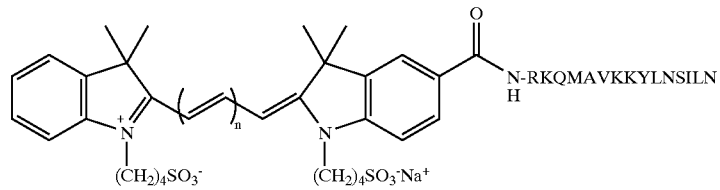

n=1: Indocarbocyanine-VIP (14–28)-conjugate 18
n=2: Indodicarbocyanine-VIP (14–28)-conjugate 19
n=3: Indotricarbocyanine-VIP (14–28)-conjugate 20

EXAMPLES 21 TO 23

Conjugates of dyes 4–6 with VIP (14–24) (SEQ ID NO: 190)

EXAMPLE 24

Conjugate of dye 6 with Lys$^{25}$-VIP (14–25) (SEQ ID NO: 191)

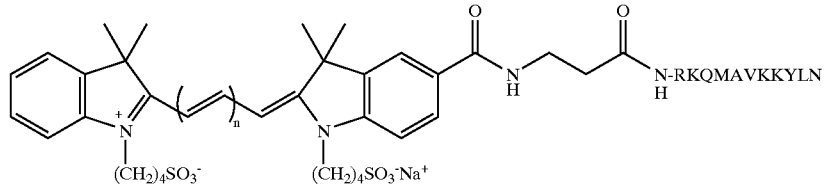

n=1: Indocarbocyanine-β-alanine-VIP (14–24)-conjugate 21 n=2: Indodicarbocyanine-β-alanine-VIP (14–24)-conjugate 22 n=3: Indotricarbocyanine-β-alanine-VIP (14–24)-conjugate 23

EXAMPLE 17

Resin Synthesis of Peptide Conjugates that Consist of VIP-receptor-binding Peptides and Dyes 10–12

To bind bromine-carrying dyes 10–12 chemoselectively via a thioether bond to the peptides, a cysteine or homocysteine with an orthogonal protective group must be incorporated in the peptide. The solid-phase-peptide synthesis is carried out as described for Examples 14–16/18–27, and the component Fmoc-cys (Mmt-OH is used. The monomethoxytrityl group (Mmt) can be cleaved by 1% TFA/5% triisobutylsilane in dichloromethane while obtaining the other side protective groups. In this connection, the resin is incubated three times with 1 ml each of the above solution for 10 minutes. After the resin is washed with dichloromethane (3×), DMF (5×) and ethanol (3×), the resin is incubated for 2 minutes with a 20% cesium carbonate solution (1 ml) and then washed with water (2×), ethanol (2×) and DMF (2×). Then, 75 μmol of respective dye 10–12 (1.5 eq) is dissolved in 600 μl of dimethylformamide and added to the respective resin, and the process is repeated after 30 minutes. Then, the resin is washed five times with dimethylformamide (5×) and with dichloromethane (2×). After the resin is dried in air, the protective group cleavage and detachment of the vehicle are carried out as described above.

The structures of other synthesized dye-peptide conjugates are summarized in the following survey:

Dye Conjugates with VIP-Receptor-Binding Peptides II

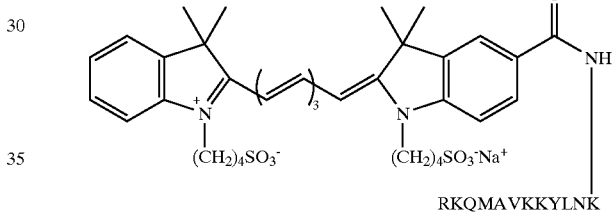

(ξ-Amino-indotricarbocyanine)-Lys$^{25}$-VIP (14–25)-conjugate 24

EXAMPLE 25

Conjugate of dye 3 with D-VIP (14–24) (SEQ ID NO: 192)

Indotricarbocyanine-D-VIP (14–24)-conjugate 25

EXAMPLE 26

Conjugate of dye 13 with D-VIP (14–24) (SEQ ID NO: 192)

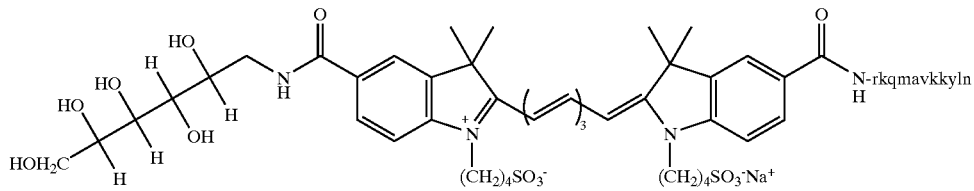

Indotricarbocyanine-5-carboxylic acid glucamide-D-VIP (14–24)-conjugate 26

EXAMPLE 27

Conjugate of dye 13 with retro-D-VIP (14–24) (SEQ ID NO: 193)

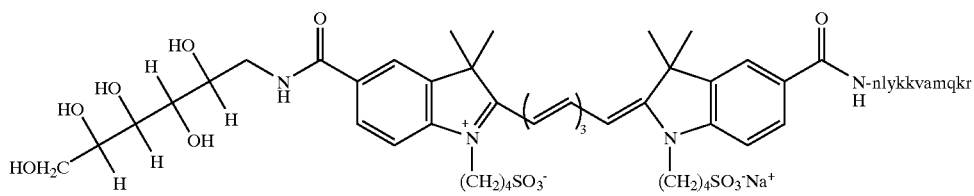

Indotricarbocyanine-5-carboxylic acid glucamide-retro-D-VIP (14–24)-conjugate 27

EXAMPLES 28 TO 32

Resin Synthesis of Peptide Conjugates that Consist of Somatostatin-receptor-binding Peptides and Dyes 1–9 and 13

General Instructions

The syntheses were performed on 500 mg of TCP-Thr (But)-fmoc-resin (Pepchem Tübingen Company) with a concentration or 0.49 mmol/g. The peptide is synthesized "step by step" with use of the following temporary protective groups: tert-butyl for Thr and Ser, trityl for Cys and Asp, Boc for Trp and Lys. As a condensation reagent, HBTU is used.

After cleavage of the N-terminal Fmoc-protective group, dyes 1–9, 13 are condensed in a special synthesis step. To this end, 255 mg of resin is suspended in about 2 ml of DMF and mixed with 0.5 mmol of dye, 0.5 mmol of HBTU and 0.17 ml of DIEA. It is stirred for 18 hours at room temperature, the resin is suctioned off, washed with dichloromethane and dried. The cleavage of the dye-peptide conjugate from resin was carried out with 95% trifluoroacetic acid with the addition of triisopropylsilane with subsequent freeze-drying from 10% acetic acid. The crude product is cyclized with use of activated carbon and purified by chromatography (50×300 mm VYDAC RP-18, gradient: water/acetonitrile).

The structures of the synthesized dye-peptide conjugates are summarized in the following survey:

Dye Conjugates with Somatostatin-Receptor-Binding Peptides

EXAMPLES 28 TO 30

Conjugate of dyes 1–3 with pentetreotide (SEQ ID NO: 158)

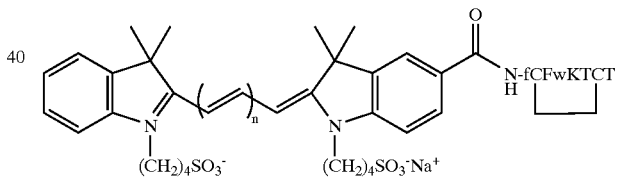

n=1: Indocarbocyanine-pentetreotide 28
n=2: Indodicarbocyanine-pentetreotide 29
n=3: Indotricarbocyanine-pentetreotide 30

EXAMPLE 31

Conjugate of dye 3 with somatostatin-14 (SEQ ID NO: 9)

Indotricarbocyanine-somatostatin-14-conjugate 31

EXAMPLE 32

Conjugate of dye 13 with somatostatin-14 (SEQ ID NO: 9)

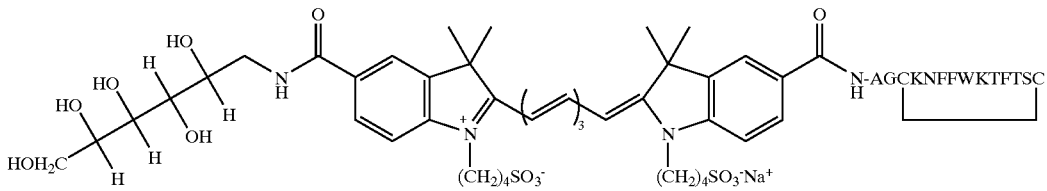

Indotricarbocyanine-5-carboxylic acid-glucamide-somatostatin-14-conjugate 32

EXAMPLES 33 TO 38

Synthesis of Peptide Conjugates from Neurotensin Peptides and Dye 3

The synthesis of substances is carried out analogously to the general protocols that are described for Examples 14–27.

The structures of the synthesized dye-peptide conjugates are summarized in the following survey:
Dye Conjugates with Neurotensin-Receptor-Binding Peptides

EXAMPLES 33 TO 35

Conjugate of dyes 7–9 with D-Tyr[11]-neurotensin (7–13) (SEQ ID NO: 179)

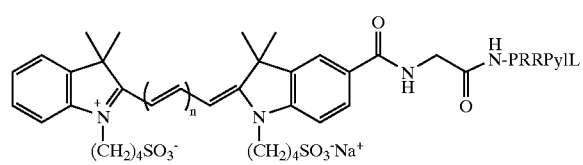

n=1: Indocarbocyanine-D-Tyr[11]-neurotensin (7–13)-conjugate 33
n=2: Indodicarbocyanine-D-Tyr[11]-neurotensin (7–13)-conjugate 34
n=3: Indotricarbocyanine-D-Tyr[11]-neurotensin (7–13)-conjugate 35

EXAMPLE 36

Conjugate of dye 2 with D-Tyr[11]-neurotensin (SEQ ID NO: 10)

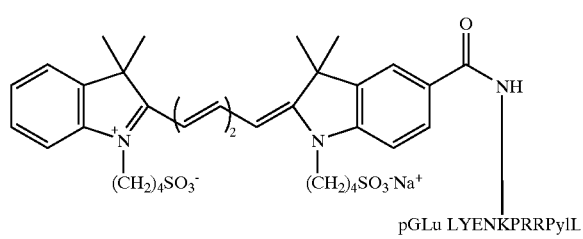

(ξ-amino-LYS[6]-indo-dicarbocyanine)-D-Tyr[11]-neurotensin-conjugate 36

EXAMPLES 37 TO 38

Conjugate of dyes 10–11 with D-Tyr[11]-neurotensin (5–13)-Cys (SEQ ID NO: 194)

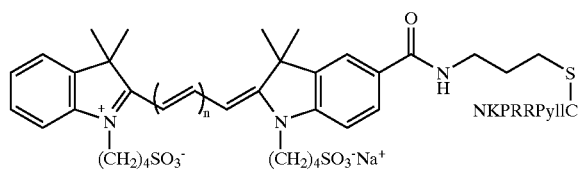

n=1: Indocarbocyanine-D-Tyr[11]-neurotensin (5–13)-Cys-conjugate 37
n=2: Indodicarbocyanine-D-Tyr[11]-neurotensin (5–13)-Cys-conjugate 38

EXAMPLE 39

Absorption and Fluorescence Properties of the Synthesized Dye-peptide Conjugates Absorption maxima and extinction coefficients were determined in PBS and in bovine plasma (Perkin Elmer Lambda 2). Fluorescence emission spectra were obtained in PBS by excitation on the short-wave side (about 40 nm from the absorption maximum) (SPEX Fluorolog, R928 PMT).

Figure 5:
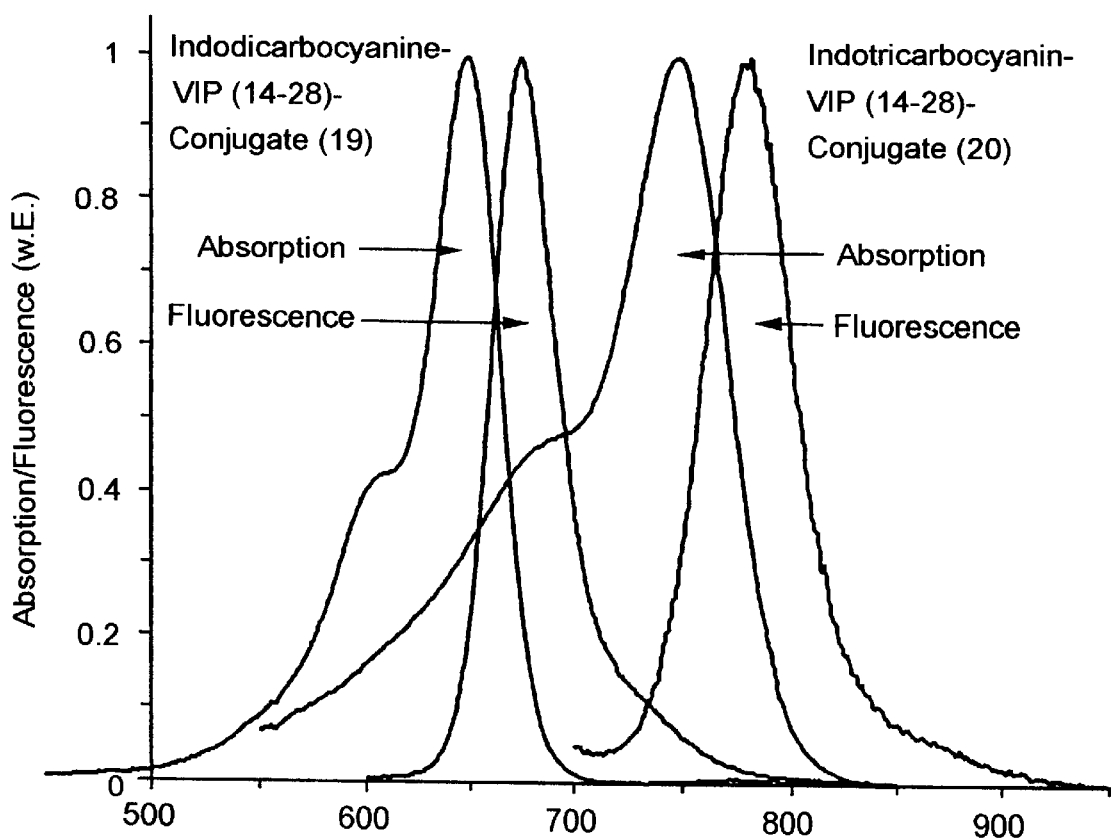
FIG. 5 shows the absorption and fluorescence spectra of the synthesized dye-peptide conjugates.

The absorption and fluorescence data are summarized in FIG. 4. In FIG. 5, typical absorption and fluorescence emission spectra are indicated by way of example.

EXAMPLE 40

Determination of the Cell Imaging Using Fluorescence Microscopy

The binding and imaging of the compounds according to the invention were studied in vitro in human tumor cells, and the receptors for vaso-active intestinal peptide and/or somatostatin and/or neurotensin were expressed. To this end, $5 \times 10^5$ tumor cells were incubated in 1.5 ml of medium, which contained the test substance. Different concentrations of the substances (10 nM–10 µM) were used, and the incubation period varied (1 minute–24 hours). After the incubation, the cells were set, and microscopic preparations were produced. The evaluation was carried out on a Zeiss Axiovert 135-fluorescence microscope, which was equipped with a Cy7-(Exciter HQ 710/70 nm, emitter 810/90 nm, beam splitter 750 nm LP), Cy5-(exciter 575–625 nm, emitter 660–710 nm BP, beam splitter 645 nm) and Cy3-filter set (exciter 546/12 nm, emitter 590 nm LP, beam splitter 580 nm). From all preparations, white light and fluorescence images were recorded with a CCD-camera (Visitron RTE/CCD-576) and digitally stored.

Selected results are described below:

Microscopic white light and fluorescence images (Cy7-filter set) of HT29 cells were set up after 30 minutes of incubation with 10 μM indotricarbocyanine-VIP (1–28)-conjugate 16. In the fluorescence image, a largely homogeneous fluorescence dispersed over the cells was detected. In addition, areas of increased signals were visible, which can be associated with vesicular compartments. The cells in the fluorescence image correlate in their spatial expansion with the white light image.

With the following compounds, white light and fluorescence images (Cy7-filter set) were obtained by analogous means:

Indotricarbocyanine-VIP (14–28)-conjugate 20, 10 μM, HT29-cells. Fluorescence dispersed homogeneously over the cells, good correlation with the white light image.

Indotricarbocyanine-retro-D-VIP (24–14) 25, 10 μM, HT29-cells. Fluorescence dispersed homogeneously over the cells, good correlation with the white light image.

Indotricarbocyanine-pentetreotide conjugate 30, 10 μM, RIN38-VIP1-cells. Fluorescence areas with a vesicular pattern in the membrane area of the cell, good correlation with the white light image.

In addition, fluorescence images were obtained by analogous means with the following compounds: (-amino-indotricarbocyanine)-Lys$^{25}$-VIP (14–25)-conjugate 24, 10 μM, RIN38-VIP1-cells, Cy7-filter set. The fluorescence image shows a homogeneous, intracellular near-nucleus fluorescence.

Indodicarbocyanine-VIP (1–28)-conjugate 15, 10 μM, RIN38-VIP1-cells, Cy5-filter set. The fluorescence image shows intracellular fluorescence areas with a vesicular pattern in the membrane area of the cell.

Indocarbocyanine-VIP (1–28)-conjugate 14, 10 μM, RIN38-VIP1-cells, Cy3-filter set. The fluorescence image shows intracellular fluorescence areas with a vesicular pattern in the membrane area of the cell.

EXAMPLE 41

Study of the Tumor Concentration Using In-vivo-fluorescence Imaging in Tumor-carrying Mice The imaging properties of the compounds according to the invention were studied in vivo after injection into tumor-carrying nude mice. To this end, 0.1 μmol/kg to 2 μmol/kg of the substance was administered intravenously, and the concentration in the tumor region was observed in a period from 0 to 48 hours. The fluorescence of the substances was excited by irradiation of animals with near-infrared light of wavelength 640 nm (indodicarbocyanines) or 740 nm (indotricarbocyanines), which was produced with an Nd:YAG laser. The fluorescence radiation was detected at a wavelength of >700 nm or >800 nm by an intensified CCD-camera, and the fluorescence images were stored digitally.

Selected results are described below:

From a tumor-carrying nude mouse (HT29-tumor in the right rear flank), whole-body-fluorescence images were recorded before and 1 hour after administration of 0.1 μmol/kg of indotricarbocyanine-VIP (14–28)-conjugate 20. The fluorescence intensity before administration is negligible (low autofluorescence). One hour after administration, a signal with approximately a 2-fold increase in intensity resulted in the tumor relative to the contralateral flank in fluorescence emission, whereby such emission is otherwise dispersed homogeneously over the remainder of the body.

From a tumor-carrying nude mouse (RIN38-SSTR2-tumor in the right rear flank), whole-body-fluorescence images were recorded before and one hour after administration of 0.1 μmol/kg of indotricarbocyanine-pentetreotide conjugate 30. The fluorescence intensity before administration is negligible (low autofluorescence). One hour after administration, a signal with approximately a 3-fold increase in intensity resulted in the tumor relative to the contralateral flank in fluorescence emission, whereby such emission is otherwise dispersed homogeneously over the remainder of the body.

From a tumor-carrying nude mouse (HT29 tumor in the right rear flank), whole-body-fluorescence images were recorded before and one hour after administration of 0.1 μmol/kg of (ξ-amino-indotricarbocyanine)-Lys$^{25}$-VIP (14–25)-conjugate 24. The fluorescence intensity before administration is negligible (low autofluorescence). One hour after administration, a signal with approximately a 1.5-fold increase in intensity resulted in the tumor relative to the contralateral flank. In addition, an increased fluorescence signal in the kidneys was detected.

From a tumor-carrying nude mouse (HT29-tumor in the right rear flank), whole-body-fluorescence images were recorded before and five minutes after administration of 0.2 μmol/kg of indodicarbocyanine-VIP (1–28)-conjugate 15. The fluorescence intensity before administration is negligible (low autofluorescence). One hour after administration, a signal with approximately a 1.4-fold increase in intensity resulted in the tumor relative to the contralateral flank. In addition, an increased fluorescence signal was detected in the kidneys.

EXAMPLE 42

Study of the Stability of Dye-peptide Conjugates in Bovine Plasma

The chemical stability of the compounds according to the invention in plasma was studied in vitro using HPLC based on time. To this end, 1 mM solutions of peptides in PBS in bovine blood plasma (Graeber Company, frozen, for heparin analysis) was pipetted while obtaining a concentration of 30 μM, and the solutions were incubated at 37° C.

At various times (0.5; 1; 2; 4; 6; 24 hours), the working-up of the samples was carried out by 1 ml of the plasma solution being mixed with 1 ml of MeOH, and the precipitated proteins being centrifuged off.

The analysis of the supernatant was carried out using HPLC by determining the content at 750 nm relative to the content after 1 minute of incubation at 0° C. (control)

HPLC: Beckmann, diode array detector TIDAS (J & M Company), 350–1000 nm;

Column: Chromasil 5μ, 250 mm×4.5 mm

Figure 6:
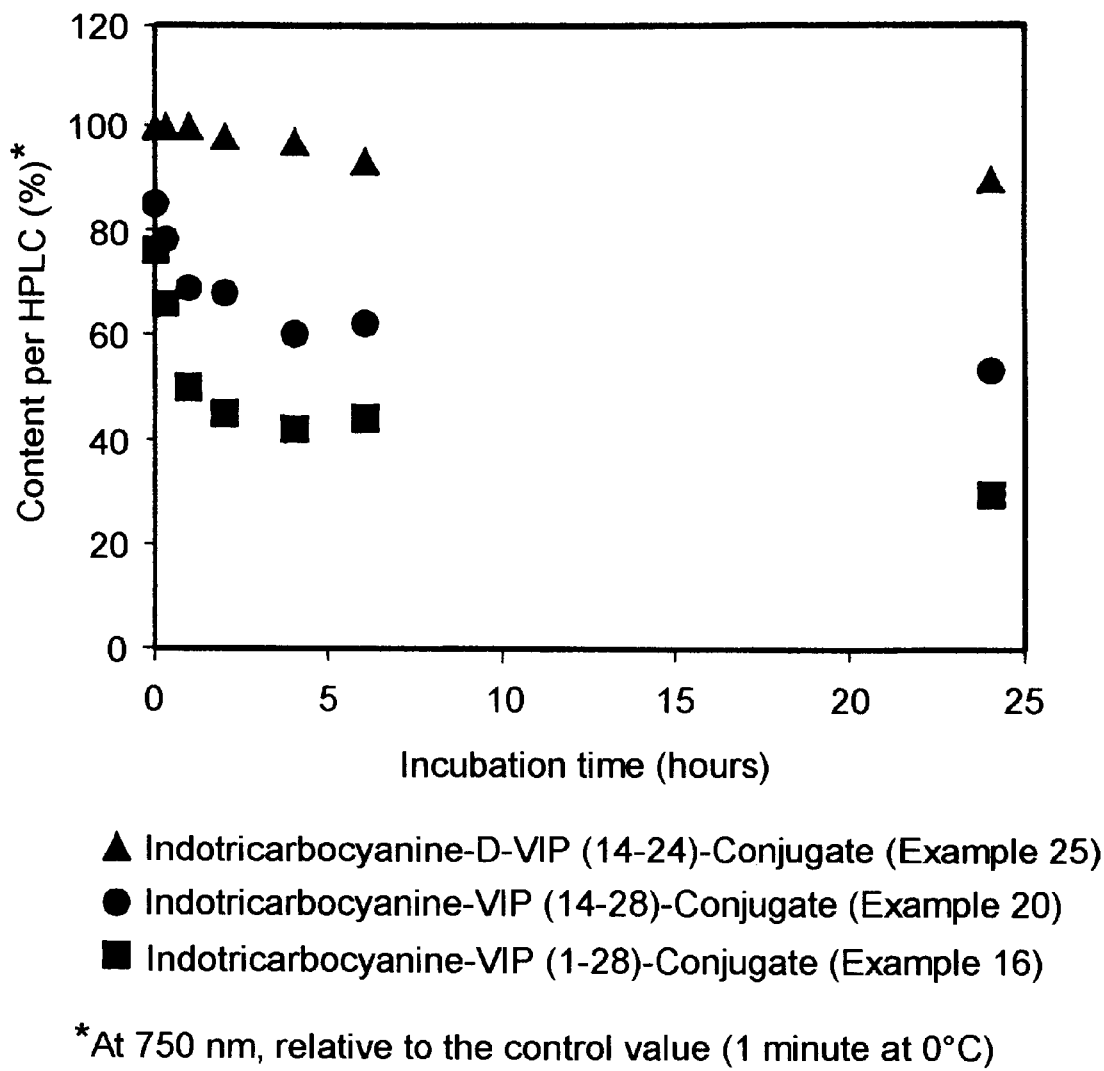
FIG. 6 shows the chemical stability of the dye conjugates with VIP-receptor-binding peptides in bovine plasma over a 24 hour in vitro time course using HPLC.

Mobile solvent:
 A: 90% H$_2$O (+0.5% TFA)/10% MeOH
 B: 10% H$_2$O (+0.5% TFA)/90% MeOH Gradient: 10% B to 100% B within 20-minutes The examples are summarized in FIG. 6.

EXAMPLE 43

Substitution Analysis of VIP Using Spot Synthesis

1. Synthesis of Peptides on Cellulose

The synthesis of peptides on cellulose (spot synthesis) was published in 1988 for the first time by R. Frank and R. Döring and described in detail in 1992 by R. Frank[1]. Here, the method[2] established in the AG Schneider-Mergener was used.

The cellulose membrane was chemically modified to provide suitable anchor functions for the subsequent peptide synthesis. In this case, a mercapto group[4] was inserted into an amino-functionalized cellulose membrane (CAPE membrane)[3]. The first amino acid in the form of a bromopropyl ester could be coupled to this mercapto group. Then, all amino acids of the peptide were successively built up according to the Fmoc strategy. At the end, the indodicarbocyanine solid was bonded in the N-terminal position to the peptide, and then all side protective groups were cleaved off.

To be able to study the peptides for receptor binding, the peptides had to be cleaved off from the cellulose. In this respect, a method was developed in which it has been possible for the first time to cleave off peptides with an authentic C-terminus from the cellulose.

1a. Modification of the cellulose membrane

A 20×30 cm cellulose membrane (Whatman 50) was incubated for 2 minutes with methanol/1.2% perchloroacetic acid and then freeze-dried.

After three hours of incubation with 10% epibromohydrin in dioxane/1.2% perchloroacetic acid, it was reacted for 30 minutes with methanol and then washed twice with methanol.

Then, it was washed three times with dimethylformamide (DMF) and incubated overnight with 50% 1,3-diaminopropane (v/v) in DMF. Then, it was washed as follows: 3×DMF, 2×ethanol, 2×distilled water, 2×ethanol, 15 minutes with 5 M sodium methanolate, 3×methanol, 4×distilled water, 3×ethanol, 1×diethyl ether.

1b. Definition of spots

For the spot definition, 1.3 µl of 0.6 M Fmoc-β-alanine-Opfp solution with the auto-spot robot 222×L (Abimed, Langenfeld) was doubly-pipetted at a reaction time of 15 minutes to certain points on the cellulose membrane.

The membrane was acetylated for 2 minutes with 2% acetic anhydride solution and for 30 minutes with 20% acetic anhydride/10% diisopropylethylamine.

For the cleavage of the Fmoc-protective group, the membrane was washed 3× with DMF, incubated 2× for 10 minutes with 20% piperidine solution, and washed 5× with DMF and 1× with ethanol. The free amino groups could be made visible with bromophenolyl blue. After repeated washing with ethanol, the membrane was dried.

1c. Coupling of the Mmt-mercaptopropionic acid and the bromo-propylester 0.6 M mercaptopropionic acid was double-pipetted at a reaction time of 15 minutes to the defined spots. Then, it was washed 3× with DMF and 3× with dichloromethane (DCM).

The cleavage of the Mmt-protective group was carried out with incubation for 2 minutes with 10% dichloroacetic acid/0.5% trifluoroacetic acid and 3× for 5 minutes with 10% dichloroacetic acid/0.5% trifluoroacetic acid/5% triisobutylsilane. The following washing steps were performed: 1×DCM, 2×ethanol, 1×distilled water, 1–2 minutes with 10% cesium carbonate, 1×distilled water, 2×ethanol, 1×diethyl ether The respective Fmoc-bromopropyl-amino acid ester was coupled 3× at a concentration of 0.6 M and a reaction time of 15 minutes. The cleavage of the Fmoc-protective group was performed as in 1b.

1d. Coupling of the amino acids

The peptides were built up to form the spots by repeated pipetting of 0.6 M amino acid solutions in N-methylpyrrolidone and subsequent cleavage of the Fmoc-protective groups.

1e. Coupling of the indodicarbocyanine dye

An 0.3 M solution of the indodicarbocyanine dye was activated with 0.3 M TBTU and 0.6 M diisopropylethylamine, and it was pipetted 4× at a reaction time of 15 minutes to the spots.

1f. Cleavage of the side protective groups

The cleavage of the side protective groups was carried out by subsequent treatment of the membrane with 90% trifluoroacetic acid/3% triisobutylsilane/2% distilled water/1% phenol for 30 minutes and with 50% trifluoroacetic acid/3% triisobutylsilane/2% distilled water/1% phenol for 2.5 hours. Then, it was washed 4× with dichloromethane, 3× with DMF and 1× with ethanol.

2. Cleavage of the peptides from the cellulose-membrane

The spots were punched out and washed with methanol. For the cleavage, it was incubated for 30 minutes with 70 mM of sodium methanolate in methanol. It was possible to correct the pH by adding 37% hydrochloric acid. Then, the peptides were dried in a speed-vac.

After drying, the peptides were taken up in distilled water and analyzed using Reversed-Phase-HPLC and MALDI-TOF.

3. Cell assay and continuous-flow cytometry

The concentration of the VIP derivatives was determined photometrically via the dye. In the cell assay, the peptides were used with a final concentration of 150 mM. In this case, 1×10⁵ RIN38 (VAPC1) cells were incubated with the VIP derivatives for one hour at 37° C. in a binding buffer (50 mM of tris/HCL, pH 7.5, 5 nM of $MgCl_2$, 1 mM of $CaCl_2$, 100 mM of NaCl, 4% BSA)

Then, the cells were washed 2× with PBS, moved into the FACS-tube and centrifuged for 5 minutes at 377 g. The cell pellet was measured resuspended in 300 µl of Cellfix in the FACS-Calibur (Becton Dickinson) with an FL4-lens system.

4. Evaluation

The fluorescence intensities of the native, naturally occurring, human VIP-peptides measured in the continuous-flow cytometry were set at 100%. The standard deviation of 28 native VIP-peptides was 11%. The other VIP-derivatives were adapted to this 100%.

FIG. 7 shows relative fluorescence intensities of RIN38 VPAC1 cells after incubation in the presence of 150 nM of the dye-labeled peptides for 1 hour at 37° C. Data in percentage relative to the native peptide of the respective series.

Literature for spot synthesis:

1. Frank, R. (1992) Spot Synthesis: An Easy Technique for the Positionally Addressable, Parallel Chemical Synthesis on a Membrane Support. Tetrahedron 48, 9217–9232
2. Kramer, A.; Schneider-Mergener, J. (1998) Synthesis and Screening of Peptide Libraries on Continuous Cellulose Membrane Supports. Methods in Molecular Biology 87, 25–39
3. Volkmer-Engert, R.; Hoffman, B.; Schneider-Mergener, J. (1997) Tetrahedron Lett. 38, 1029–1032
4. Licha, K.; Bhargava, S.; Rheinlander, C.; Becker, A.; Schneider-Mergener, J.; Volkmer-Engert, R. (in press) Highly Parallel Nano-Synthesis of Cleavable Peptide-Dye Conjugates on Cellulose Membranes. Tetrahedron Lett.

EXAMPLE 44 a) 5-N-(2,3-Dihydroxypropyl)aminocarbonyl-1-(4-sulfobutyl)-2,3,3-trimethyl(3H)indolenine 0.9 g (2.6 mmol) of 5-carboxy-1-(4-sulfobutyl)-2,3,3-trimethyl(3H)indolenine (Anal. Biochem. 217, 197, 1994) is introduced into 30 ml of absolute N,N-dimethylformamide and 3 ml of pyridine and mixed with 1.35 g (5.3 mmol) of disuccinimidyl carbonate. After three hours, 0.965 g (10.6 mmol) of 2,3-dihydroxypropylamine is added. It is stirred overnight at room temperature, the batch is evaporated to the dry state, and the residue is absorptively precipitated with diethyl ether. The solid is suctioned off and chromatographed on RP-material for purification.

Yield: 0.82 g (76% of theory)

Analysis (relative to solventless substance): Cld: C, 55.32; H, 6.84; N, 6.79; S, 7.77; O, 23.27. Fnd: C, 55.39; H, 6.95; N, 6.57; S, 7.58.

b) 4-[2-[4-Chloro-7-[5-N-(dihydroxypropyl) aminocarbonyl-3,3-dimethyl-1-(4-sulfonatobutyl) indolin-2-ylidene]-3,5-(propane-1,3-diyl)-1,3,5-heptatrien-1-yl]-5-N-(dihydroxypropyl) aminocarbonyl-3,3-dimethyl(3H)-indolio]-butanesulfonate, sodium salt A solution of 360 mg (1 mmol) of N-[5-anilino-3-chloro-2,4-(propane-1,3-diyl)-2,4-pentadien-1-ylidene]anilinium-chloride, 825 mg (2 mmol) of 5-N-(2,3-dihydroxypropyl) aminocarbonyl-1-(4-sulfobutyl)-2,3,3-trimethyl(3H) indolenine (Example 44a) and 330 mg (4 mmol) of anhydrous sodium acetate in 30 ml of ethanol are refluxed for two hours under argon. Then, the ethanol is distilled off, and the residue is purified by chromatography.

Yield: 0.58 g (59% of theory)

Analysis (relative to solventless substance): Cld: C, 56.17; H, 6.15; Cl, 3.60; N, 6.79; S, 7.77; O, 23.27; Na, 2.34. Fnd: C, 55.99; H, 6.30; Cl, 3.41; N, 6.87; S, 7.64; Na; 2.17.

c) 4-[2-[4-(4-(2-Carboxyethyl)phenyloxy)-7-[5-N-(dihydroxypropyl)aminocarbonyl-3,3-dimethyl-1-(4-sulfonatobutyl)indolin-2-ylidene]-3,5-(propane-1,3-diyl)-1,3,5-heptatrien-1-yl]-5-N-(dihydroxypropyl) aminocarbonyl-3,3-dimethyl(3H)indolio] butanesulfonate, sodium salt, N-hydroxysuccinimide ester 225 mg (1.4 mmol) of 3-(4-hydroxyphenyl)propionic acid is dissolved in 10 ml of dry N,N-dimethylformamide under a cover gas and mixed with 65 mg (2.7 mmol) of sodium hydride (60% in oil). After 30 minutes, 138 mg (0.14 mmol) of 4-[2-[4-chloro-7-[5-N-(dihydroxypropyl)aminocarbonyl-3,3-dimethyl-1-(4-sulfonatobutyl)indolin-2-ylidene]-3,5-(propane-1,3-diyl)-1,3,5-heptatrien-1-yl]-5-N-(dihydroxypropyl)aminocarbonyl-3,3-dimethyl(3H)indolio] butanesulfonate, sodium salt (Example 44b), is added, and it is stirred-for another 30 minutes. Then, the reaction mixture is quenched with dry ice and evaporated to the dry state. The residue is purified-via a preparative HPLC. For production of the active ester, 14 mg (120 µmol) of N-hydroxysuccinimide and 2 mg (2.4 µmol) of the carboxylic acid are dissolved in 200 µl of N,N-dimethylformamide. After ten minutes, 24 mg (120 µmol) of dicyclohexylcarbodiimide is added, and it is stirred overnight at room temperature. The active ester is used without further purification in the next step. Analogously to the synthesis according to Examples 14–16 and 18–27a (solid-phase peptide synthesis), the VIP-analog HSDAVFWDNY TRLRKQMAVK KYLNSILN(SEQ ID NO: 90) is synthesized in the solid phase. The dye 4-[2-[4-(4-(2-carboxyethyl)-phenyloxy)-7-[5-N-(dihydroxypropyl)aminocarbonyl-3,3-dimethyl-1-(4-sulfonatobutyl)indolin-2-ylidene]-3,5-(propane-1,3-diyl)-1,3,5-heptatrien-1-yl]-5-N-(dihydroxypropyl)aminocarbonyl-3,3-dimethyl(3H)indolio]-butanesulfonate, sodium salt, is coupled to the peptide according to Examples 14–16 and 18–27b (dye coupling), and this conjugate is isolated and purified according to Examples 14–16 and 18–27c (protective group cleavage and detachment of the dye-peptide conjugates).

d) 4-[2-[4-(4-(2-Isothiocyanatoethyl)phenyloxy)-7-[5-N-(dihydroxypropyl)aminocarbonyl-3,3-dimethyl-1-(4-sulfonatobutyl)indolin-2-ylidene]-3,5-(propane-1,3-diyl)-1,3,5-heptatrien-1-yl]-5-N-(dihydroxypropyl)aminocarbonyl-3,3-dimethyl(3H) indolio]butanesulfonate, sodium salt 116 mg (0.6 mmol) of 2-(4-hydroxyphenyl) ethylisothiocyanate in 2 ml of N,N-dimethylformamide is added to a suspension of 28 mg (0.6 mmol) of sodium hydride (60% in oil) in 4 ml of anhydrous N,N-dimethylformamide at 0° C. After 30 minutes, the solution that is thus produced is added to 138 mg (0.14 mmol) of 4-[2-[4-chloro-7-[5-N-(dihydroxypropyl)aminocarbonyl-5-N-(dihydroxypropyl)aminocarbonyl-3,3-dimethyl-1-(4-sulfonatobutyl)indolin-2-ylidene]-3,5-(propane-1,3-diyl)-1,3,5-heptatrien-1-yl]-3,3-dimethyl(3H)indolio] butanesulfonate, sodium salt (Example 44b). It is stirred overnight at room temperature and then quenched with dry ice. It is evaporated to the dry state in a rotary evaporator, and the residue is purified via preparative HPLC.

Yield: 85 mg (54% of theory)

Analysis: (relative to solventless substance):

| Cld: | C 58.55 | H 6.09 | N 6.22 | S 8.54 | O 18.47 | Na 2.04 |
| --- | --- | --- | --- | --- | --- | --- |
| Fnd: | C 58.53 | H 6.17 | N 6.11 | S 8.63 | | Na 1.83 |

Analogously to the synthesis according to Examples 14–16 and 18–27a (solid-phase peptide synthesis), the VIP-analog HSDAVFTDNY TRLRFQMAVK KYLNSILN(SEQ ID.Nb: 94) is synthesized in the solid phase. The dye 4-[2-[4-(4-(2-isothiocyanatoethyl)-phenyloxy)-7-[5-N-(dihydroxypropyl)aminocarbonyl-3,3-dimethyl-1-(4-sulfonatobutyl)indolin-2-ylidene]-3,5-(propane-1,3-diyl)-1,3,5-heptatrien-1-yl]-5-N-(dihydroxypropyl)aminocarbonyl-3,3-dimethyl(3H)indolio]-butanesulfonate, sodium salt, is coupled to the peptide in the N-terminal position, and this conjugate is isolated and purified according to Examples 14–16 and 18–27c (protective group cleavage and detachment of the dye-peptide conjugates)

Analogously, other symmetrically hydrophilic dyes can be built up from the following components:

Hydrophilic indolenine derivatives with hydroxyalkyl substituents: (produced according to Example 44a)

a) 5-N-(2,3-Dihydroxypropyl)-N-methylaminocarbonyl-1-(4-sulfobutyl)-2,3,3-trimethyl(3H)indolenine
b) 5-N-(Hydroxyethyl)-aminocarbonyl-1-(4-sulfobutyl)-2,3,3-trimethyl(3H)indolenine
c) 5-N-(2.3-Dihydroxypropyl)-N-(hydroxyethyl)-aminocarbonyl-1-(4-sulfobutyl)-2,3,3-trimethyl(3H) indolenine
d) 5-N,N-(bis-Hydroxyethyl)-aminocarbonyl-1-(4-sulfobutyl)-2,3,3-trimethyl(3H)indolenine
e) 5-N-(2,3,4,5,6-Pentahydroxyhexyl)-aminocarbonyl-1-(4-sulfobutyl)-2,3,3-trimethyl(3H)indolenine
f) 5-N-(1,3,4-Trihydroxybut-2-yl)-N-methylaminocarbonyl-1-(4-sulfobutyl)-2,3,3-trimethyl(3H)indolenine

EXAMPLE 45 a) 5-N-(2,3,4,5,6-Pentahydroxyhexyl) aminocarbonyl-1-(4-sulfobutyl)-2,3,3-trimethyl(3H) indolenine 0.6 g (1.8 mmol) of 5-carboxy-1-(4-sulfobutyl)-2,3,3-trimethyl(3H)indolenine (Anal. Biochem. 217, 197, 1994) is introduced into 20 ml of absolute N,N-dimethylformamide and 2 ml of pyridine, and it is mixed with 0.95 g (3.6 mmol) of disuccinimidyl carbonate. After two hours, 1.4 ml (10 mmol) of triethylamine and 322 mg (1.8 mmol) of glucamine are added. It is stirred overnight at room temperature, the batch is evaporated to the dry state, and the residue is absorptively precipitated with diethyl ether. The solid is suctioned off and chromatographed on RP-material for purification.

Yield: 0.67 g (74w of theory)

Analysis (relative to solventless substance):

| Cld: | C 52.58 | H 6.82 | N 5.57 | S 6.38 | O 28.65 |
|---|---|---|---|---|---|
| Fnd: | C 52.47 | H 6.91 | N 5.39 | S 6.44 | | b) 4-[2-[4-Chloro-7-[5-N-(2,3,4,5,6-pentahydroxyhexyl)aminocarbonyl-3,3-dimethyl-1-(4-sulfonatobutyl)indolin-2-ylidene]-3,5-(propane-1,3-diyl)-1,3,5-heptatrien-1-yl]-3,3-dimethyl5-[N-(2,3,4,5,6-pentahydroxyhexyl)aminocarbonyl](3H)indolio]butanesulfonate, sodium salt A solution of 180 mg (0.5 mmol) of N-[5-anilino-3-chloro-2,4-(propane-1,3-diyl)-2,4-pentadien-1-ylidene]anilinium-chloride, 503 mg (1 mmol) of 5-N-(2,3,4,5,6-pentahydroxyhexyl)aminocarbonyl-1-(4-sulfobutyl)-2,3,3-trimethyl(3H)indolenine (Example 45a), and 165 mg (2 mmol) of anhydrous sodium acetate in 10 ml of ethanol are refluxed for two hours under argon. Then, the ethanol is distilled off, and the residue is purified by chromatography.

Yield: 0.31 g (53% of theory)

Analysis (relative to solventless substance):

| Cld: | C 54.05 | H 6.33 | Cl 3.01 | N 4.76 | S 5.44 | O 24.45 | Na 1.95 |
|---|---|---|---|---|---|---|---|
| Fnd: | C 53.89 | H 6.20 | Cl 2.87 | N 4.83 | S 5.29 | | Na 1.72 | c) 4-[2-[4-(4-Isothiocyanatothiophenyloxy)-7-[5-N-(2,3,4,5,6-pentahydroxyhexyl)aminocarbonyl-3,3-dimethyl-1-(4-sulfonatobutyl)indolin-2-ylidene]-3,5-(propane-1,3-diyl)-1,3,5-heptatrien-1-yl]-3,3-dimethyl-5-[N-(2,3,4,5,6-pentahydroxyhexyl)aminocarbonyl](3H)indolio]butanesulfonate, sodium salt 54 mg (0.4 mmol) of 4-aminothiophenol is dissolved in 10 ml of absolute N,N-dimethylformamide under argon atmosphere and mixed at room temperature with 165 mg (0.14 mmol) of 4-[2-[4-chloro-7-[5-N-(2,3,4,5,6-pentahydroxyhexyl)aminocarbonyl-3,3-dimethyl-1-(4-sulfonatobutyl)indolin-2-ylidene]-3,5-(propane-1,3-diyl)-1,3,5-heptatrien-1-yl]-3,3-dimethyl-5-[N-(2,3,4,5,6-pentahydroxyhexyl)aminocarbonyl](3H)indolio]butanesulfonate, sodium salt (Example 45b). After 10 minutes, the reaction mixture is quenched with dry ice, and 210 mg (1 mmol) of thiocarbonyldiimidazole is added. After 45 minutes, the dye is precipitated with diethyl ether, and the solid is isolated via centrifuging. For purification, it is can be chromatographed on RP-material.

Yield: 78 mg (43% of theory)

Analysis (relative to solventless substance):

| Cld: | C 55.07 | H 6.01 | N 5.35 | S 9.80 | O 22.01 | Na 1.76 |
|---|---|---|---|---|---|---|
| Fnd: | C 54.89 | H 6.20 | N 5.24 | S 9.58 | | Na 1.54 |

Analogously to the synthesis according to Examples 14–16 and 18–27a (solid-phase peptide synthesis), the VIP-analog HSWAVFTDNY TRLRKQMAVK KYLNSILN(SEQ ID NO: 73) is synthesized in the solid phase. The dye 4-[2-[4-(4-isothiocyanatothiophenyloxy)-7-[5-N-(2,3,4,5,6-pentahydroxyhexyl)-aminocarbonyl-3,3-dimethyl-1-(4-sulfonatobutyl)indolin-2-ylidene]-3,5-(propane-1,3-diyl)-1,3,5-heptatrien-1-yl]-3,3-dimethyl-5-[N-(2,3,4,5,6-pentahydroxyhexyl)aminocarbonyl](3H)indolio]butanesulfonate, sodium salts is coupled to the peptide in the N-terminal position, and this conjugate is isolated and purified according to Examples 14–16 and 18–27c (protective group cleavage and detachment of the dye-peptide conjugates).

Analogously, other symmetrical hydrophilic dyes can be built up from the following components:

Hydrophilic indolenine derivatives with hydroxyalkyl substituents: (produced according to Example 44a)

a) 5-N-(2,3-Dihydroxypropyl)-N-methylaminocarbonyl-1-(4-sulfobutyl)-2,3,3-trimethyl(3H)indolenine
b) 5-N-(Hydroxyethyl)-aminocarbonyl-1-(4-sulfobutyl)-2,3,3-trimethyl(3H)indolenine
c) 5-N-(2,3-Dihydroxypropyl)-N-(hydroxyethyl)-aminocarbonyl-1-(4-sulfobutyl)-2,3,3-trimethyl(3H)indolenine
d) 5-N,N-(bis-Hydroxyethyl)-aminocarbonyl-1-(4-sulfobutyl)-2,3,3-trimethyl(3H)indolenine
e) 5-N-(2,3,4,5,6-Pentahydroxyhexyl)-aminocarbonyl-1-(4-sulfobutyl)-2,3,3-trimethyl(3H)indolenine
f) 5-N-(1,3,4-Trihydroxybut-2-yl)-N-methylaminocarbonyl-1-(4-sulfobutyl)-2,3,3-trimethyl(3H)-indolenine

EXAMPLE 46

7[5-N-(2,3-Dihydroxypropyl)aminocarbonyl-3,3-dimethyl-1-(4-sulfonatobutyl)indolin-2-ylidene]-1,3,5-heptatrien-1-yl]-3,3-dimethyl-5-carboxy(3H)indolio]butanesulfonate, sodium salt A solution of 2.35 g (5.71 mmol) of 5-N-(2,3-dihydroxypropyl)aminocarbonyl-1-(4-sulfobutyl)-2,3,3-trimethyl(3H)indolenine (Example 44a) and 1.57 g (5.5 mmol) of glutaconaldehyde dianilide-hydrochloride in 25 ml of acetic acid anhydride are stirred for 30 minutes at 120° C. Then, 2.4 g (7.1 mmol) of 5-carboxy-1-(4-sulfobutyl)-2,3,3-trimethyl(3H)-indolenine, 1.71 g of sodium acetate, 22 ml of acetic acid anhydride and 8.6 ml of acetic acid are added. The reaction mixture is allowed to stir for one hour at 120° C., cooled to room temperature, and the product is precipitated with diethyl ether. The crude product is chromatographed on RP-material.

Yield: 1.9 g (40% of theory)

Analysis (relative to solventless substance):

| Cld: | C 54.47 | H 6.03 | N 5.03 | S 7.67 | O 21.05 | Na 2.75 |
|---|---|---|---|---|---|---|
| Fnd: | C 54.26 | H 6.12 | N 5.00 | S 7.49 | | Na 2.48 |

Analogously to the synthesis according to Examples 14–16 and 18–27a (solid-phase peptide synthesis), the VIP-analog HSDAVFTDNY TRLRKKMAVK KYLNSILN (SEQ ID NO: 101) is synthesized in the solid phase. The dye 7-[5-N-(2,3-dihydroxypropyl)aminocarbonyl-3,3-dimethyl-1-(4-sulfonatobutyl)indolin-2-ylidene]-1,3,5-heptatrien-1-yl]-3,3-dimethyl-5-carboxy(3H)indolio]butanesulfonate, sodium salt, is coupled to the peptide in the N-terminal position according to Examples 14–16 and 18–27b (dye coupling), and this conjugate is isolated and purified using HPLC according to Examples 14–16 and 18–27c (protective group cleavage and detachment of the dye-peptide conjugate).

Analogously, other unsymmetrical hydrophilic dyes can be built up from the following components:

Hydrophilic indolenine derivatives with hydroxyalkyl substituents: (produced according to Example 44a)

a) 5-N-(2,3-Dihydroxypropyl)-N-methylaminocarbonyl-1-(4-sulfobutyl)-2,3,3-trimethyl(3H)indolenine
b) 5-N-(Hydroxyethyl)-aminocarbonyl-1-(4-sulfobutyl)-2,3,3-trimethyl(3H)indolenine
c) 5-N-(2,3-Dihydroxypropyl)-N-(hydroxyethyl)-aminocarbonyl-1-(4-sulfobutyl)-2,3,3-trimethyl(3H)indolenine
d) 5-N,N-(bis-Hydroxyethyl)-aminocarbonyl-1-(4-sulfobutyl)-2,3,3-trimethyl(3H)indolenine
e) 5-N-(2,3,4,5,6-Pentahydroxyhexyl)-aminocarbonyl-1-(4-sulfobutyl)-2,3,3-trimethyl(3H)indolenine
f) 5-N-(1,3,4-Trihydroxybut-2-yl)-N-methylaminocarbonyl-1-(4-sulfobutyl)-2,3,3-trimethyl(3H)indolenine Indolenine derivatives with carboxyl groups:

a) 5-Carboxy-1-(4-sulfobutyl)-2,3,3-trimethyl(3H)indolenine
b) 5-Carboxymethyl-1-(4-sulfobutyl)-2,3,3-trimethyl(3H)indolenine
c) 5-Carboxy-1-(3-sulfopropyl)-2,3,3-trimethyl(3H)indolenine
d) 5-Carboxymethyl-1-(3-sulfopropyl)-2,3,3-trimethyl(3H)indolenine
e) 5-Carboxy-1-(2-sulfoethyl)-2,3,3-trimethyl(3H)indolenine
f) 5-Carboxymethyl-1-(2-sulfoethyl)-2,3,3-trimethyl(3H)indolenine Dianil derivatives for reaction with the above-mentioned indolenines with the formation of mono-, di- or tricarbocyanines:

a) Glutaconaldehyde dianilide-hydrochloride
b) Malonaldehyde-bis-phenylimine-hydrochloride
c) N,N-Diphenylformamidine
d) N-[5-Anilino-2,4-(propane-1,3-diyl)-2,4-pentadien-1-ylidene]anilinium-chloride
e) N-[5-Anilino-2,4-(ethane-1,2-diyl)-2,4-pentadien-1-ylidene]anilinium-chloride
f) N-[5-Anilino-3-chloro-2,4-(propane-1,3-diyl)-2,4-pentadien-1-ylidene]anilinium chloride
g) N-[5-Anilino-3-chloro-2,4-(ethane-1,2-diyl)-2,4-pentadien-1-ylidene]anilinium chloride

EXAMPLE 47

7-[5-N-(1,3,4-Trihydroxybut-2-yl)-aminocarbonyl-3,3-dimethyl-1-(4-sulfonatobutyl)indolin-2-ylidene]-3,5-(2-carboxypropane-1,3-diyl)-1,3,5-heptatrien-1-yl]-3,3-dimethyl-5-N-(1,3,4-trihydroxybut-2-yl)-aminocarbonyl(3H)indolio]butanesulfonate, sodium salt, N-hydroxysuccinimide ester a) 4-[2-[4-Chloro-7-[5-N-(1,3,4-trihydroxybut-2-yl)aminocarbonyl-3,3-dimethyl-1-(4-sulfonatobutyl)indolin-2-ylidine]-3,5-[2-(methoxycarbonyl)propane-1,3-diyl]-1,3,5-heptatrien-1-yl]-3,3-dimethyl-5-[N-(1,3,4-trihydroxybut-2-yl)aminocarbonyl](3H)indolio]butanesulfonate, sodium salt 5.5 ml (10 mmol) of phosphoroxy chloride and 6 ml of N,N-dimethylformamide are added to a solution of 0.8 g (5 mmol) of 4-(methoxycarbonyl)-cyclohexanone in 5 ml of dichloromethane at 0° C. Then, it is refluxed for one hour. The dichloromethane is distilled off, and 4 ml of aniline in 10 ml of methanol is added at a maximum of 5° C. The reaction mixture is poured onto ice, 5 ml of concentrated hydrochloric acid is added, and the intermediate product is allowed to crystallize out for five hours at 0° C. The crystals are suctioned off, and the latter are used without further purification in the next reaction. To this end, the crystals are dissolved in anhydrous ethanol, and 4.4 g (10 mmol) of 5-N-(1,3,4-trihydroxybut-2-yl)-N-methylaminocarbonyl-1-(4-sulfobutyl)-2,3,3-trimethyl(3H)indolenine (see Example 45) and 0.8 g of anhydrous sodium acetate are added. It is refluxed for one hour, the solid is filtered off, and the filtrate is evaporated to the dry state. The residue is chromatographed for purification.

Yield: 3.25 g (58% of theory)

Analysis (relative to solventless substance):

| | | | | | | | |
|---|---|---|---|---|---|---|---|
| Cld: | C 54.90 | H 6.14 | Cl 3.18 | N 5.02 | S 5.75 | O 22.94 | Na 2.06 |
| Fnd: | C 54.76 | H 6.03 | Cl 2.99 | N 4.91 | S 5.60 | | Na 1.83 | b) 7-[5-N-(1,3,4-Trihydroxybut-2-yl)aminocarbonyl-3,3-dimethyl-1-(4-sulfonatobutyl)indolin-2-ylidene]-3,5-(2-carboxypropane-1,3-diyl)-1,3,5-heptatrien-1-yl]-3,3-dimethyl-5-N-(1,3,4-trihydroxybut-2-yl)aminocarbonyl(3H)indolio]butanesulfonate, sodium salt A mixture of 10 mg (0.4 mmol) of sodium hydride and 80 mg (1.3 mmol) of ethanethiol in 10 ml of anhydrous N,N-dimethylformamide are stirred under nitrogen for 30 minutes at room temperature. Then, it is mixed with 112 mg (0.1 mmol) of 4-[2-[4-chloro-7-[5-N-(2,3,4,5,6-pentahydroxyhexyl)aminocarbonyl-3,3-dimethyl-1-(4-sulfonatobutyl)indolin-2-ylidene]-3,5-[2-(methoxycarbonyl)propane-1,3-diyl]-1,3,5-heptatrien-1-yl]-3,3-dimethyl5-[N-(2,3,4,5,6-pentahydroxyhexyl)-aminocarbonyl](3H)indolio]butanesulfonate, sodium salt (Example 47a), in 3 ml of N,N-dimethylformamide. The reaction mixture is heated for two hours to 100° C. and after cooling to room temperature, it is quenched with carbon dioxide. It is evaporated to the dry state in a rotary evaporator, and the residue is extracted with hot ethanol. The extract is evaporated, and the crude product is chromatographed.

Yield: 75 mg (67% of theory)
Analysis (relative to solventless substance):

| Cld: | C 56.27 | H 6.33 | N 5.25 | S 6.01 | O 23.99 | Na 2.15 |
|---|---|---|---|---|---|---|
| Fnd: | C 56.13 | H 6.46 | N 5.12 | S 5.87 | | Na 1.88 | c) 7-[5-N-(1,3,4-Trihydroxybut-2-yl)-aminocarbonyl-3,3-dimethyl-1-(4-sulfonatobutyl)indolin-2-ylidene]-3,5-(2-carboxypropane-1,3-diyl)-1,3,5-heptatrien-1-yl]-3,3-dimethyl-5-(N-(1,3,4-trihydroxybut-2-yl)-aminocarbonyl(3H)indolio]butanesulfonate-N-hydroxysuccinimide ester, sodium salt For the production of the active ester, 14 mg (0.12 mmol) of N-hydroxysuccinimide and 64 mg (0.06 mmol) of the carboxylic acid in 2 ml of N,N-dimethylformamide are dissolved. After 15 minutes, 25 mg (0.12 mmol) of dicyclohexylcarbodiimide is added, and it is stirred overnight at room temperature. The active ester is purified using preparative HPLC.

Yield: 60 mg (86% of theory)
Analysis (relative to solventless substance):

| Cld: | C 55.71 | H 6.06 | N 6.02 | S 5.51 | O 24.73 | Na 1.97 |
|---|---|---|---|---|---|---|
| Fnd: | C 55.59 | H 6.21 | N 5.93 | S 5.37 | | Na 1.75 |

Analogously to the synthesis according to Examples 14–16 and 18–27a (solid-phase peptide synthesis), the VIP-analog HSDAVFTDNY TRLRKAMAVK KYLNSILN(SEQ ID NO: 98) is synthesized in the solid phase. The dye 7-[5-N-(1,3,4-trihydroxybut-2-yl)-aminocarbonyl-3,3-dimethyl-1-(4-sulfonatobutyl)indolin-2-ylidene]-3,5-(2-carboxypropane-1,3-diyl)-1,3,5-heptatrien-1-yl]-3,3-dimethyl-5-N-(1,3,4-trihydroxybut-2-yl)-aminocarbonyl(3H)indoliolbutanesulfonate, sodium salt, is coupled to the peptide in the N-terminal position according to Examples 14–16 and 18–27b, and this conjugate is isolated and purified according to Examples 14–16 and 18–27c (protective group cleavage and detachment of the dye-peptide conjugates).

EXAMPLE 48

7-[5-N-(1,3,4-Trihydroxybut-2-yl)-aminocarbonyl-3,3-dimethyl-1-(4-sulfonatobutyl)indolin-2-ylidene]-3,5-(2-carboxypropane-1,3-diyl)-1,3,5-heptatrien-1-yl]-3,3-dimethyl-5-N-(1,3,4-trihydroxybut-2-yl)-aminocarbonyl(3H)indolio]butanesulfonate, sodium salt a) 5-N-(11-Aminoundecyl)aminocarbonyl-1-(4-sulfobutyl)-2,3,3-trimethyl(3H)indolenine 340 mg (1 mmol) of 5-carboxy-1-(4-sulfobutyl-l)-2,3,3-trimethyl(3H)indolenine (Anal. Biochem. 217, 197, 1994) is introduced into 5 ml of absolute N,N-dimethylformamide and 1 ml of pyridine, and it is mixed with 0.5 g (2 mmol) of disuccinimidyl carbonate. After three hours, 0.805 g (4 mmol) of 11-aminoundecanoic acid is added. It is stirred overnight at room temperature, the batch is evaporated to the dry state, and the residue is absorptively precipitated with diethyl ether. The solid is suctioned off and chromatographed on RP-material for purification.

Yield: 0.37 g (71% of theory)
Analysis (relative to solventless substance):

| Cld: | C 62.04 | H 8.10 | N 5.36 | S 6.13 | O 18.37 |
|---|---|---|---|---|---|
| Fnd: | C 61.88 | H 8.23 | N 5.17 | S 6.02 | | b) 7-[5-N-(1,3,4-Trihydroxybut-2-yl)-aminocarbonyl-3,3-dimethyl-1-(4-sulfonatobutyl)indolin-2-ylidene]-3,5-(2-carboxypropane-1,3-diyl)-1,3,5-heptatrien-1-yl]-3,3-dimethyl-5-N-(1,3,4-trihydroxybut-2-yl)-aminocarbonyl-(3H)indolio]butanesulfonate, sodium salt A solution of 0.35 g (0.67 mmol) of 5-N-(11-aminoundecyl)aminocarbonyl-1-(4-sulfobutyl)-2,3,3-trimethyl(3H)indolenine (Example 48a) and 0.18 g (0.645 mmol) of glutaconaldehyde dianil in 3 ml of acetic acid anhydride is stirred for 20 minutes at 110° C. Then, 344 mg (0.83 mmol) of 5-N-(2,3-dihydroxypropyl)-aminocarbonyl-1-(4-sulfobutyl)-2,3,3-trimethyl(3H)indolenine (Example 44a), 0.2 g of sodium acetate, 3 ml of acetic acid anhydride and 1 ml of acetic acid are added. The reaction mixture is allowed to stir for two hours at 110° C., cooled to room temperature, and the product is precipitated with diethyl ether. The crude product is chromatographed on RP-material.

Yield: 0.41 g (60% of theory)
Analysis (relative to solventless substance):

| Cld: | C 60.10 | H 7.02 | N 5.50 | S 6.29 | O 18.84 | Na 2.26 |
|---|---|---|---|---|---|---|
| Fnd: | C 59.96 | H 7.14 | N 5.33 | S 6.15 | | Na 2.11 |

Analogously to the synthesis according to Examples 14–16 and 18–27a (solid-phase peptide synthesis), the VIP-analog HSDAVFTDNY TRLRKQMWVK KYLNSILN(SEQ ID NO: 123) is synthesized in the solid phase. The dye 7-[5-N-(1,3,4-trihydroxybut-2-yl)-aminocarbonyl-3,3-dimethyl-1-(4-sulfonatobutyl)indolin-2-ylidene]-3,5-(2-carboxypropane-1,3-diyl)-1,3,5-heptatrien-1-yl]-3,3-dimethyl-5-N-(1,3,4-trihydroxybut-2-yl)-aminocarbonyl(3H)indolio]butanesulfonate, sodium salt, is coupled to the peptide in the N-terminal position according to Examples 14–16 and 18–27b, and this conjugate is isolated and purified according to Examples 14–16 and 18–27c (protective group cleavage and detachment of the dye-peptide conjugates).

Other dyes according to the invention can be produced according to Examples 44a and b, in which instead of 11-aminoundecanoic acid in Example 48a, the following amino acids are used, and the indolenine derivatives that are mentioned in Example 46 are used with hydroxyalkyl substituents a)–f):

i. Glycine
ii. Alanine
iii. β-Alanine
iv. 4-Aminobutanoic acid
v. 6-Aminohexanoic acid
vi. $H_2N-(CH_2CH_2O)_3CH_2COOH$ (TH 53, 20, 6977)
vii. $H_2N-(CH_2CH_2O)_4CH_2COOH$ (JOC 63, 5, 1728, 1998)
viii. $H_2N-C_2CH_2COO(CH_2CH_2O)_4-CO-C_2CH_2COOH$ (Lett. Pept. Sci. 6, 135, 1999)

ix. HCl*H₂N—PEG—COOH (MW 3400 g/mol; Shearwater Polymers Inc., USA

| | | | | | | | | | |
|---|---|---|---|---|---|---|---|---|---|
| Cld: | C 25.94 | H 5.22 | Cl 15.31 | Br 34.51 | N 12.10 | O 6.91 |
| Fnd: | C 25.76 | H 5.41 | Cl 15.55 | Br 34.34 | N 11.97 | |

EXAMPLE 49

4-[2-[4-(4-(N-(4-Aza-6-bromo-5-oxohexyl)aminocarbonylethyl)phenyloxy)-7-[5-N-(dihydroxypropyl)aminocarbonyl-3,3-dimethyl-1-(4-sulfonatobutyl)indolin-2-ylidene]-3,5-(propane-1,3-diyl)-1,3,5-heptatrien-1-yl]-5-N-(dihydroxypropyl)aminocarbonyl-3,3-dimethyl(3H)indolio]butanesulfonate, sodium salt a) [3-[N-(tert-Butoxycarbonyl)amino]propyl]-N-(bromoacetyl)-amide 2.5 g (14.4 mmol) of [3-[N-(tert-butoxycarbonyl)amino]propyl]amine is dissolved in 15 ml of dioxane, and after 4.4 ml of triethylamine is added at 0° C., it is mixed with 3.2 9 (16 mmol) of bromoacetyl bromide. It is stirred overnight at room temperature, and then another 320 mg of bromoacetyl bromide is added. After two hours at room temperature, the precipitate is suctioned off, the solution is concentrated by evaporation, and the residue is taken up in ethyl acetate. It is washed with water, and the organic phase is dried on sodium sulfate.

Yield: 3.2 g (75% of theory)

Analysis (relative to solventless substance):

| | | | | | |
|---|---|---|---|---|---|
| Cld: | C 40.69 | H 6.49 | Br 27.07 | N 9.49 | O 16.26 |
| Fnd: | C 40.50 | H 6.37 | Br 26.89 | N 9.58 | | b) (3-[N-(Bromoacetyl)amino]propyl]amine, hydrochloride 3.1 g (10.5 mmol) of [3-[N-(tert-butoxycarbonyl)amino]propyl]-N-(bromoacetyl)-amide (Example 49a) is stirred with 50 mmol. of 1M hydrochloric acid in ethyl acetate for five hours at room temperature. The product is suctioned off, and the solid is rewashed with ethyl acetate.

Yield: 2.3 g (95% of theory)

Analysis (relative to solventless substance):

c) 4-[2-[4-(4-(N-(4-Aza-6-bromo-5-oxo-hexyl)aminocarbonylethyl)phenyloxy)-7-[5-N-(dihydroxypropyl)amino-carbonyl-3,3-dimethyl-1-(4-sulfonatobutyl)indolin-2-ylidene]-3,5-(propane-1,3-diyl)-1,3,5-heptatrien-1-yl]-5-N-(dihydroxypropyl)aminocarbonyl-3,3-dimethyl(3H)indolio]butanesulfonate, sodium salt 121 mg (0.1 mmol) of 4-[2-[4-(4-(2-carboxyethyl)phenyloxy)-7-[5-N-(dihydroxypropyl)aminocarbonyl-3,3-dimethyl-1-(4-sulfonatobutyl)indolin-2-ylidene]-3,5-(propane-1,3-diyl)-1,3,5-heptatrien-1-yl]-5-N-(dihydroxypropyl)-aminocarbonyl-3,3-dimethyl(3H)indolio]butanesulfonate, sodium salt, N-hydroxysuccinimide ester (Example 44c) are dissolved in 0.5 ml of N,N-dimethylformamide, and mixed with 0.06 ml of triethylamine and 70 mg (0.3 mmol) of [3-[N-(bromoacetyl)amino]propyl]amine, hydrochloride (Example 49b).

It is stirred for four hours at 60° C., then cooled to room temperature, and the product is precipitated with diethyl ether. The solid is suctioned off and washed with ample diethyl ether.

Yield: 0.11 mg (80% of theory)

Analysis (relative to solventless substance):

| | | | | | | | |
|---|---|---|---|---|---|---|---|
| Cld: | C 56.17 | H 6.18 | Br 6.13 | N 6.44 | S 4.92 | Na 1.76 | O 18.40 |
| Fnd: | C 55.96 | H 6.26 | Br 6.01 | N 6.27 | S 4.81 | Na 1.53 | |

Analogously to the synthesis according to Examples 14–16 and 18–27a (solid-phase peptide synthesis), the VIP-analog HSDAVFTDNY TRLRKQCAVK KYLNSLLN(SEQ ID NO: 189) is synthesized in the solid phase. The dye bromide 4-[2-[4-(4-(N-(4-azα-6-bromo-5-oxo-hexyl)aminocarbonylethyl)phenyloxy)-7-[5-N-(dihydroxypropyl)aminocarbonyl-3,3-dimethyl-1-(4-sulfonatobutyl)indolin-2-ylidene]-3,5-(propane-1,3-diyl)-1,3,5-heptatrien-1-yl]-5-N-(dihydroxypropyl)amino-carbonyl-3,3-dimethyl(3H)indolio]butanesulfonate, sodium salt, is coupled to the peptide in the N-terminal position according to Example 17, and this conjugate is isolated and purified according to Examples 14–16 and 18–27c (protective group cleavage and detachment of the dye-peptide conjugates).

What is claimed is:

1. A peptide-polymethine-dye conjugate compound of formula (I):

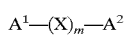

$$A^1-(X)_m-A^2 \quad \quad \text{I}$$

in which

X stands for an α-, β- or γ-amino acid with D- or L-configuration, and m stands for a number from 5 to 30, whereby the resulting amino acid sequence or peptide, $(X)_m$, is optionally cyclized in a straight-chain nature or via a disulfide bridge between two cysteines or homocysteines or amidically between the N- and C-terminus, and $(X)_m$ is an amino acid sequence of the vaso-active intestinal peptide (VIP), somatostatin or neurotensin and wherein any amino acid in the $(X)_m$ peptide may be interchanged with other natural or unnatural amino acids so long as the functional characteristics of the peptide-polymethine-dye conjugate remain unchanged.

$A^1$ is a hydrogen atom, an acetyl radical or an alkyl radical with 1 to 10 C-atoms, which is optionally substituted with 1 to 3 carboxy groups and/or 1 to 6 hydroxy groups, or a poly(oxyethylene) radical with 2 to 30 —$CH_2CH_2O$ units, or a dye molecule selected from polymethine dyes which have at least one absorption maximum in the range of 380 to 1200 nm, $A^2$ is a hydroxy group, an amino group or a dye molecule selected from polymethine dyes which have at least one absorption maximum in the range of 380 to 1200 nm, under the condition that at least one of radicals $A^1$ or $A^2$ is a dye molecule selected from polymethine dyes which have at least one absorption maximum in the range of 380 to 1200 nm, whereby for the case that $A^1$ and/or $A^2$ is a dye molecule selected from polymethine dyes which have at least one absorption maximum in the range of 380 to 1200 nm, $A^1$ is linked to an N-terminal amino group of amino acid sequence $(X)_m$, and $A^2$ is linked to an amino group of the amino acid lysine or to a hydroxy group of the amino acid serine in any position within the amino acid sequence $(X)_m$;

or a physiologically compatible salt thereof and wherein the polymethine dye is useable as a synthesis component in the solid-phase synthetic production of the conjugates and thus is stable under such conditions.

2. A compound of claim 1, wherein at least one dye molecule $A^1$ and/or $A^2$ is a cyanine, squarilium, croconium, merocyanine or oxonol dye.

3. A compound of claim 1, wherein at least one dye molecule $A^1$ and/or $A^2$ is a cyanine or squarilium dye of formula II:

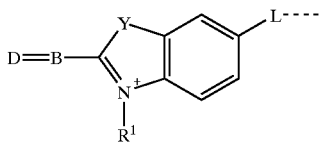

in which
D is a fragment of one of formulae III to VI, whereby the position that is identified

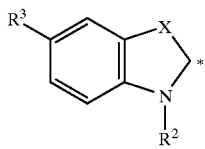

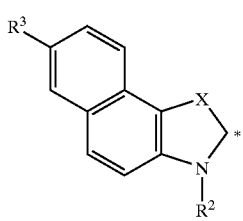

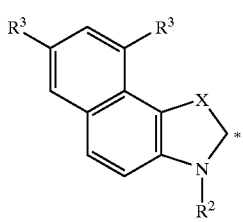

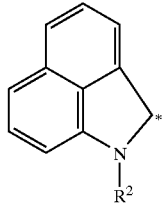

B is a fragment of one of formulae VII to XII

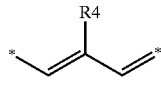

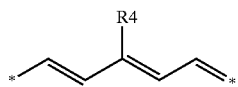

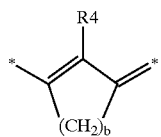

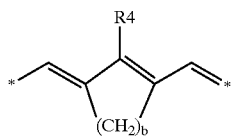

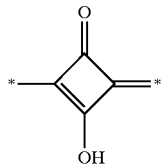

$R^1$ and $R^2$ are $E^1$, $R^3$ is selected from the group consisting of fluorine, chlorine, bromine and iodine atoms, the nitro group and the radicals —$COOE^1$, —$CONE^1E^2$, —$NHCOE^1$, —$NHCONHE^1$, —$NE^1E^2$, —$OE^1$, —$OSO_3E^1$, —$SO_3E^1$, —$SO_2NHE^1$, and —$E^1$, where $E^1$ and $E^2$, independently of one another, are a hydrogen atom, a $C_1$–$C_4$ sulfoalkyl chain, a saturated or unsaturated, branched or straight-chain $C_1$–$C_{50}$ alkyl chain, where the chain or parts of the chain optionally can form one or more aromatic or saturated cyclic $C_5$–$C_6$ units or bicyclic $C_{10}$ units, and whereby the $C_1$–$C_{50}$ alkyl chain is optionally interrupted by 0 to 15 oxygen atoms and/or by 0 to 3 carbonyl groups and/or is substituted with 0 to 5 hydroxy groups, $R^4$ is a hydrogen atom, a fluorine, chlorine, bromine, iodine atom or a branched or straight-chain $C_1$–$C_{10}$ alkyl chain, b is a number 2 or 3, X and Y, independently of one another, are O, S, Se, —CH=CH— or $C(CH_3)_2$, L is a group of one of the formulae below

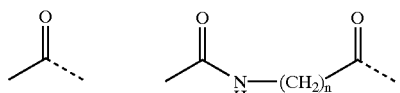

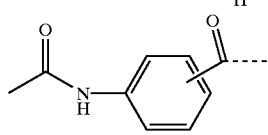

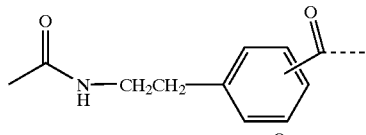

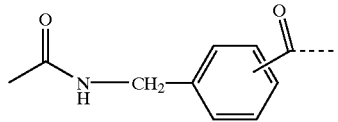

in which
n is a number from 1 to 10.

4. A compound of claim 1, wherein at least one dye molecule $A^1$ and/or $A^2$ is an indocarbocyanine dye, an indodicarbocyanine dye or an indotricarbocyanine dye.

5. A compounds according to claim 4, wherein at least one dye molecule $A^1$ and/or $A^2$ is an indocarbocyanine dye, an indodicarbocyanine dye or an indotricarbocyanine dye of one of formulae XIII or XIV

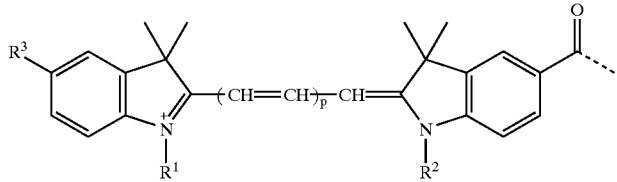

XIII

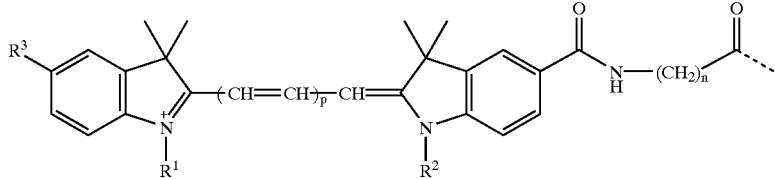

XIV in which
- p is 1, 2 or 3,
- n is a number 1, 2, 3, 4 or 10,
- $R^1$ and $R^2$, independently of one another, are a 4-sulfobutyl, 3-sulfopropyl, 2-sulfoethyl, 3-methyl-3-sulfopropyl, methyl, ethyl or propyl radical, and
- $R^3$ is hydrogen, a chlorine, bromine, iodine atom or a nitro group or a radical —$COOE^1$, —$CONE^1E^2$, —$NHCOE^1$, —$NHCONHE^1$, —$NE^1E^2$, —$OE^1$, —$OSO_3E^1$, —$SO_3E^1$, —$SO_2NHE^1$, wherein
- $E^1$ and $E^2$, independently of one another, are a hydrogen atom or a methyl or ethyl radical or a $C_3$–$C_6$ alkyl radical, which is optionally interrupted by 0 to 2 oxygen atoms and/or by 0 to 1 carbonyl groups and/or is substituted with 0 to 5 hydroxy groups, or $E^1$ and $E^2$ are a poly(oxyethylene)glycol radical with 2 to 30 —$CH_2CH_2O$ units.

6. A compound of claim 4, wherein at least one dye molecule $A^1$ and/or $A^2$ is an indotricarbocyanine dye of one of formulae XV or XVI:

in which
- n is 2 or 3,
- $R^1$ and $R^2$, independently of one another, are a 4-sulfobutyl, 3-sulfopropyl or 2-sulfoethyl radical,
- $R^3$ is a radical —CONH-peptide, —CONH—$(CH_2)_m$—CONH peptide, —CONH—$(CH_2)_n$—NH—CS—NH-peptide or —CONH—$(CH_2)_n$—NHCO—$CH_2$-peptide with m=1 to 10 and n=2 or 3, or $R^3$ is a group of the following formula:

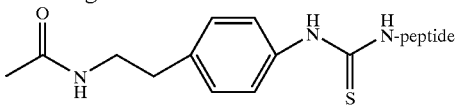

- $R^4$ and $R^5$, independently of one another, are a hydrogen atom, a methyl radical or a hydroxylated alkyl radical,
- $R^6$ is one of the following groups:
  - —$(CH_2)_m$—CONH-peptide with m=0 to 2, or
  - —$(CH_2)_m$—NH—CS—NH-peptide with m=0 to 2,
- and X stands for an oxygen atom or a sulfur atom.

7. A compound according to claim 4, wherein at least one dye molecule $A^1$ and/or $A^2$ is an indotricarbocyanine dye of formula XVIII

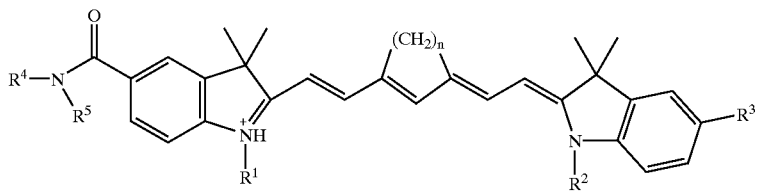

XV

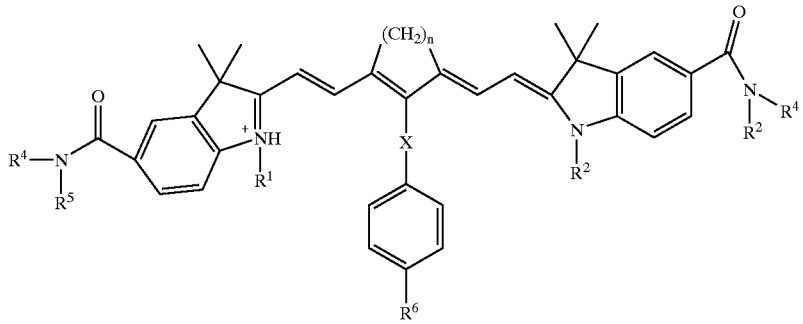

XVI

XVIII

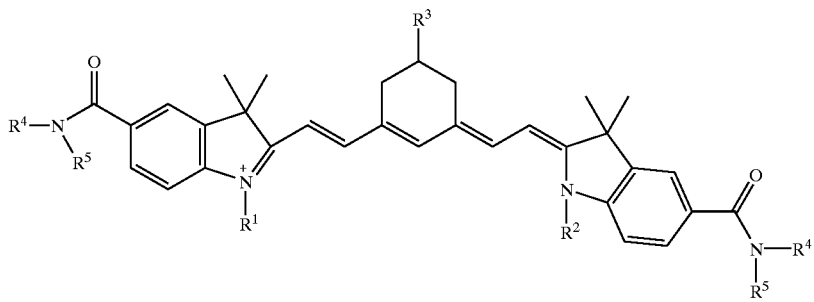

in which
R¹ and R², independently of one another, are a 4-sulfobutyl radical, 3-sulfopropyl radical, or 2-sulfoethyl radical,
R³ is a radical —CONH-peptide, —NH—CS—NH-peptide or —CONH—(CH$_2$)$_n$—NHCO—CH$_2$-peptide with n=2 or 3, or R³ is group of the following formula:

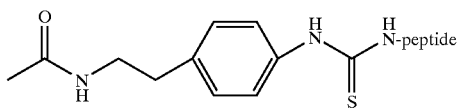

and R⁴ and R⁵, independently of one another, are a hydrogen atom, a methyl radical or a hydroxylated alkyl radical.

8. A compound of claim 6, wherein the hydroxylated alkyl radicals are 2-hydroxyethyl, 3-hydroxypropyl, 2,3-dihydroxypropyl, 1,3-dihydroxy-2-propyl, 2,3,4-trihydroxybutyl, 1,3,4-trihydroxy-2-butyl, or 2,3,4,5,6-pentahydroxyhexyl.

9. A compound of claim according to claim 4, wherein at least one dye molecule A¹ and/or A² is an indocarbocyanine dye, an indodicarbocyanine dye or an indotricarbocyanine dye of formula XIII or XIV

XIII

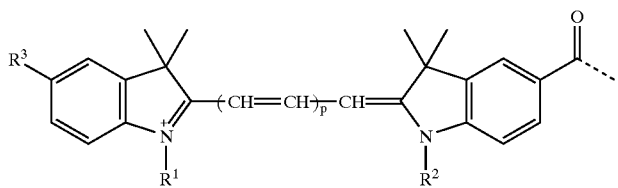

XIV

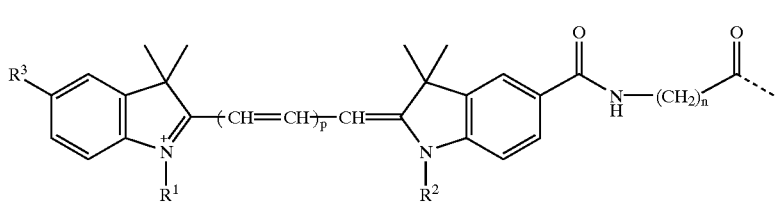

in which
p is 1,2 or 3,
n is 1, 2 or 4,
R¹ and R², independently of one another, are a 4-sulfobutyl or 3-sulfopropyl radical, R³ is hydrogen or a radical —COOE¹ or —CONHE¹, wherein
E¹ is a hydrogen atom or a methyl or ethyl radical or a C$_3$–C$_6$ alkyl radical, which is optionally interrupted by 0 to 2 oxygen atoms and/or by 0 to 1 carbonyl groups and/or is substituted with 0 to 5 hydroxy groups.

10. A compound according to claim 1, wherein (X)$_m$ is the amino acid sequence of a native vaso-active intestinal peptide which is:

HSDAVFTDNYTRLRKQMAVKKYLNSILN (SEQ ID NO: 196).

11. A compound according to claim 10, wherein (X)$_m$ is a retrosynthetic amino acid sequence which is a fragment, partial sequence, derivative or analog of the vaso-active intestinal peptide.

12. A compound according to claim 10, wherein (X)$_m$ is:

| rlrkqmavkkylnsiln | rlrkqmavkkylnsil | rlrkqmavkkylnsi |
|---|---|---|
| (SEQ ID NO: 11) | (SEQ ID NO: 18) | (SEQ ID NO: 25) |
| lrkqmavkkylnsiln | lrkqmavkkylnsil | lrkqmavkkylnsi |
| (SEQ ID NO: 12) | (SEQ ID NO: 19) | (SEQ ID NO: 26) |

-continued

| rkqrnavkkylnsiln | rkqmavkkylnsil | rkqmavkkylnsi |
|---|---|---|
| (SEQ ID NO: 13) | (SEQ ID NO: 20) | (SEQ ID NO: 27) |
| kqmavkkylnsiln | kqmavkkylnsil | kqmavkkylnsi |

```
                    -continued
(SEQ ID NO: 14)     (SEQ ID NO: 21)     (SEQ ID NO: 28)

qmavkkylnsiln       qmavkkylnsil        qrnavkkylnsi
(SEQ ID NO: 15)     (SEQ ID NO: 22)     (SEQ ID NO: 29)

mavkkylnsiln        rnavkkylnsil        mavkkylnsi
(SEQ ID NO: 16)     (SEQ ID NO: 23)     (SEQ ID NO: 30)

avkkylnsiln         avkkylnsil          avkkylnsi
(SEQ ID NO: 17)     (SEQ ID NO: 24)     (SEQ ID NO:31)

RLRKQMAvKKyLNSILN   RLRKQMAvKKyLNSJL    RLRKQMAvKKyLNSI
(SEQ ID NO: 11)     (SEQ ID NO: 18)     (SEQ ID NO: 25)

LRKQMAvKKyLNSILN    LRKQMAvKKyLNSIL     LRKQMAvKKyLNSI
(SEQ ID NO: 12)     (SEQ ID NO: 19)     (SEQ ID NO:26)

RKQMAvKKyLNSILN     RKQMAvKKyLNSIL      RKQMAvKKyLNSI
(SEQ ID NO: 13)     (SEQ ID NO: 20)     (SEQ ID NO: 27)

KQMAvKKyLNSILN      KQMAvKKyLNSIL       KQMAVKKyLNSI
(SEQ ID NO: 14)     (SEQ ID NO: 21)     (SEQ ID NO:28)

QMAvKKyLNSILN       QMAvKKyLNSIL        QMAvKKyLNSI
(SEQ ID NO: 15)     (SEQ ID NO: 22)     (SEQ ID NO:29)

MAvKKyLNSILN        MAVKKyLNSIL         MAvKKyLNSJ
(SEQ ID NO: 16)     (SEQ ID NO: 23)     (SEQ ID NO:30)

AvKKyLNSILN         AvKKyLNSIL          AvKKyLNSJ
(SEQ ID NO: 17)     (SEQ ID NO: 24)     (SEQ ID NO:31).
```

13. A compound according to claim 10, wherein the amino acid sequence, $(X)_m$, is a vaso-active intestinal peptide of the following formula:

$$X^1SDAVX^2TDNX^3TRLRKQMAVKKX^4LNSIL \text{(SEQ ID NO: 153)}$$

in which $X^1$, $X^2$, $X^3$ and $X^4$ represent amino acids or amino acid derivatives that are not genetically encoded.

14. A compound according to claim 13, wherein the amino acids or amino acid derivatives that are not genetically encoded are selected from the group consisting of: naphthalanine, cyclohexylalanine, norleucine, norvaline, α-aminoadipic acid, α-aminobutyric acid, δ-alanine, δ-cyclohexylalanine, ornithine, sarcosine and δ-hydroxylysine.

15. A compound of claim 10, wherein $(X)_m$ is a retrosynthetic amino acid sequence in which 2 to m amino acids are exchanged for the respective D-amino acid, to provide a fragment, partial sequence, derivative or analog of the vaso-active intestinal peptide, whereby m has the above-indicated meaning.

16. A compound of claim 10, wherein the amino acid sequence, $(X)_m$, is:

```
RLRKQMAVKKYLNSILN   RLRKQMAVKKYLNSIL    RLRKQMAVKKYLNSI
(SEQ ID NO: 11)     (SEQ ID NO: 18)     (SEQ ID NO: 25)

LRKQMAVKKYLNSILN    LRKQMAVKKYLNSIL     LRKQMAVKKYLNSI
(SEQ ID NO: 12)     (SEQ ID NO: 19)     (SEQ ID NO: 26)

RKQMAVKKYLNSILN     RKQMAVKKYLNSIL      RKQMAVKKYLNSI
(SEQ ID NO: 13)     SEQ ID NO: 20)      (SEQ ID NO: 27)

KQMAVKKYLNSILN      KQMAVKKYLNSIL       KQMAVKKYLNSI
(SEQ ID NO: 14)     SEQ ID NO: 21)      (SEQ ID NO: 28)

QMAVKKYLNSILN       QMAVKKYLNSIL        QMAVKKYLNSI
(SEQ ID NO: 15)     (SEQ ID NO: 22)     (SEQ ID NO: 29)

MAVKKYLNSILN        MAVKKYLNSIL         MAVKKYLNSI
(SEQ ID NO: 16)     (SEQ ID NO: 23)     (SEQ ID NO: 30)

AVKKYLNSILN         AVKKYLNSIL          AVKKYLNSI
(SEQ ID NO: 17)     (SEQ ID NO: 24)     (SEQ ID NO: 31)

RLRKQMAVKKYLNS      RLRKQMAVKKYLN       RLRKQMAVKKYL
(SEQ ID NO: 32)     (SEQ ID NO: 39)     (SEQ ID NO: 46)

LRKQMAVKKYLNS       LRKQMAYKKYLN        LRKQMAVKKYL
(SEQ ID NO: 33)     (SEQ ID NO: 40)     (SEQ ID NO: 47)

RKQMAVKKYLNS        RKQMAVKKYLN         RKQMAVKKYL
(SEQ ID NO: 34)     (SEQ ID NO: 41)     (SEQ ID NO: 48)

KQMAVKKYLNS         KQMAVKKYLN          KQMAVKKYL
(SEQ ID NO: 35)     (SEQ ID NO: 42)     (SEQ ID NO: 49)

QMAVKKYLNS          QMAVKKYLN           QMAVKKYL
(SEQ ID NO: 36)     (SEQ ID NO: 43)     (SEQ ID NO: 50)

MAVKKYLNS           MAVKKYLN            MAVKKYL
(SEQ ID NO: 37)     (SEQ ID NO: 44)     (SEQ ID NO: 51)

AVKKYLNS            AVKKYLN             AVKKYL
(SEQ ID NO: 38)     (SEQ ID NO: 45)     (SEQ ID NO: 52).
```

17. A compound of claim 10, wherein the amino acid sequence, $(X)_m$, is a VIP peptide of one of the following sequences:

```
FSDAVFTDNYTRLRKQMAVKKYLNSILN    (SEQ ID NO: 53)
ISDAVFTDNYTRLRKQMAVKKYLNSILN    (SEQ ID NO: 54)
LSDAVFTDNYTRLRKQMAVKKYLNSILN    (SEQ ID NO: 55)
HFDAVFTDNYTRLRKQMAVKKYLNSILN    (SEQ ID NO: 56)
HHDAVFTDNYTRLRKQMAVKKYLNSILN    (SEQ ID NO: 57)
HIDAVFTDNYTRLRKQMAVKKYLNSILN    (SEQ ID NO: 58)
HLDAVFTDNYTRLRKQMAVKKYLNSILN    (SEQ ID NO: 59)
HMDAVFTDNYTRLRKQMAVKKYLNSILN    (SEQ ID NO: 60)
HQDAVFTDNYTRLRKQMAVKKYLNSILN    (SEQ ID NO: 61)
HTDAVFTDNYTRLRKQMAVKKYLNSILN    (SEQ ID NO: 62)
HVDAVFTDNYTRLRKQMAVKKYLNSILN    (SEQ ID NO: 63)
HWDAVFTDNYTRLRKQMAVKKYLNSILN    (SEQ ID NO: 64)
HYDAVFTDNYTRLRKQMAVKKYLNSILN    (SEQ ID NO: 65)
HSAAVFTDNYTRLRKQMAVKKYLNSILN    (SEQ ID NO: 66)
HSEAVFTDNYTRLRKQMAVKKYLNSILN    (SEQ ID NO: 67)
HSFAVFTDNYTRLRKQMAVKKYLNSILN    (SEQ ID NO: 68)
HSHAVFTDNYTRLRKQMAVKKYLNSILN    (SEQ ID NO: 69)
HSIAVFTDNYTRLRKQMAVKKYLNSILN    (SEQ ID NO: 70)
HSLAVFTDNYTRLRKQMAVKKYLNSILN    (SEQ ID NO: 71)
HSMAVFTDNYTRLRKQMAVKKYLNSILN    (SEQ ID NO: 72)
HSWAVFTDNYTRLRKQMAVKKYLNSILN    (SEQ ID NO: 73)
HSDFVFTDNYTRLRKQMAVKKYLNSILN    (SEQ ID NO: 74)
HSDGVFTDNYTRLRKQMAVKKYLNSILN    (SEQ ID NO: 75)
HSDMVFTDNYTRLRKQMAVKKYLNSILN    (SEQ ID NO: 76)
```

```
HSDQVFTDNYTRLRKQMAVKKYLNSILN    (SEQ ID NO: 77)
HSDSVFTDNYTRLRKQMAVKKYLNSILN    (SEQ ID NO: 78)
HSDWVFTDNYTRLRKQMAVKKYLNSILN    (SEQ ID NO: 79)
HSDYVFTDNYTRLRKQMAVKKYLNSILN    (SEQ ID NO: 80)
HSDAFFTDNYTRLRKQMAVKKYLNSILN    (SEQ ID NO: 81)
HSDAIFTDNYTRLRKQMAVKKYLNSILN    (SEQ ID NO: 82)
HSDALFTDNYTRLRKQMAVKKYLNSILN    (SEQ ID NO: 83)
HSDAMFTDNYTRLRKQMAVKKYLNSILN    (SEQ ID NO: 84)
HSDATFTDNYTRLRKQMAVKKYLNSILN    (SEQ ID NO: 85)
HSDAWFTDNYTRLRKQMAVKKYLNSILN    (SEQ ID NO: 86)
HSDAYFTDNYTRLRKQMAVKKYLNSILN    (SEQ ID NO: 87)
HSDAVKTDNYTRLRKQMAVKKYLNSILN    (SEQ ID NO: 88)
HSDAVFVDNYTRLRKQMAVKKYLNSILN    (SEQ ID NO: 89)
HSDAVFWDNYTRLRKQMAVKKYLNSILN    (SEQ ID NO: 90)
HSDAVFTDNWTRLRKQMAVKKYLNSILN    (SEQ ID NO: 91)
HSDAVFTDNYTRRRKQMAVKKYLNSILN    (SEQ ID NO: 92)
HSDAVFTDNYTRWRKQMAVKKYLNSILN    (SEQ ID NO: 93)
HSDAVFTDNYTRLRFQMAVKKYLNSILN    (SEQ ID NO: 94)
HSDAVFTDNYTRLRLQMAVKKYLNSILN    (SEQ ID NO: 95)
HSDAVFTDNYTRLRMQMAVKKYLNSILN    (SEQ ID NO: 96)
HSDAVFTDNYTRLRRQMAVKKYLNSILN    (SEQ ID NO: 97)
HSDAVFTDNYTRLRKAMAVKKYLNSILN    (SEQ ID NO: 98)
HSDAVFTDNYTRLRKFMAVKKYLNSILN    (SEQ ID NO: 99)
HSDAVFTDNYTRLRKIMAVKKYLNSILN    (SEQ ID NO: 100)
HSDAVFTDNYTRLRKKMAVKKYLNSILN    (SEQ ID NO: 101)
HSDAVFTDNYTRLRKLMAVKKYLNSJLN    (SEQ ID NO: 102)
HSDAVFTDNYTRLRKMMAVKKYLNSJLN    (SEQ ID NO: 103)
HSDAVFTDNYTRLRKRMAVKKYLNSILN    (SEQ ID NO: 104)
HSDAVFTDNYTRLRKVMAVKKYLNSILN    (SEQ ID NO: 105)
HSDAVFTDNYTRLRKWMAVKKYLNSILN    (SEQ ID NO: 106)
HSDAVFTDNYTRLRKYMAVKKYLNSILN    (SEQ ID NO: 107)
HSDAVFTDNYTRLRKQFAVKKYLNSILN    (SEQ ID NO: 108)
HSDAVFTDNYTRLRKQIAVKKYLNSILN    (SEQ ID NO: 109)
HSDAVFTDNYTRLRKQKAVKKYLNSJLN    (SEQ ID NO: 110)
HSDAVFTDNYTRLRKQLAVKKYLNSILN    (SEQ ID NO: 111)
HSDAVFTDNYTRLRKQQAVKKYLNSILN    (SEQ ID NO: 112)
HSDAVFTDNYTRLRKQRAVKKYLNSILN    (SEQ ID NO: 113)
HSDAVFTDNYTRLRKQWAVKKYLNSILN    (SEQ ID NO: 114)
HSDAVFTDNYTRLRKQMFVKKYLNSILN    (SEQ ID NO: 115)
HSDAVFTDNYTRLRKQMIVKKYLNSILN    (SEQ ID NO: 116)
HSDAVFTDNYTRLRKQMKVKKYLNSILN    (SEQ ID NO: 117)
HSDAVFTDNYTRLRKQMLVKKYLNSILN    (SEQ ID NO: 118)
HSDAVFTDNYTRLRKQMMVKKYLNSILN    (SEQ ID NO: 119)
HSDAVFTDNYTRLRKQMQVKKYLNSILN    (SEQ ID NO: 120)
HSDAVFTDNYTRLRKQMRVKKYLNSILN    (SEQ ID NO: 121)
HSDAVFTDNYTRLRKQMVVKKYLNSILN    (SEQ ID NO: 122)
HSDAVFTDNYTRLRKQMWVKKYLNSILN    (SEQ ID NO: 123)
HSDAVFTDNYTRLRKQMYVKKYLNSILN    (SEQ ID NO: 124)
HSDAVFTDNYTRLRKQMAAKKYLNSILN    (SEQ ID NO: 125)
HSDAVFTDNYTRLRKQMAJKKYLNSILN    (SEQ ID NO: 126)
HSDAVFTDNYTRLRKQMALKKYLNSILN    (SEQ ID NO: 127)
HSDAVFTDNYTRLRKQMAVRKYLNSILN    (SEQ ID NO: 128)
HSDAVFTDNYTRLRKQMAVKRYLNSILN    (SEQ ID NO: 129)
HSDAVFTDNYTRLRKQMAVKWYLNSILN    (SEQ ID NO: 130)
HSDAVFTDNYTRLRKQMAVKKFLNSILN    (SEQ ID NO: 131)
HSDAVFTDNYTRLRKQMAVKKWLNSILN    (SEQ ID NO: 132)
HSDAVFTDNYTRLRKQMAVKKYLASILN    (SEQ ID NO: 133)
HSDAVFTDNYTRLRKQMAVKKYLFSILN    (SEQ ID NO: 134)
HSDAVFTDNYTRLRKQMAVKKYLJSILN    (SEQ ID NO: 135)
HSDAVFTDNYTRLRKQMAVKKYLMSILN    (SEQ ID NO: 136)
HSDAVFTDNYTRLRKQMAVKKYLSSILN    (SEQ ID NO: 137)
HSDAVFTDNYTRLRKQMAVKKYLVSILN    (SEQ ID NO: 138)
HSDAVFTDNYTRLRKQMAVKKYLWSILN    (SEQ ID NO: 139)
HSDAVFTDNYTRLRKQMAVKKYLNNILN    (SEQ ID NO: 140)
HSDAVFTDNYTRLRKQMAVKKYLNRILN    (SEQ ID NO: 141)
HSDAVFTDNYTRLRKQMAVKKYLNWILN    (SEQ ID NO: 142)
HSDAVFTDNYTRLRKQMAVKKYLNYILN    (SEQ ID NO: 143)
HSDAVFTDNYTRLRKQMAVKKYLNSLLN    (SEQ ID NO: 144)
HSDAVFTDNYTRLRKQMAVKKYLNSSLN    (SEQ ID NO: 145)
HSDAVFTDNYTRLRKQMAVKKYLNSWLN    (SEQ ID NO: 146)
HSDAVFTDNYTRLRKQMAVKKYLNSYLN    (SEQ ID NO: 147)
HSDAVFTDNYTRLRKQMAVKKYLNSIFN    (SEQ ID NO: 148)
HSDAVFTDNYTRLRKQMAVKKYLNSIIN    (SEQ ID NO: 149)
HSDAVFTDNYTRLRKQMAVKKYLNSIWN    (SEQ ID NO: 150)
HSDAVFTDNYTRLRKQMAVKKYLNSILW    (SEQ ID NO: 151).
```

18. A compound of claim 10, wherein the amino acid sequence, $(X)_m$, is a vaso-active intestinal peptide of the following formula:

HSDAVFTX$^1$X$^2$Y X$^3$RLRKQMAVK KYLNSILN (SEQ ID NO: 152), in which X$^1$, X$^2$ and X$^3$ are any amino acid.

19. A compound of claim 1, wherein $(X)_m$ is the amino acid sequence of somatostatin which is:

AGCKNFFWKTFTSC    (SEQ ID NO: 9).

20. A compound of claim 19, wherein the amino acid sequence, $(X)_m$, is a somatostatin peptide selected from the group consisting of the following amino acid sequences:

| | |
|---|---|
| AGCKNFFwKTFTSC (SEQ ID NO: 9) | AGCKNFFwKTFTSC (SEQ ID NO: 9) |
| AGCKNFFwKTFTSC (SEQ ID NO: 9) | AGcKNFFwKTFTSC (SEQ ID NO: 9) |
| CKNFFwKTFTSC (SEQ ID NO: 154) | cKNFFwKTFTSC (SEQ ID NO: 154) |
| FFYwKVFT (SEQ ID NO: 155) | |
| fCFwKVCT (SEQ ID NO: 156) | fcFwKVCT (SEQ ID NO: 156) |
| fCYwKVCT (SEQ ID NO: 157) | fcYwKVCT (SEQ ID NO: 157) |
| fCFwKTCT (SEQ ID NO: 158) | fcFwKTCT (SEQ ID NO: 158) |
| fCYwKTCT (SEQ ID NO: 159) | fcYwKTCT (SEQ ID NO: 159) |
| D-NaI-CYwKVC (SEQ ID NO: 195) | D-NaI-cYwKVC (SEQ ID NO: 195) |
| fCywK-Abu-C-NaI (SEQ ID NO: 160) | fcywK-Abu-C-NaI (SEQ ID NO: 160). |

21. A compound of claim 1, wherein $(X)_m$ is the amino acid sequence of neurotensin which is:

pyroglutamic acid-LYENKPRRPYIL (SEQ ID NO: 10).

22. A compound of claim 21, wherein the amino acid sequence, $(X)_m$, is a neurotensin peptide selected from the group consisting of the following amino acid sequences:

one another, are exchanged for their respective D-amino acid or for other L- or D-amino acids, whereby m has the above-indicated meaning.

24. A compound according to claim 1, wherein at least one of the amino acids in $(X)_m$, independently of one another, is exchanged for other amino acids or amino acid derivatives that are not genetically encoded.

25. A compound according to claim 24, wherein as amino acids or amino acid derivatives that are not genetically encoded are selected from the group consisting of: naphthalanine, cyclohexylalanine, norleucine, norvaline, α-aminoadipic acid, α-aminobutyric acid, β-alanine, β-cyclohexylalanine, ornithine, sarcosine and δ-hydroxylysine.

26. A compound according to claim 1, wherein all amino acids in the amino acid sequence $(X)_m$ are exchanged for their respective D-amino acids.

27. A compound of claim 1, wherein the peptide-polymethine-dye conjugate is useable as a synthesis component in the solid-phase-synthetic production of peptides and thus is stable under such synthesis conditions.

28. An optical diagnostic agent for in-vivo diagnosis of diseased tissue areas, which comprises at least one compound of claim 1 together with at least one common adjuvant and/or vehicle as well as diluent.

29. A method for in-vivo diagnosis of tumors, other diseased tissue areas or adenomas using optical detection processes, or for in-vivo fluorescence diagnosis of tumors, tumor cells and/or inflammatory tissues using endoscopic processes in the gastrointestinal tract, esophagus, bronchial tract, bladder or cervix, which comprises administering a compound of claim 1 for enhancing the diagnosis.

30. A method for in-vivo fluorescence diagnosis and/or absorption diagnosis of breast tumors using optical mammography (transillumination or optical tomography of the breast), which comprises administering a compound of claim 1 for enhancing the diagnosis.

31. A process for endoscopic in-vivo fluorescence diagnosis which comprises administering a compound of claim 1 to a patient intravenously or topically by atomization in the

| | | |
|---|---|---|
| | pGlu-LYQNKPRRPFIL (SEQ ID NO: 165) | pGlu-LYENKPRRPYI (SEQ ID NO: 171) |
| pGlu-LYENKPRRPyIL (SEQ ID NO: 10) | pGlu-LYQNKPRRPfIL (SEQ ID NO: 166) | pGlu-LYENKPRRPY (SEQ ID NO: 172) |
| pGlu-LYQNKPRRPYIL (SEQ ID NO: 161) | pGlu-LYENKPRRPWIL (SEQ ID NO: 167) | pGlu-LYENKPRRP (SEQ ID NO: 173) |
| pGlu-LYQNKPRRPyIL (SEQ ID NO: 162) | pGlu-LYENKPRRPwIL (SEQ ID NO: 168) | pGlu-LYENKPRR (SEQ ID NO: 174) |
| pGlu-LYENKPRRPFIL (SEQ ID NO: 163) | pGlu-LYQNKPRRPWIL (SEQ ID NO: 169) | pGlu-LYENKPR (SEQ ID NO: 175) |
| pGlu-LYENKPRRPfIL (SEQ ID NO: 164) | pGlu-LYQNKPRRPwIL (SEQ ID NO: 170) | pGlu-LYENKP (SEQ ID NO: 176) |

| | | | |
|---|---|---|---|
| NKPRRPYIL (SEQ ID NO: 177) | NKPRRPyIL (SEQ ID NO: 177) | NKPRRPfIL (SEQ ID NO: 181) | NKPRRPwIL (SEQ ID NO: 185) |
| KPRRPYIL (SEQ ID NO: 178) | KPRRPyIL (SEQ ID NO: 178) | KPRRPfIL (SEQ ID NO: 182) | KPRRPwIL (SEQ ID NO: 186) |
| PRRPYIL (SEQ ID NO: 179) | PRRPyIL (SEQ ID NO: 179) | PRRPfIL (SEQ ID NO: 183) | PRRPwIL (SEQ ID NO: 187) |
| RRPYIL (SEQ ID NO: 180) | RRPyIL (SEQ ID NO: 180) | RRPfIL (SEQ ID NO: 184) | RRPwIL (SEQ ID NO: 188). |

23. A compound according to claim 1, wherein 2 to m amino acids in amino acid sequence $(X)_m$, independently of gastrointestinal tract, esophagus, bladder or by feeding to the bronchial tubes by inhalation, in the case of atomization, the unbonded, excess portion of the compound is removed by washing, the endoscopic study being performed by local excitation with an excitation wavelength that is selected from the spectral range of 380 to 1200 nm and by position-dependent detection of the specific fluorescence radiation that is emitted by dye.

* * * * *

UNITED STATES PATENT AND TRADEMARK OFFICE
CERTIFICATE OF CORRECTION

PATENT NO. : 6,630,570 B1  
DATED : October 7, 2003  
INVENTOR(S) : Kai Licha et al.

It is certified that error appears in the above-identified patent and that said Letters Patent is hereby corrected as shown below:

<u>Title page,</u>
Item [73], Assignee, reads "Insitut" should read -- Institut --.
Item [63], Foreign Application Priority Data, reads "Sep. 4, 1999" should read -- Apr. 9, 1999 --.

<u>Column 126,</u>
Line 64, reads "compounds" should read -- compound --.

<u>Column 127,</u>
Line 42, XVI formula, reads

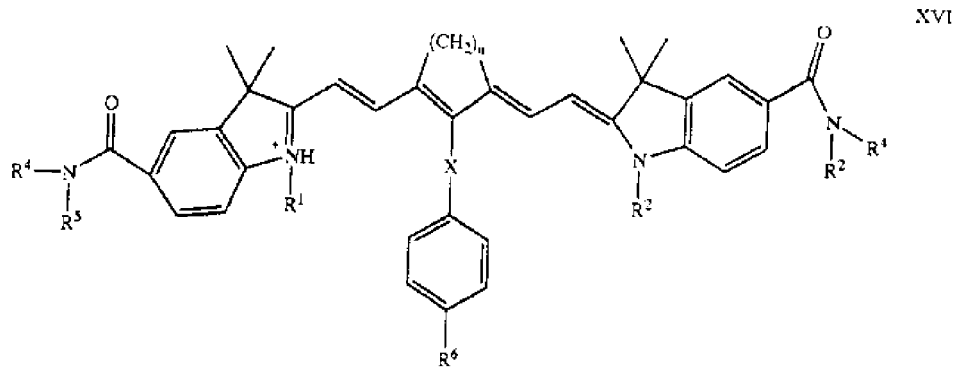

should read

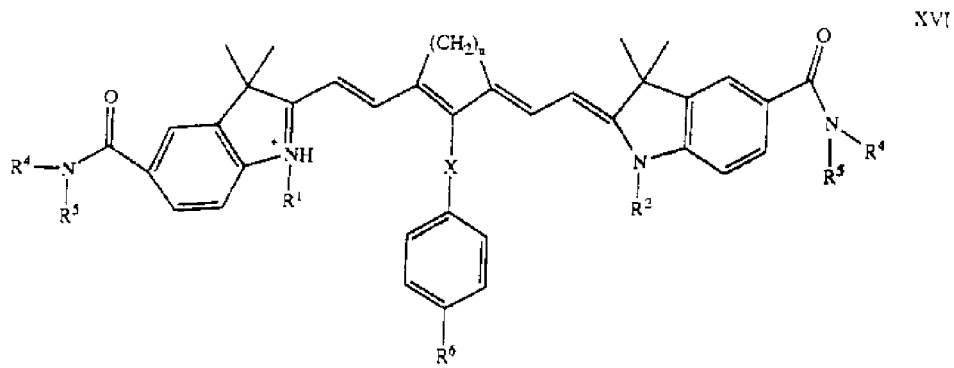

UNITED STATES PATENT AND TRADEMARK OFFICE
CERTIFICATE OF CORRECTION

PATENT NO. : 6,630,570 B1
DATED : October 7, 2003
INVENTOR(S) : Kai Licha et al.

It is certified that error appears in the above-identified patent and that said Letters Patent is hereby corrected as shown below:

Column 128,
Line 20, reads "2or" should read -- 2 or --.
Line 24, reads "CONH peptide," should read -- CONH-peptide --.

Column 130,
Line 37, "(SEQ ID NO: 25)" should be moved up to the end of line 36.
Line 63, reads "rkqrnavkkylnsiln" should read -- rkqmavkkylnsiln --.

Column 131,
Line 4, reads "qrnavkkylnsi" should read -- qmavkkylnsi --.
Line 7, reads "rnavkkylnsil" should read -- mavkkylnsil --.
Line 11, reads "RLRKQMAvKKyLNSJL" should read -- RLRKQMAvKKyLNSIL --.
Line 19, reads "KQMAVKKyLNSI" should read -- KQMAvKKyLNSI --.
Line 23, reads "MAVKKyLNSIL" should read -- MAvKKyLNSIL--
Line 23, reads "MAvKKyLNSJ" should read -- MAvKKyLNSI --.
Line 26, reads "AvKKyLNSJ" should read -- AvKKyLNSI --.
Line 32, reads "$X^1SDAVX^2TDNX^3TRLRKQMAVKKX^4LNSIL(SEQ ID NO: 153)$" should read -- $X^1SDAVX^2TDNX^3TRLRKQMAVKKX^4LNSIL (SEQ ID NO: 153)$ --.
Line 40, reads "δ-alanine," should read -- β-alanine, --.
Line 41, reads "δ-cyclohexylalanine" should read -- β-cyclohexylalanine --.

Column 132,
Line 5, "(SEQ ID NO: 31)" should be moved up to the end of line 4.
Line 9, reads "LRKQMAYKKYLN" should read -- LRKQMAVKKYLN --.

Column 133,
Line 43, reads "HSDAVFTDNYTRLRKLMAVKKYLNSJLN" should read -- HSDAVFTDNYTRLRKLMAVKKYLNSILN --.
Line 44, reads "HSDAVFTDNYTRLRKMMAVKKYLNSJLN" should read -- HSDAVFTDNYTRLRKMMAVKKYLNSILN --.
Line 55, reads "HSDAVFTDNYTRLRKQKAVKKYLNSJLN" should read -- HSDAVFTDNYTRLRKQKAVKKYLNSILN --.

Column 134,
Line 18, reads "HSDAVFTDNYTRLRKQMAJKKYLNSILN" should read -- HSDAVFTDNYTRLRKQMAI KKYLNSILN --.
Line 33, reads "HSDAVFTDNYTRLRKQMAVKKYLJSILN" should read -- HSDAVFTDNYTRLRKQMAVKKYLISILN --.
Line 63, "N    (SEQ ID NO: 152)," should be moved up to the end of line 62.

UNITED STATES PATENT AND TRADEMARK OFFICE
CERTIFICATE OF CORRECTION

PATENT NO. : 6,630,570 B1
DATED : October 7, 2003
INVENTOR(S) : Kai Licha et al.

It is certified that error appears in the above-identified patent and that said Letters Patent is hereby corrected as shown below:

Column 135,
Line 5, reads "AGCKNFFwKTFTSC" should read -- AGcKNFFwKTFTSC --.
Line 8, reads "AGCKNFFwKTFTSC" should read -- AGCKNFFwKTFTSc --.
Line 12, "ID NO: 154)" should be moved up to the end of line 11 after "(SEQ".
Line 41, reads "(SEQ ID NO: 10)" should read -- (SEQ ID NO: 160) --.
Line 48, reads "pGlu-LYQNKPRRPWIL" should read -- pGlu-LYQNKPRRPwIL --.

Signed and Sealed this

Ninth Day of August, 2005

JON W. DUDAS
*Director of the United States Patent and Trademark Office*